United States Patent
Embree

(10) Patent No.: US 10,851,399 B2
(45) Date of Patent: *Dec. 1, 2020

(54) METHODS, APPARATUSES, AND SYSTEMS FOR MICROORGANISM STRAIN ANALYSIS OF COMPLEX HETEROGENEOUS COMMUNITIES, PREDICTING AND IDENTIFYING FUNCTIONAL RELATIONSHIPS AND INTERACTIONS THEREOF, AND SELECTING AND SYNTHESIZING MICROBIAL ENSEMBLES BASED THEREON

(71) Applicant: Native Microbials, Inc., San Diego, CA (US)

(72) Inventor: Mallory Embree, San Diego, CA (US)

(73) Assignee: Native Microbials, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/392,913

(22) Filed: Dec. 28, 2016

(65) Prior Publication Data

US 2017/0107557 A1  Apr. 20, 2017

Related U.S. Application Data

(63) Continuation-in-part of application No. PCT/US2016/039221, filed on Jun. 24, 2016, and a continuation-in-part of application No. 15/349,829, filed on Nov. 11, 2016, which is a continuation of application No. 15/217,575, filed on Jul. 22, 2016, now Pat. No. 9,540,676, which is a continuation of application No. PCT/US2016/039221, filed on Jun. 24, 2016, and a continuation-in-part of application No. 15/217,575, filed on Jul. 22, 2016, now Pat. No. 9,540,676.

(60) Provisional application No. 62/184,650, filed on Jun. 25, 2015, provisional application No. 62/276,142, filed on Jan. 7, 2016.

(51) Int. Cl.

| | |
|---|---|
| A01N 63/00 | (2020.01) |
| C12Q 1/06 | (2006.01) |
| G01N 33/569 | (2006.01) |
| A23K 20/10 | (2016.01) |
| A23K 50/70 | (2016.01) |
| G16B 40/00 | (2019.01) |
| C12Q 1/689 | (2018.01) |

(52) U.S. Cl.
CPC ............ *C12Q 1/06* (2013.01); *A23K 20/10* (2016.05); *A23K 50/70* (2016.05); *C12Q 1/689* (2013.01); *G01N 33/569* (2013.01); *G16B 40/00* (2019.02)

(58) Field of Classification Search
CPC .... C12Q 1/06; C12Q 1/689; C12Q 2600/158; A61K 35/74; A23K 10/18
See application file for complete search history.

(56) References Cited

U.S. PATENT DOCUMENTS

| | | |
|---|---|---|
| 3,484,243 A | 12/1969 | Anderson et al. |
| 4,559,298 A | 12/1985 | Fahy |
| 4,647,536 A | 3/1987 | Mosbach et al. |
| 5,104,662 A | 4/1992 | Kalsta et al. |
| 5,534,271 A | 7/1996 | Ware et al. |
| 5,605,793 A | 2/1997 | Stemmer |
| 5,733,568 A | 3/1998 | Ford |
| 5,766,520 A | 6/1998 | Bronshtein |
| 5,837,458 A | 11/1998 | Minshull et al. |
| 6,210,891 B1 | 4/2001 | Nyren et al. |
| 6,214,337 B1 | 4/2001 | Hayen et al. |
| 6,258,568 B1 | 7/2001 | Nyren |
| 6,274,320 B1 | 8/2001 | Rothberg et al. |
| 6,306,345 B1 | 10/2001 | Bronshtein et al. |
| 6,509,146 B1 | 1/2003 | Bronshtein |
| 6,534,087 B2 | 3/2003 | Busson et al. |
| 6,537,666 B1 | 3/2003 | Bronshtein |
| 6,692,695 B1 | 2/2004 | Bronshtein et al. |
| 6,872,357 B1 | 3/2005 | Bronshtein et al. |
| 6,884,866 B2 | 4/2005 | Bronshtein et al. |
| 6,841,168 B1 | 11/2005 | Worrall |
| 7,074,431 B2 | 7/2006 | Busson et al. |
| 7,153,472 B1 | 12/2006 | Bronshtein |

(Continued)

FOREIGN PATENT DOCUMENTS

| | | |
|---|---|---|
| AR | 105178 | 9/2017 |
| AU | 2016282996 | 1/2018 |

(Continued)

OTHER PUBLICATIONS

Bretonnière, Cédric, et al. "MIC score, a new tool to compare bacterial susceptibility to antibiotics application to the comparison of susceptibility to different penems of clinical strains of Pseudomonas aeruginosa." The Journal of antibiotics 69.11 (2016): 806-810.
Dannemiller, K.C., Lang-Yona, N., Yamamoto, N., Rudich, Y. and Peccia, J., 2014. Combining real-time PCR and next-generation DNA sequencing to provide quantitative comparisons of fungal aerosol populations. Atmospheric environment, 84, pp. 113-121.
Vandeputte D, Kathagen G, D'hoe K, Vieira-Silva S, Valles-Colomer M, Sabino J, Wang J, Tito RY, De Commer L, Darzi Y, Vermeire S. Quantitative microbiome profiling links gut community variation to microbial load. Nature. Nov. 2017;551(7681):507.

(Continued)

*Primary Examiner* — Nancy J Leith
(74) *Attorney, Agent, or Firm* — Cooley LLP

(57) ABSTRACT

Methods, apparatuses, and systems for microorganism strain analysis of complex heterogeneous communities, predicting and identifying functional relationships and interactions thereof, and selecting and synthesizing microbial ensembles based thereon are disclosed. Methods for identifying and determining the absolute cell count of microorganism types and strains, along with identifying the network relationships between active microorganisms and metadata, are also disclosed.

**19 Claims, 18 Drawing Sheets
(4 of 18 Drawing Sheet(s) Filed in Color)**

(56) References Cited

U.S. PATENT DOCUMENTS

| | | |
|---|---|---|
| 7,427,408 B2 | 9/2008 | Merritt et al. |
| 7,998,502 B2 | 8/2011 | Harel |
| 8,071,295 B2 | 12/2011 | Ashby |
| 8,097,245 B2 | 1/2012 | Harel et al. |
| 8,114,396 B2 | 2/2012 | Horn et al. |
| 8,345,010 B2 | 1/2013 | Fitzgibbon et al. |
| 8,349,252 B2 | 1/2013 | Elliott et al. |
| 8,460,726 B2 | 6/2013 | Harel et al. |
| 8,906,668 B2 | 12/2014 | Henn et al. |
| 9,011,834 B1 | 4/2015 | Mckenzie et al. |
| 9,028,841 B2 | 5/2015 | Henn et al. |
| 9,113,636 B2 | 8/2015 | Von Maltzahn et al. |
| 9,179,694 B2 | 11/2015 | Porter et al. |
| 9,180,147 B2 | 11/2015 | Mckenzie et al. |
| 9,206,680 B2 | 12/2015 | Ashby et al. |
| 9,288,995 B2 | 3/2016 | Von Maltzahn et al. |
| 9,295,263 B2 | 3/2016 | Von Maltzahn et al. |
| 9,404,162 B2 | 8/2016 | Boileau et al. |
| 9,446,080 B2 | 9/2016 | Mckenzie et al. |
| 9,469,835 B2 | 10/2016 | Bronshtein |
| 9,532,572 B2 | 1/2017 | Mckenzie et al. |
| 9,532,573 B2 | 1/2017 | Von Maltzahn et al. |
| 9,533,014 B2 | 1/2017 | Henn et al. |
| 9,540,676 B1 | 1/2017 | Zengler et al. |
| 9,562,271 B2 | 2/2017 | Neely |
| 9,593,382 B2 | 3/2017 | Kunin et al. |
| 9,622,485 B2 | 4/2017 | Von Maltzahn et al. |
| 9,642,881 B2 | 5/2017 | Honda et al. |
| 9,649,345 B2 | 5/2017 | Honda et al. |
| 9,700,586 B2 | 7/2017 | Bicalho et al. |
| 9,901,605 B2 | 2/2018 | Garner et al. |
| 9,903,002 B2 | 2/2018 | Zeng et al. |
| 9,909,180 B2 | 3/2018 | Quake et al. |
| 9,938,558 B2 | 4/2018 | Embree |
| 9,993,507 B2 | 6/2018 | Embree et al. |
| 2005/0079244 A1 | 4/2005 | Giffard et al. |
| 2005/0106554 A1 | 5/2005 | Palecek et al. |
| 2005/0158699 A1 | 7/2005 | Kadkake et al. |
| 2005/0239706 A1 | 10/2005 | Backhed et al. |
| 2008/0299098 A1 | 12/2008 | Se et al. |
| 2011/0280840 A1 | 11/2011 | Blaser et al. |
| 2012/0149584 A1 | 6/2012 | Olle et al. |
| 2012/0282675 A1 | 11/2012 | Kim et al. |
| 2013/0204831 A1 | 8/2013 | Reshef et al. |
| 2013/0330307 A1 | 12/2013 | Millan |
| 2014/0162274 A1 | 6/2014 | Kunin et al. |
| 2014/0171339 A1 | 6/2014 | Keku et al. |
| 2015/0093360 A1 | 4/2015 | McKenzie et al. |
| 2015/0213193 A1 | 7/2015 | Apte et al. |
| 2015/0216817 A1 | 8/2015 | Luhman |
| 2015/0218614 A1 | 8/2015 | Henderson et al. |
| 2015/0267163 A1 | 9/2015 | Liao et al. |
| 2015/0376609 A1 | 12/2015 | Hindson et al. |
| 2016/0040119 A1 | 2/2016 | Hashman |
| 2016/0110515 A1 | 4/2016 | Apte et al. |
| 2016/0224749 A1 | 8/2016 | Apte et al. |
| 2016/0230217 A1 | 8/2016 | Apte et al. |
| 2016/0376627 A1 | 12/2016 | Zengler et al. |
| 2017/0196921 A1 | 7/2017 | Embree et al. |
| 2017/0196922 A1 | 7/2017 | Embree et al. |
| 2017/0260584 A1 | 9/2017 | Zheng et al. |
| 2017/0342457 A1 | 11/2017 | Embree et al. |
| 2018/0030516 A1 | 2/2018 | Nawana et al. |
| 2018/0044712 A1 | 2/2018 | Embree |
| 2018/0051310 A1 | 2/2018 | Hallock et al. |
| 2018/0051327 A1 | 2/2018 | Blainey et al. |
| 2018/0070825 A1 | 3/2018 | Apte et al. |
| 2018/0080065 A1 | 3/2018 | Jain |
| 2018/0223325 A1 | 8/2018 | Embree et al. |
| 2018/0310592 A1 | 11/2018 | Embree et al. |
| 2018/0325966 A1 | 11/2018 | Embree et al. |
| 2019/0323055 A1 | 10/2019 | Embree et al. |
| 2019/0371426 A1 | 12/2019 | Embree et al. |
| 2019/0390246 A1 | 12/2019 | Embree |

FOREIGN PATENT DOCUMENTS

| | | |
|---|---|---|
| CA | 2989889 | 12/2016 |
| CN | 104814278 A | 8/2015 |
| CN | 107849597 | 3/2018 |
| EP | 0553444 B1 | 3/1998 |
| EP | 0664671 B1 | 9/2002 |
| EP | 2206791 B1 | 7/2016 |
| JP | 2011-254743 A | 12/2011 |
| JP | 2012-514980 A | 7/2012 |
| KR | 1020130127784 B1 | 11/2013 |
| RU | 2 458 527 C1 | 8/2012 |
| TW | 201713775 | 4/2017 |
| UY | 36754 | 11/2016 |
| UY | 37069 | 6/2017 |
| WO | WO 1993/025232 A1 | 12/1993 |
| WO | WO 2001/012779 A1 | 2/2001 |
| WO | WO 2006/117019 A1 | 11/2006 |
| WO | WO 2008/076975 A1 | 6/2008 |
| WO | WO 2010/111347 A2 | 9/2010 |
| WO | WO 2010/111565 A2 | 9/2010 |
| WO | WO 2010/138522 A2 | 12/2010 |
| WO | WO 2011/075138 A1 | 6/2011 |
| WO | WO 2011/094469 A2 | 8/2011 |
| WO | WO 2012/077038 A1 | 6/2012 |
| WO | WO 2012/122522 A2 | 9/2012 |
| WO | WO 2014/141274 A1 | 9/2014 |
| WO | WO 2015/023461 A2 | 2/2015 |
| WO | WO 2015/068054 A1 | 5/2015 |
| WO | WO 2016/007544 A1 | 1/2016 |
| WO | WO 2016/127956 A1 | 8/2016 |
| WO | WO 2016/153247 A1 | 9/2016 |
| WO | WO 2016/210251 A1 | 12/2016 |
| WO | WO 2017/120495 A1 | 7/2017 |
| WO | WO 2017/131821 A1 | 8/2017 |
| WO | WO 2017/181203 A1 | 10/2017 |
| WO | WO 2017181203 A1 | 10/2017 |
| WO | WO 2018/126026 A1 | 7/2018 |
| WO | WO 2018/126033 A1 | 7/2018 |
| WO | WO 2018/201049 A1 | 11/2018 |

OTHER PUBLICATIONS

Final Office Action in U.S. Appl. No. 15/400,484, dated Dec. 13, 2017.
Gray, Nathan; A revolution in microbiome analysis? Novel method offers 'true' quantitative analysis of gut bacteria; Nov. 17, 2017; New methods to measure and accurately quantify the levels of gut bacteria in stool samples could be a revolution for researchers and companies looking to link our gut bacteria make up to specific issues of health and disease. (https://www.nutraingredients.com/Article/2017/11/17/A-revolution-in-microbiome-analysis-Novel-method-offers-true-quantitative-analysis-of-gut-bacteria); printed Dec. 13, 2017.
Count your blessings: Quantitative microbiome profiling; VIB (The Flanders Institute for Biotechnology); Public Release: Nov. 15, 2017 (https://www.eurekalert.org/pub_releases/2017-11/vfi-cyb111417.php); printed Dec. 13, 2017.
Adams, Rachel; Incorporating quantity into microbiome analysis; (https://www.microbe.net/2017/11/20/incorporating-quantity-into-microbiome-analysis/); printed Dec. 13, 2017.
Chi et al., "Increase in antioxidant enzyme activity, stress tolerance and biocontrol efficacy of Pichia kudriavzevii with the transition from a yeast-like to biofilm morphology." Biological Control, 90: 113-119 (2015).
International Search Report for PCT/US2017/028015, dated Sep. 5, 2017.
Written Opinion for PCT/US2017/028015, dated Sep. 5, 2017.
Vineetha, P. G., et al. "Screening of Lactobacillus isolates from gastrointestinal tract of guinea fowl for probiotic qualities using in vitro tests to select species-specific probiotic candidates." British poultry science 57.4 (2016): 474-482. (cited as "A" Ref in International Search Report of PCT/US2017/028015).
Bretonnière, Cédric, et al. "MIC score, a new tool to compare bacterial susceptibility to antibiotics application to the comparison

(56) References Cited

OTHER PUBLICATIONS of susceptibility to different penems of clinical strains of Pseudomonas aeruginosa." The Journal of antibiotics 69.11 (2016): 806-810. (Published online Mar. 30, 2016; Abstract Provided; entire document cited as "A" Ref in International Search Report of PCT/US2017/028015).
Non-Final Office Action in U.S. Appl. No. 15/400,484, dated May 30, 2017.
Non-Final Office Action in U.S. Appl. No. 15/400,436, dated May 18, 2017.
Non-Final Office Action in U.S. Appl. No. 15/400,484, dated Apr. 4, 2017.
Non-Final Office Action in U.S. Appl. No. 15/400,436, dated Mar. 30, 2017.
Notice of Allowance in U.S. Appl. No. 15/217,575, dated Nov. 8, 2016.
Non-Final Office Action in U.S. Appl. No. 15/217,575, dated Oct. 12, 2016.
Coulon, Jean-Baptiste, et al. "Effect of mastitis and related-germ on milk yield and composition during naturally-occurring udder infections in dairy cows." Animal Research (2002); 51.05: 383-393.
Gröhn, Y. T., et al. "Effect of Pathogen-Specific Clinical Mastitis on Milk Yield in Dairy Cows." Journal of Dairy Science (2004); 87.10: 3358-3374.
International Search Report and Written Opinion, dated Jun. 7, 2017, for PCT International Application No. PCT/US2017/012573, 18 pages.
Li, M., et al. Uncultured Bacterium Clone SJTU_A3_11_21 16S Ribosomal RNA Gene, Partial Sequence. GenBank Accession No. EF403757.1. Submitted Jan. 26, 2007; downloaded from internet <https://www.ncbi.nlm.nih.gov/nucleotide/126114074?report=genbank&log$=nuclalign&blast_rank=1&RID=G57ADV19015> on Apr. 27, 2017, p. 1.
Sirisan, V., et al. "Isolation, identification and growth determination of lactic acid-utilizing yeasts from the ruminal fluid of dairy cattle." Letters in Applied Microbiology (2013); 57.2: 102-107.
Tashiro, Yukihiro, et al. "High butanol production by Clostridium saccharoperbutylacetonicum N1-4 in fed-batch culture with pH-stat continuous butyric acid and glucose feeding method." Journal of Bioscience and Bioengineering (2004); 98.4: 263-268.
Rigobelo et al., "Protective Effect of Probiotics Strains in Ruminants," Submitted: Jan. 26, 2012 Reviewed: May 22, 2012 Published: Oct. 3, 2012, published by INTEC Open source, downloaded from: https://www.intechopen.com/books/probiotic-in-animals/protective-effect-of-probiotics-strains-in-ruminants.
Pavel Petrenko et al: "MetAnnotate: function-specific taxonomic profiling and comparison of metagenomes", BMC Biology, vol. 13, No. 1, Nov. 5, 2015.
Andreas Bremges et al: "Deeply sequenced metagenome and metatranscriptome of a biogas-producing microbial community from an agricultural production-scale biogas plant", GigaScience, vol. 4, No. 1, Jul. 30, 2015.
Corinne Perrier Maurice et al "Xenobiotics Shape the Physiology and Gene Expression of the Active Human Gut Microbiome", Cell, vol. 152, No. 1-2, Jan. 1, 2013.
International Preliminary Report on Patentability PCTUS2016039221, dated Dec. 26, 2017.
Notice of Allowance in U.S. Appl. No. 15/400,484, dated Jan. 16, 2018.
Notice of Allowance in U.S. Appl. No. 15/400,484, dated Jan. 25, 2018.
Notice of Allowance in U.S. Appl. No. 15/400,484, dated Feb. 13, 2018.
Notice of Allowance in U.S. Appl. No. 15/400,484, dated Apr. 2, 2018.
Shi Y, Tyson GW, Eppley JM, DeLong EF. Integrated metatranscriptomic and metagenomic analyses of stratified microbial assemblages in the open ocean. The ISME journal. 2011;5(6):999-1013. doi:10.1038/ismej.2010.189.
International Patent Application No. PCT/US2016/039221, International Preliminary Report on Patentability dated Dec. 26, 2017, 11 pages.
Song, et al., "Comparison of co-expression measures: mutual information, correlation, and model based indices." BMC Bioinformatics (2012); 13: 328, pp. 1-21.
Final Office Action in U.S. Appl. No. 15/400,436, dated Dec. 13, 2017.
Notice of Allowance in U.S. Appl. No. 15/400,484, dated Apr. 27, 2018.
Non-Final Office Action in U.S. Appl. No. 15/349,829 dated May 4, 2018.
Abu-Tarboush, et al. "Evaluation of diet containing lactobacilli on performance, fecal coliform, and lactobacilli of young dairy calves." Animal Feed Science and Technology (1996); 57;1-2: 39-49.
Aikman, P. C., et al. "Rumen pH and fermentation characteristics in dairy cows supplemented with Megasphaera elsdenii NCIMB 41125 in early lactation." Journal of Dairy Science (2011); 94.6: 2840-2849.
Almeida, Elionor RP, et al. "Transgenic expression of two marker genes under the control of an *Arabidopsis* rbcS promoter: Sequences encoding the Rubisco transit peptide increase expression levels." Molecular and General Genetics MGG (1989); 218.1: 78-86.
Bauman et al., "Nutrigenomics, Rumen-Derived Bioactive Fatty Acids, and the Regulation of Milk Fat Synthesis," Annual Review of Nutrition (2011); 31: 299-319.
Bennett et al., "Toward the 1,000 dollars human genome," Pharmacogenomics (2005); 6(4):373-382.
Bentley et al., "Accurate whole genome sequencing using reversible terminator chemistry," Nature (2008); 456: 53-59.
Blondel et al., "Fast unfolding of communities in large networks," Journal of Statistical Mechanics: Theory and Experiment, (2008); 2008.10.
Boyd, J., "Effects of the addition of direct-fed microbials and glycerol to the diet of lactating dairy cows on milk yield and apparent efficiency of yield." Journal of Dairy Science (2011); 94.9: 4616-4622.
Cacite, F., and Weimer, P. J. "1611 Ruminal dosing with Megasphaera elsdenii and strain persistence are associated with milk fat depression in Holstein cows." J. Anim. Sci vol. (2016); 94, E-Suppl. 5/J. Dairy Sci. vol. 99, E-Suppl. 1, p. 784, 1 page.
Chiquette, J., et al. "Use of Prevotella bryantii 25A and a commercial probiotic during subacute acidosis challenge in midlactation dairy cows." Journal of Dairy Science (2012); 95.10: 5985-5995.
Chiquette, J., et al. "Prevotella bryantii 25A used as a probiotic in early-lactation dairy cows: effect on ruminal fermentation characteristics, milk production, and milk composition." Journal of Dairy Science (2008); 91.9: 3536-3543.
Colby, S. R. "Calculating synergistic and antagonistic responses of herbicide combinations." Weeds (1967); 15(1): 20-22.
Crameri, Andreas, et al. "Molecular evolution of an arsenate detoxification pathway by DNA shuffling." Nature Biotechnology (1997); 15.5: 436-438.
Crameri, Andreas, et al. "DNA shuffling of a family of genes from diverse species accelerates directed evolution." Nature (1998); 391.6664: 288-291.
Caporaso et al., "Ultra-high-throughput microbial community analysis on the Illumina HiSeq and MiSeq platforms," The ISME Journal (2012); 6: 1621-1624.
Embree, Mallory, et al. "Networks of energetic and metabolic interactions define dynamics in microbial communities." Proceedings of the National Academy of Sciences (2015); 112.50: 15450-15455.
De Menezes, Alexandre B., et al. "Microbiome analysis of dairy cows fed pasture or total mixed ration diets." FEMS Microbiology Ecology (2011); 78.2: 256-265.
Dosogne, Hilde, et al. "Differential leukocyte count method for bovine low somatic cell count milk." Journal of Dairy Science (2003); 86.3: 828-834.
Fadrosh et al., "An improved dual-indexing approach for multiplexed 16S rRNA gene sequencing on the Illumina MiSeq platform," Microbiome (2014); 2:6.

(56) References Cited

OTHER PUBLICATIONS

Falkowski et al., "Primary production of the biosphere: integrating terrestrial and oceanic components," Science (1998); 281(5374): 237-240.
Higginbotham, G. E., and Bath, D. L. "Evaluation of Lactobacillus Fermentation Cultures in Calf Feeding Systems1." Journal of Dairy Science (1993); 76.2: 615-620.
Huhtanen, Pekka, et al. "Effect of increasing ruminal butyrate on milk yield and blood constituents in dairy cows fed a grass silage-based diet." Journal of Dairy Science (1993); 76.4: 1114-1124.
Ingolia et al., "Genome-wide analysis in vivo of translation with nucleotide resolution using ribosome profiling," Science (2009); 324(5924): 218-223.
Ingolia, N.T., "Ribosome profiling: new views of translation, from single codons to genome scale," Nat Rev Genet. (2014); 15(3): 205-213.
International Patent Application No. PCT/US2016/039221, International Search Report and Written Opinion dated Sep. 23, 2016, 14 pages.
Jewell et al., "Ruminal Bacterial Community Composition in Dairy Cows is Dynamic over the Course of Two Lactations and Correlates with Feed Efficiency," Applied and Environmental Microbiology (2015); 81(14): 4697-4710.
Jones, Jonathan D.G., et al. "High level expression of introduced chimaeric genes in regenerated transformed plants." The EMBO Journal (1985); 4.10 : 2411-2418.
Kim, Y. J., et al. "The enrichment of a ruminal bacterium (*Megasphaera elsdenii* YJ-4) that produces the trans-10, cis-12 isomer of conjugated linoleic acid." Journal of Applied Microbiology (2002); 92.5: 976-982.
Kõljalg, Urmas, et al. "UNITE: a database providing web-based methods for the molecular identification of ectomycorrhizal fungi." New Phytologist (2005); 166.3: 1063-1068.
Lan, Yemin, et al. "Using the RDP classifier to predict taxonomic novelty and reduce the search space for finding novel organisms." PLoS One (2012); 7.3: e32491.
Lange et al., "Cost-efficient high-throughput HLA typing by MiSeq amplicon sequencing," BMC Genomics (2014); 15.1:63, 11 pages.
Lee, Dong-Hun, et la. . "Nonradioactive method to study genetic profiles of natural bacterial communities by PCR-single-strand-conformation polymorphism." Applied and Environmental Microbiology (1996); 62.9: 3112-3120.
Lee, K., et al. "Antiobesity effect of trans-10, cis-12-conjugated linoleic acid-producing Lactobacillus plantarum PL62 on diet-induced obese mice." Journal of Applied Microbiology (2007); 103.4: 1140-1146.
Lowe, Susan E., et al. "Growth of anaerobic rumen fungi on defined and semi-defined media lacking rumen fluid." Journal of General Microbiology (1985); 131.9: 2225-2229.
Lee et al., "Nonradioactive Method to Study Genetic Profiles of Natural Bacterial Communities by PCR-Single-Strand-Conformation Polymorphism," Applied and Environmental Microbiology (1996); 62(9): 3112-3120.
Li et al., "Quantifying absolute protein synthesis rates reveals principles underlying allocation of cellular resources," Cell (2013);157(3): 624-635.
Mardis, Elaine R., "Next Generation DNA Sequencing Methods," Annu. Rev. Genomics Hum. Genet. (2008); 9: 387-402.
McGilliard, M. L., and Stallings, C.C. "Increase in milk yield of commercial dairy herds fed a microbial and enzyme supplement." Journal of Dairy Science (1998); 81.5: 1353-1357.
Margulies et al., "Genome sequencing in microfabricated high-density picolitre reactors," Nature (2005); 437: 376-380.
Mohammed, R., et al. "Changes in ruminal bacterial community composition following feeding of alfalfa ensiled with a lactic acid bacterial inoculant." Journal of Dairy Science (2012); 95.1: 328-339.
Massol-Deya, A.A. et al., Bacterial community fingerprinting of amplified 16S and 16-23S ribosomal DNA gene sequences and restriction endonuclease analysis (ARDRA). In: Akkermans, A.D.L, et al., (Eds.), Molecular Microbial Ecology Manual, vol. 3.3.2. Kluwer Academic Publishers, Dordrecht, pp. 1-8, 1995.
Moore, Jeffrey C., et al. "Strategies for the in vitro evolution of protein function: enzyme evolution by random recombination of improved sequences." Journal of Molecular Biology (1997); 272.3: 336-347.
Mitra et al., "Analysis of the intestinal microbiota using SOLiD 16S rRNA gene sequencing and SOLiD shotgun sequencing," BMC Genomics (2013); 14(Suppl 5):S16.
Palmonari et al., "pH dynamics and bacterial community composition in the rumen of lactating dairy cows," J. Dairy Sci. (2010); 93(1): 279-287.
Peckham et al., "SOLiD™ Sequencing and 2-Base Encoding," San Diego, CA: American Society of Human Genetics, Poster No. 2624 (2007), 1 page.
Petri, Renee M., et al. "Characterization of the core rumen microbiome in cattle during transition from forage to concentrate as well as during and after an acidotic challenge." PLoS One (2013); 8.12: e83424.
Pool-Zobel et al., "Overview of Experimental Data on Reduction of Colorectal Cancer Risk by Inulin-Type Fructans," J. Nutr. (2007); 137: 2580S-2584S.
Qiu, Yu, et al. "Characterizing the interplay between multiple levels of organization within bacterial sigma factor regulatory networks." Nature Communications (2013); 4: 1755 (pp. 1-10).
Raeth-Knight, M. L., et al. "Effect of direct-fed microbials on performance, diet digestibility, and rumen characteristics of Holstein dairy cows." Journal of Dairy Science (2007); 90.4: 1802-1809.
Ramirez-Farias et al., "Effect of inulin on the human gut microbiota: stimulation of *Bifidobacterium adolescentis* and *Faecalibacterium prausnitzii*," Br J Nutr (2009); 101(4): 541-550.
Ranjard et al., "Sampling strategy in molecular microbial ecology: influence of soil sample size on DNA fingerprinting analysis of fungal and bacterial communities," Environmental Microbiology 5(11); 1111-1120 (2003).
Rook, J. A. F., and Balch, C.C. "The effects of intraruminal infusions of acetic, propionic and butyric acids on the yield and composition of the milk of the cow." British Journal of Nutrition (1961); 15.03: 361-369.
Sandri et al., "Microbial biodiversity of the liquid fraction of rumen content from lactating cows," Animal (2014); 8(4): 572-579.
Sanger et al., "DNA sequencing with chain-terminating inhibitors," Proc Natl. Acad. Sci. USA (1977); 74(12): 5463-5467.
San Miguel et al., "Effects of organochlorines on microbial diversity and community structure in *Phragmites australis* rhizosphere," Appl Microbiol Biotechnol (2014); 98(9): 4257-4266.
Scheinert et al., "Molecular differentiation of bacteria by PCR amplification of the 16-23S rRNA spacer," J Microbiol Meth (1996); 26: 103-117.
Schloss, Patrick D., et al. "Assessing and improving methods used in operational taxonomic unit-based approaches for 16S rRNA gene sequence analysis." Applied and Environmental Microbiology (2011); 77.10: 3219-3226.
Schogor, Ana L.B., et al. "Ruminal *prevotella* spp. may play an important role in the conversion of plant lignans into human health beneficial antioxidants." PloS One (2014); 9.4: e87949. 10 pages.
Schwieger et al.,"A New Approach to Utilize PCR-Single-Strand-Conformation Polymorphism for the 16S rRNA Gene-Based Microbial Community Analysis," Applied and Environmental Microbiology (1998); 64(12): 4870-4876.
Segata et al., "Computational meta'omics for microbial community studies," Molecular Systems Biology 9(1): 666 (2013).
Segata, Nicola, et al. "Metagenomic biomarker discovery and explanation." Genome Biology (2011); 12.6: R60.
Shanks, Orin C., et al. "Community structures of fecal bacteria in cattle from different animal feeding operations." Applied and Environmental Microbiology (2011); 77.9; 2992-3001.
Stemmer, Willem PC. "Rapid evolution of a protein in vitro by DNA shuffling." Nature (1994); 370.6488: 389-391.

(56) References Cited

OTHER PUBLICATIONS

Stemmer, Willem P. "DNA shuffling by random fragmentation and reassembly: in vitro recombination for molecular evolution." Proceedings of the National Academy of Sciences (1994); 91.22: 10747-10751.

Tao, N., et al. "Variations in bovine milk oligosaccharides during early and middle lactation stages analyzed by high-performance liquid chromatography-chip/mass spectrometry." Journal of Dairy Science (2009); 92.7: 2991-3001.

Human Microbiome Project Consortium. "Structure, function and diversity of the healthy human microbiome." Nature (2012); 486(7402): 207-214.

Van Houtert, M. F. J. "The production and metabolism of volatile fatty acids by ruminants fed roughages: A review." Animal Feed Science and Technology (1993); 43(3): 189-225.

Vandamme, Peter, et al. "Polyphasic taxonomy, a consensus approach to bacterial systematics." Microbiological Reviews (1996); 60.2: 407-438.

Wagg et al. "Soil biodiversity and soil community composition determine ecosystem multifunctionality." Proceedings of the National Academy of Sciences (2014); 111(14): 5266-5270.

Yarza, Pablo, et al. "Uniting the classification of cultured and uncultured bacteria and archaea using 16S rRNA gene sequences." Nature Reviews Microbiology (2014); 12.9: 635-645.

Zebeli, Qendrim, et al. "Intraruminal administration of Megasphaera elsdenii modulated rumen fermentation profile in mid-lactation dairy cows." Journal of Dairy Research (2012); 79.01; 16-25.

Zhou et al. "High-Throughput Metagenomic Technologies for Complex Microbial Community Analysis: Open and Closed formats." MBio (2015); 6(1): e02288-14, 17 pages.

Zhang, Ji-Hu, et al. "Directed evolution of a fucosidase from a galactosidase by DNA shuffling and screening." Proceedings of the National Academy of Sciences (1997); 94.9: 4504-4509.

Bikel et al., "Combining metagenomics, metatranscriptomics and viromics to explore novel microbial interactions: towards a systems-level understanding of human microbiome," Computational and Structural Biotechnology Journal (2015), 13:390-401.

Boaro et al., "Integrated 'omics analysis for studying the microbial community response to a pH perturbation of a cellulose-degrading bioreactor culture," FEMS Microbiol Ecol (2014), 90:802-815.

Borling, "Feed improvement by energy efficient storage using Pichia anomala inoculated ensiled cereal grain," Master thesis 2010:1, Uppsala BioCenter Department of Microbiology Faculty of Natural Resources and Agriculture Sciences Swedish University of Agricultural Sciences, ISSN 1101-8151, 25 pages.

Bremges et al., "Deeply sequenced metagenome and metatranscriptome of a biogas-producing microbial community from an agricultural production-scale biogas plant," GigaScience (2015) 4:33, 6 pages.

Extended European Search Report for European Application No. 16815367.4 dated Jan. 9, 2019.

Final Office Action in U.S. Appl. No. 15/400,436, dated Jan. 28, 2019.

GenBank Accession No. JF629154 Uncultured bacterium clone GDIC21K01DL4MU 16S ribosomal RNA gene, partial sequence, Aug. 3, 2011 [online]. (Retrieved online Aug. 14, 2018].

International Search Report and Written Opinion, dated Feb. 28, 2018, for PCT International Application No. PCT/US2018/068753, 11 pages.

International Search Report and Written Opinion, dated Feb. 28, 2018, for PCT International Application No. PCT/US2018/068758, 9 pages.

International Search Report and Written Opinion, dated Mar. 22, 2018, for PCT International Application No. PCT/US2017/068740, 16 pages.

International Search Report and Written Opinion, dated Sep. 6, 2018, for PCT International Application No. PCT/US2018/029953, 17 pages.

Kleinsteuber et al., "Population Dynamics within a Microbial Consortium during Growth on Diesel Fuel in Saline Environments," Appl. Environ. Microbial. 2006, 72(5):3531-3542.

Maurice et al., "Xenobiotics Shape the Physiology and Gene Expression of the Active Human Guy Microbiome," Cell, 152, Jan. 17, 2013, pp. 39-50.

McCarren et al., "Microbial community transcriptomes reveal microbes and metabolic pathways associated with dissolved organic matter turnover in the sea," PNAS, Sep. 21, 2010, vol. 107, No. 38, pp. 16420-16427.

Muller et al., "Condensing the omics fog of microbial communities," Trends in Microbiology, Jul. 2013, vol. 21, No. 7, pp. 325-333.

Non-Final Office Action in U.S. Appl. No. 15/948,965 dated Jan. 23, 2019.

Non-Final Office Action in U.S. Appl. No. 15/948,965 dated Jun. 26, 2018.

Non-Final Office Action in U.S. Appl. No. 16/029,398 dated Feb. 26, 2019.

Non-Final Office Action in U.S. Appl. No. 15/400,436, dated Aug. 31, 2018.

Petrenko et al., "MetAnnotate: function-specific taxonomic profiling and comparsion of metagenomes," BMC Biology (2015) 13:92, 8 pages.

Restriction / Election Requirement in U.S. Appl. No. 16/029,398 dated Sep. 18, 2018.

Restriction / Election Requirement in U.S. Appl. No. 16/207,811 dated Feb. 12, 2019.

Shi, et al., Integrated metatranscriptomic and metagenomics analyses of stratified microbial assemblages in the open ocean, The ISME Journal (2011) 5, 999-1013.

Ursell et al., "Xenobiotics and the human gut microbiome: metatranscriptomics reveal the active players," Cell Metab. Mar. 5, 2013; 17(3): 317-318.

Albertsen et al., "Genome sequences of rare, uncultured bacteria obtained by differential coverage binning of multiple metagenomes," Nature Biotechnology, (2013) vol. 31, pp. 533-538.

Alzahal et al., "Use of a direct-fed microbial product as a supplement during the transition period in dairy cattle," J. Dairy Sci. 2014, 97 :7102-7114 http://dx.doi.org/ 10.3168/jds.2014-8248.

Anders et al., "Differential expression analysis for sequence count data," Genome Biology, 2010, 11:R106, 12 pages doi: 10.1186/gb-2010-11-10-r106.

Bach et al., "Kernel Independent Component Analysis" Journal of Machine Learning Research (2002)3: 1-48.

Bankevich et al., "SPAdes: A New Genome Assembly Algorithm and Its Applications to Single-Cell Sequencing," Journal of Computational Biology, 2012, vol. 19, No. 5, pp. 455-477.

Baraniuk, "Neural Regulation of Mucosal Function," Pulm Pharmacol Ther. 2008; 21(3): 442-448.

Baym et al., "Inexpensive Multiplexed Library Preparation for Megabase-Sized Genomes," PLoS ONE (2015) 10(5): e0128036, 15 pages.

Blomqvist, "On a measure of dependence between two random variables," The Annals of Mathematical Statistics (1950): 593-600.

Blum et al., "Distribution free tests of independence based on the sample distribution function," The Annals of Mathematical Statistics (1961): 485-498.

Bolger et al., "Plant genome sequencing—applications for crop improvement," Current Opinion in Biotechnology, Apr. 2014, vol. 26, pp. 31-37.

Bouwmans et al., "Decomposition into low-rank plus additive matrices for background/foreground separation: A review for a comparative evaluation with a large-scale dataset," Computer Science Review, Feb. 2017, vol. 23, pp. 1-71.

Brady and Salzberg, "Phymm and PhymmBL: Metagenomic Phylogenetic Classification with Interpolated Markov Models," Nature Methods, 2009 6(9):673-676.

Breiman, L., "Random Forests," Machine Learning, 2001, 45, 5-32.

Breiman, "Arcing Classifiers" The Annals of Statistics, 1998, vol. 26, No. 3, 801-849.

Breiman et al. "Estimating Optimal Transformations for Multiple Regression and Correlation: Rejoinder," Journal of the American Statistical Association, (1985) vol. 80, No. 391: 614-19, doi:10.2307/2288477.

Bryant et al., "An Improved Nonselective Culture Medium for Ruminal Bacteria and Its Use in Determining Diurnal Variation in

(56) References Cited

OTHER PUBLICATIONS

Numbers of Bacteria in the Rumen," J. Dairy Sci. 1961, 44:1446-1456. doi:10.3168/jds.S0022-0302(61)89906-2.

Buzatu et al., "An Integrated Flow Cytometry-Based System for RealTime, High Sensitivity Bacterial Detection and Identification," PLoS ONE (2014) 9(4): e94254, 10 pages.

Carpenter et al., "Hot topic: Early postpartum treatment of commercial dairy cows with nonsteroidal antiinflammatory drugs increases whole-lactation milk yield," J. Dairy Sci. 2016, 99:672-679 http://dx.doi.org/10.3168/jds.2015-10048.

Chiquette et al., "Efficacy of the direct-fed microbial Enterococcus faecium alone or in combination with *Saccharomyces cerevisiae* or *Lactococcus lactis* during induced subacute ruminal acidosis," J. Dairy Sci. 2015, 98:190-203 http://dx.doi.org/ 10.3168/jds.2014-8219.

Cole et al., "Ribosomal Database Project: data and tools for high throughput rRNA analysis." Nucleic Acids Research (2014); 42 (D1): D633-D642.

Conesa et al., "Blast2GO: a universal tool for annotation, visualization and analysis in functional genomics research," Bioninformatics, 2005, vol. 21, No. 18, pp. 3674-3676.

Connor et al. "The Assembly of Species Communities: Chance or Competition?" Ecology, vol. 60, No. 6 (Dec. 1979), pp. 1132-1140.

Dick et al., "Community-wide analysis of microbial genome sequence signatures," Genome Biology 2009, 10:R85, 16 pages.

Earl et al., "Assemblathon 1: A competitive assessment of de novo short read assembly methods," Genome Research, 2011, 21:2224-2241.

Edgar and Flyvberg, "Error filtering, pair assembly and error correction for next-generation sequencing reads." Bioinformatics (2015); 31 (21): 3476-3482.

Edgar, "SINTAX: A simple non-Bayesian taxonomy classifier for 16S and ITS sequences." BioRxiv (2016); 074161, 20 pages.

Farine et al., in "Constructing, Conducting and Interpreting Animal Social Network Analysis" Journal of Animal Ecology, 2015, 84, pp. 1144-1163. doi:10.1111/1365-2656.12418.

Feehery et al., "A Method for Selectively Enriching Microbial DNA from Contaminating Vertebrate Host DNA," PloS One (2013) 8(10):e76096.

Ferraretto et al., "Effect of direct-fed microbial supplementation on lactation performance and total-tract starch digestibility by midlactation dairy cow," Prof. Anim. Sci. (2015) 31:63-67, doi:10.15232/pas.2014-01369.

Franks et al., "Sampling Animal Association Networks with the Gambit of the Group" Behav Ecol Sociobiol (2010) 64:493, doi:10.1007/x00265-0098-0865-8.

Gao et al., "Efficient Estimation of Mutual Information for Strongly Dependent Variables" Proceedings of the 18th International Conference on Artificial Intelligence and Statistics (AISTATS), 2015, San Diego, CA, JMLR: W&CP vol. 38.

Giannoukos et al., "Efficient and robust RNA-seq process for cultured bacteria and complex community transcriptomes," Genome Biology 2012, 13:r23, 13 pages.

Gieser et al., "A Nonparametric Test of Independence Between Two Vectors," Journal of the American Statistical Association, vol. 92, No. 438, Jun. 1977, pp. 561-567.

Gilbert et al., "Microbial Metagenomics: Beyond the Genome," Annual Review of Marine Science, 2011, 3(1):347-371.

Grabherr et al., "Full-length transcriptome assembly from RNA-seq data without a reference genome," Nat Biotechnol. May 15, 2011;29(7):644-52.

Gretton et al., "A Kernal Two-Sample Test," Journal of Machine Learning Research 13 (2012) 723-773.

Howe et al., "Challenges and opportunities in understanding microbial communities with metagenome assembly (accompanied by IPython Notebook tutorial)," Frontiers in Microbiology, Jul. 2015, vol. 6, Article 6782017, 4 pages.

Howe et al., "Is H3K4me3 instructive for transcription activation?" Bioessays. Jan. 2017;39(1):1-12.

Huson et al., "Integrative analysis of environmental sequences using MEGAN4," Genome Research, 2011,21:1552-1560.

Indyk and Motwani, "Approximate Nearest Neighbors: Towards Removing the Curse of Dimensionality," Theory of Computing, 1998, pp. 604-613.

Kamath et al., "HINGE: long-read assembly achieves optimal repeat resolution," Genome Research, 2017, 27:747-756.

Kamphorst and Lewis, "Editorial overview: Recent innovations in the metabolomics revolution," Current Opinion in Biotechnology, Feb. 2017, vol. 43, pp. iv-vii.

Kang et al., "MetaBAT, an Efficient Tool for Accurately Reconstructing Single Genomes from Complex Microbial Communities," PeerJ (Aug. 2015) 3:e1165.

Kapur et al., "Gene expression prediction using low-rank matrix completion," BMC Bioinformatics, 2016; 17:243, 13 pages.

Karlin et al., "Compositional differences within and between eukaryotic genomes," PNAS USA, Sep. 1997, vol. 94, pp. 10227-10232.

Kelley and Salzberg, "Clustering metagenomic sequences with interpolated Markov models," BMC Bioinformatics 2010, 11:544, 12 pages.

Keshavan et al., "Low-rank matrix completion with noisy observations: a quantitative comparison," Proceedings of Annual Allerton Conference on Communication, Control, and Computing, 2009, 7 pages.

Kluger et al., "Spectral Biclustering of Microarray Data: Coclustering Genes and Conditions," Genome Research, 2013, 13:703-716.

Korem et al., "Growth dynamics of gut microbiota in health and disease inferred from single metagenomic samples," Science, 2015; 349(6252): 1101-1106.

Koren et al., "Hybrid error correction and de novo assembly of singlemolecule sequencing reads," Nat Biotechnol., 2012; 30(7): 693-700.

Koren et al., "Canu: scalable and accurate long-re d assembly via adaptive k-mer weighting and repeat separation," Genome Research, 2017, 27:722-736.

Krause, D., and Russell, J.B., "Symposium : Ruminal Microbiology How Many Ruminal Bacteria Are There?" J. Dairy Sci. 1996, 79:1467-1475. doi:10.3168/jds.S0022-0302(96)76506-2.

Lane, et al., "16S/23S rRNA Sequencing," Nucleic Acid Techniques in Bacterial Systematics, Chapter 6, pp. 115-175, 1991.

Langdon, W.B., "Performance of genetic programming optimised Bowtie2 on genome comparison and analytic testing (GCAT) benchmarks," BioData Mining (2015) 8:1, 7 pages.

Langmead and Salzberg, "Fast gapped-read alignment with Bowtie 2," Nature Methods 2012 9(4):357-59.

Li, H., "Minimap and miniasm: fast mapping and de novo assembly for noisy long sequences," Bioinformatics, 2016, 32(14), 2103-2110.

Liu, "Modified Bagging of Maximal Information Coefficient for Genome-wide Identification," Int. J. Data Mining and Bioinformatics, vol. 14, No. 3, 2016, pp. 229-257.

Lopez-Paz et al., "The Randomized Dependence Coefficient," Advances in Neural Information Processing Systems (2013).

Lozupone et al., "UniFrac: an effective distance metric for microbial community comparison," The ISME Journal, 2011, 5(2): 169-172.

Lu et al., "Metabolomic analysis via reversed-phase ion-pairing liquid chromatography coupled to a stand alone orbitrap mass spectrometer," Anal Chem. Apr. 15, 2010; 82(8): 3212-3221.

Mazumder et al., "Spectral Regularization Algorithms for Learning Large Incomplete Matrices," Journal of Machine Learning Research 11 (2010) 2287-2322.

McCann et al., "High-throughput Methods Redefine the Rumen Microbiome and Its Relationship with Nutrition and Metabolism," Bioinformatics and Biology Insights 2014:8 109-125 doi: 10.4137/BBI.S15389.

McIntyre et al., "Single-molecule sequencing detection of N6-methyladenine in microbial reference materials," Nature Communications, (2019) 10:579, 11 pages.

Morgan and Huttenhower, "Meta'omic Analytic Techniques for Studying the Intestinal Microbiome," Gastroenterology, 2014, 146(6):1437-1448.e1.

Morton et al., "Balance Trees Reveal Microbial Niche Differentiation," mSystems (2017) 2:e00162-16, 11 pages.

(56) References Cited

OTHER PUBLICATIONS

Møller et al., "A Scaled Conjugate Gradient Algorithm for Fast Supervised Learning," Neural Networks, 1993, vol. 6, pp. 525-533.

Muyzer, et al., "Profiling of complex microbial populations by denaturing gradient gel electrophoresis analysis of polymerase chain reaction-amplified genes coding for 16S rRNA," Applied and Environmental Microbiology (1993); 59(3): 695-700.

Nelson et al., "Analysis, Optimization and Verification of IlluminaGenerated 16S rRNA Gene Amplicon Surveys," PLoS ONE (2014) 9(4): e94249, 14 pages.

Newman, "Finding community structure in networks using the eigenvectors of matrices," Physical Review E 74.3 (2006): 036104.

Neumann et al., "Stacked Gaussian Process Learning," 2009 Ninth IEEE International Conference on Data Mining, 10 pages.

Nguyen et al., "Multivariate Maximal Correlation Analysis," Proceedings of the 31st International Conference on Machine Learning, Beijing, China, 2014.

Nurk et al., "Assembling Genomes and Mini-Metagenomes from Highly Chimeric Reads," In Lecture Notes in Computer Science, 2013, 158-70.

Peano et al., "An efficient rRNA removal method for RNA sequencing in GC-rich bacteria," Microbial Informatics and Experimentation 2013, 3:1, 11 pages.

Pitta et al., "Temporal dynamics in the ruminal microbiome of dairy cows during the transition period," J. Anim. Sci. 2014, 92:4014-4022.

Poczos et al., "Copula-based Kernel Dependency Measures" Carnegie Mellow University, Research Showcase @ CMU, Proceedings of the 29th International Conference on Machine Learning, 2012, 15 pages.

Probst et al., "Lactic acid fermentation within a cascading approach for biowaste treatment," Applied Microbiology and Biotechnology (2015) 99, 3029-3040.

Rényi, "On measures of dependence," Acta Mathematica Hungarica 10.3-4 (1959): 441-451.

Rosen et al., "Metagenome Fragment Classification Using -Mer Frequency Profiles," Advances in Bioinformatics, 2008, vol. 2008, Article ID 205969, 12 pages.

Sakakibara et al, "Isolation and identification of dieldrin-degrading *Pseudonocardia* sp. strain KSF27 using a soil-charcoal perfusion method with aldrin trans-diol as a structural analog of dieldrin," Biochemical and Biophysical Research Communications, Jul. 2011, vol. 411, Issue 1, pp. 76-81.

Salter et al., "Reagent and laboratory contamination can critically impact sequence-based microbiome analyses," BMC Biology 2014, 12:87, 12 pages.

Schmieder and Edwards, "Fast Identification and Removal of Sequence Contamination from Genomic and Metagenomic Datasets," PLoS ONE (2011) 6(3):e17288, 11 pages.

Sharma et al., "The primary transcriptome of the major human pathogen Helicobacter pylori," Nature (2010) vol. 464, pp. 250-255.

Sharon et al., "A single-molecule long-read survey of the human transcriptome," Nat Biotechnol. Nov. 2013; 31(11): 1009-1014.

Sharon et al., "Time series community genomics analysis reveals rapid shifts in bacterial species, strains, and phage during infant gut colonization," Genome Research, 2013. 23: 111-120.

Simpson et al., "ABySS: A parallel assembler for short read sequence data," Genome Research, 2009, 19:1117-1123.

Simpson et al., "Detecting DNA cytosine methylation using nanopore sequencing," Nature Methods (2017) vol. 14, pp. 407-410.

Sinha et al., "Assessment of variation in microbial community amplicon sequencing by the Microbiome Quality Control (MBQC) project consortium," Nature Biotechnology (2017) 35(11): 1077-1086.

Smola and Schölkopf, "A tutorial on support vector regression," Statistics and Computing, 2004 14: 199-222.

Stewart, R., et al., "Compendium of 4,941 rumen metagenome-assembled genomes for rumen microbiome biology and enzyme discovery," Nature Biotechnology, Aug. 2019, vol. 37, pp. 953-961.

Strous et al., "The binning of metagenomic contigs for microbial physiology of mixed cultures," Frontiers in Microbiology, Dec. 2012, vol. 3, Article 410, 11 pages.

Sunagawa et al., "Metagenomic species profiling using universal phylogenetic marker genes," Nature Methods (2013) vol. 10, pp. 1196-1199.

Sultan et al., "Influence of RNA extraction methods and library selection schemes on RNA-seq data," BMC Genomics 2014, 15:675, 13 pages.

Svartström et al., "Ninety-Nine de Novo Assembled Genomes from the Moose (*Alces alces*) Rumen Microbiome Provide New Insights into Microbial Plant Biomass Degradation," The ISME Journal, 2017, 11(11):2538-2551.

Szekely et al., "Brownian Distance Covariance" The Annals of Applied Statistics, 2009, vol. 3, No. 4, 1236-1265, Doi:10.1214/09-AOAS312.

Szekely et al., "Measuring and Testing Dependence by Correlation of Distances" The Annals of Statistics, 2007, vol. 35, No. 6, 2769-2794, doi:10.1214/009053607000000505.

Tanaka et al., "Protein and polymer analyses up to m/z 100 000 by laser ionization time-of-flight mass spectrometry," Rapid Communications in Mass Spectrometry, 1988, vol. 2, Issue 8, pp. 151-153.

Taskinen et al., "Multivariate nonparametric tests of independence," Journal of the American Statistical Association 100:471 (2005): 916-925.

Tanner et al., "Specific Ribosomal DNA Sequences from Diverse Environmental Settings Correlate with Experimental Contaminants," Applied and Environmental Microbiology, Aug. 1998, vol. 64, No. 8, pp. 3110-3113.

Taylor, K., "Summarizing multiple aspects of model performance in a single diagram," Journal of Geophysical Research Atmospheres, Apr. 16, 2001, vol. 106, No. D7, pp. 7183-7192.

Thoendel et al., "Comparison of Microbial DNA Enrichment Tools for Metagenomie Whole Genome Sequencing," Journal of Microbiological Methods (Aug. 2016), 127: 141-45.

Trapnell et al., "Transcript assembly and quantification by RNA-Seq reveals unannotated transcripts and isoform switching during cell differentiation," Nature Biotechnology 2010, 28(5):511-515.

Truong et al., "MetaPhlAn2 for enhanced metagenomic taxonomic profiling," Nature Methods (2015) vol. 12, pp. 902-903.

Wendisch et al., "Isolation of *Escherichia coli* mRNA and Comparison of Expression Using mRNA and Total RNA on DNA Microarrays," Analytical Biochemistry, vol. 290, Issue 2, Mar. 2001, pp. 205-213.

White et al., "Amplification and Direct Sequencing of Fungal Ribosomal RNA Genes for Phylogenetics," PCR Protocols: A Guide to Methods and Applications, Chapter 38, 1990 Academic Press, pp. 316-322.

Wick et al., "Unicycler: Resolving bacterial genome assemblies from short and long sequencing reads," PLoS Comput Biol (2016) 13(6): e1005595, 22 pages.

Wilks, S.S. "On the Independence of k Sets of Normally Distributed Statistical Variables," Econometrica, vol. 3, No. 3, Jul. 1935, pp. 309-326.

Wiseman et al., "Desorption electrospray ionization mass spectrometry: Imaging drugs and metabolites in tissues," PNAS, Nov. 2008, vol. 105, No. 47, 18120-18125.

Wiseman et al., "Tissue Imaging at Atmospheric Pressure Using Desorption Electrospray Ionization (DESI) Mass Spectrometry," Angew Chem Int Ed Engl. Nov. 6, 2006;45(43):7188-7192.

Ye et al., "Characterization of a Family of Algorithms for Generalized Discriminant Analysis on Undersampled Problems," Journal of Machine Learning Research (2005) 6: 483-502.

Yuan et al., "Long Noncoding RNA Associated With Microvascular Invasion in Hepatocellular Carcinoma Promotes Angiogenesis and Serves as a Predictor for Hepatocellular Carcinoma Patients' Poor Recurrence-Free Survival After Hepatectomy," Hepatology, Dec. 2012, 56(6):2231-41.

Zhang et al., "Detecting Multivariable Correlation with Maximal Information Entropy[J]," Journal of Electronics & Information Technology, Jan. 2015 37(1): 123-129 (with English abstract).

(56) References Cited

OTHER PUBLICATIONS

Zhang et al., "Integrating Multiple 'Omics' Analysis for Microbial Biology: Application and Methodologies," Microbiology, 2009, 156(2):287-301.
Final Office Action in U.S. Appl. No. 15/349,829, dated Aug. 30, 2019.
Final Office Action in U.S. Appl. No. 15/948,965, dated Aug. 30, 2019.
Non-Final Office Action in U.S. Appl. No. 15/349,829 dated Mar. 2, 2020.
Non-Final Office Action in U.S. Appl. No. 15/948,965 dated Mar. 2, 2020.

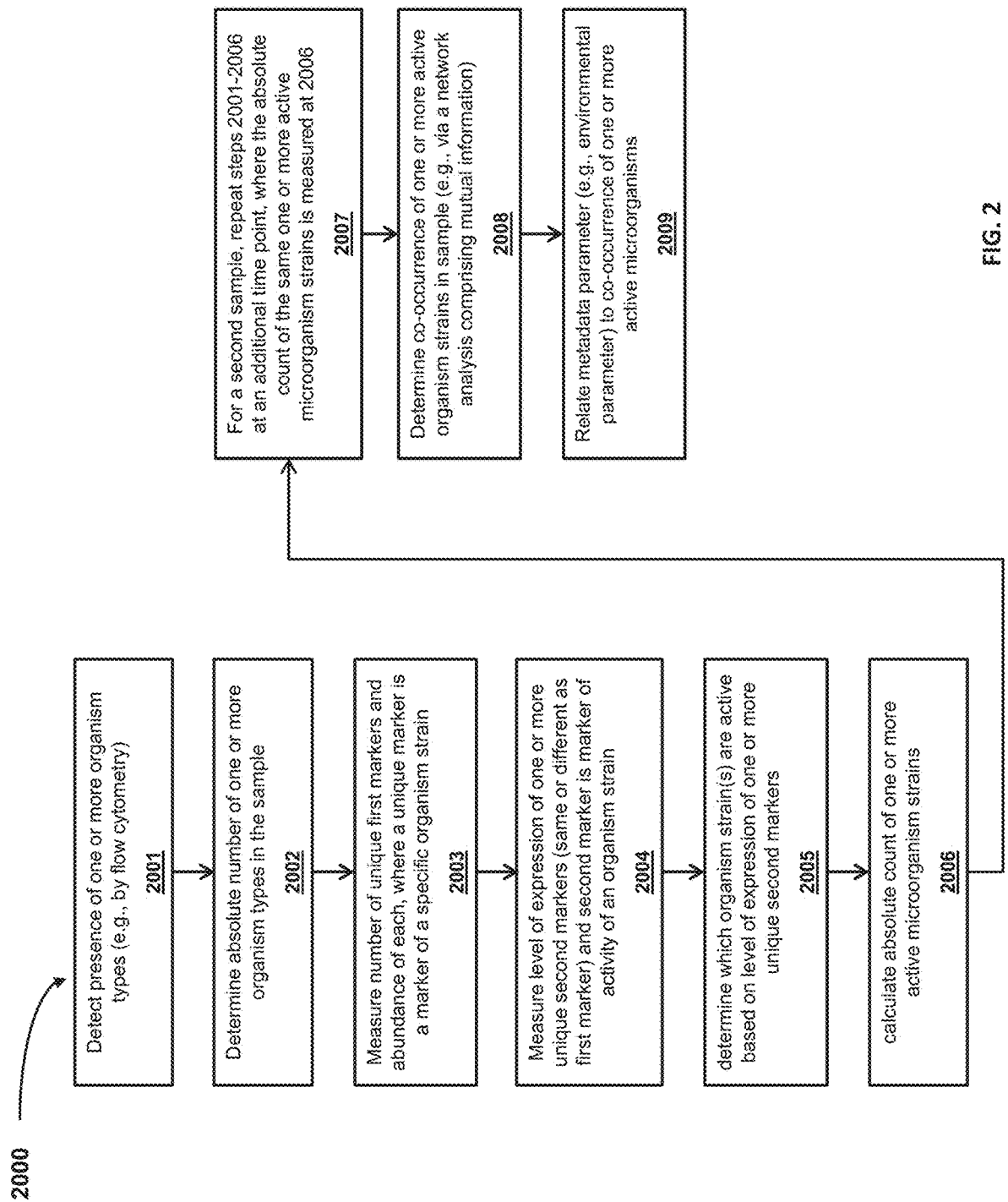

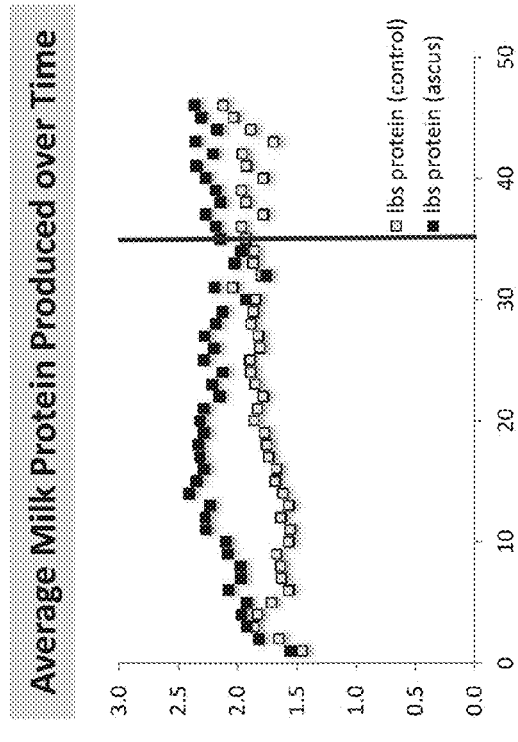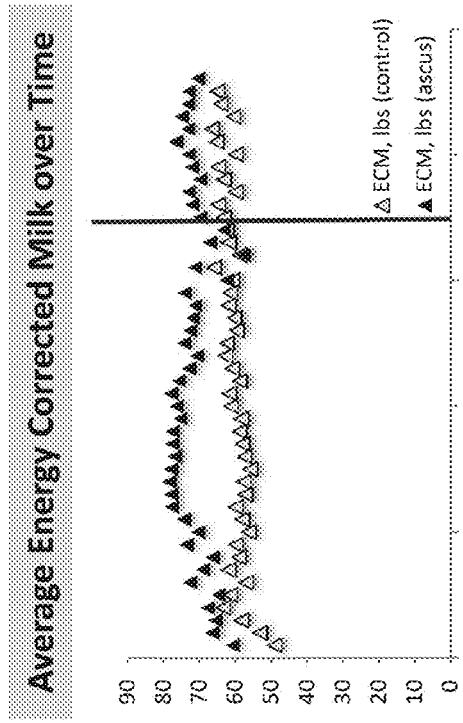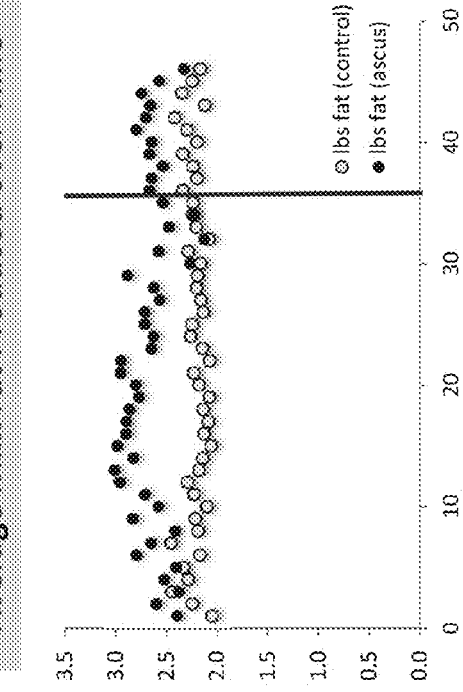
FIG. 8

METHODS, APPARATUSES, AND SYSTEMS FOR MICROORGANISM STRAIN ANALYSIS OF COMPLEX HETEROGENEOUS COMMUNITIES, PREDICTING AND IDENTIFYING FUNCTIONAL RELATIONSHIPS AND INTERACTIONS THEREOF, AND SELECTING AND SYNTHESIZING MICROBIAL ENSEMBLES BASED THEREON

CROSS-REFERENCE TO RELATED APPLICATIONS

This application is a continuation-in-part of International PCT Application No. PCT/US16/39221, entitled "METHODS, APPARATUSES, AND SYSTEMS FOR ANALYZING MICROORGANISM STRAINS FROM COMPLEX HETEROGENEOUS COMMUNITIES, PREDICTING AND IDENTIFYING FUNCTIONAL RELATIONSHIPS AND INTERACTIONS THEREOF, AND SELECTING AND SYNTHESIZING MICROBIAL ENSEMBLES BASED THEREON," which was filed Jun. 24, 2016, now pending, which in turn claims a priority benefit to: (1) U.S. Provisional Application No. 62/184,650, entitled "Methods for Screening Microbial Communities," filed Jun. 25, 2015, and (2) U.S. Provisional Application No. 62/276,142, entitled "Methods for Screening Microbial Communities," filed Jan. 7, 2016; this application is also a continuation-in-part of U.S. patent application Ser. No. 15/349,829, filed on Nov. 11, 2016, which is a continuation of U.S. patent application Ser. No. 15/217,575, filed Jul. 22, 2016, now pending, which is a continuation of International PCT Application No. PCT/US16/39221, filed Jun. 24, 2016, now pending, which in turn claims a priority benefit to U.S. Provisional Application No. 62/184,650, filed Jun. 25, 2015, and U.S. Provisional Application No. 62/276,142, filed Jan. 7, 2016, this application is also a continuation-in-part of U.S. patent application Ser. No. 15/217,575, filed Jul. 22, 2016, now pending, which is a continuation of International PCT Application No. PCT/US16/39221, filed Jun. 24, 2016, now pending, which in turn claims a priority benefit to U.S. Provisional Application No. 62/184,650, filed Jun. 25, 2015, and U.S. Provisional Application No. 62/276,142, filed Jan. 7, 2016; this application also claims a priority benefit to U.S. Provisional Application No. 62/276,142, filed Jan. 7, 2016; the entirety of each of the aforementioned applications is herein expressly incorporated by reference.

This application may contain material that is subject to copyright, mask work, and/or other intellectual property protection. The respective owners of such intellectual property have no objection to the facsimile reproduction of the disclosure by anyone as it appears in published Patent Office file/records, but otherwise reserve all rights.

BACKGROUND

Microorganisms coexist in nature as communities and engage in a variety of interactions, resulting in both collaboration and competition between individual community members. Advances in microbial ecology have revealed high levels of species diversity and complexity in most communities. Microorganisms are ubiquitous in the environment, inhabiting a wide array of ecosystems within the biosphere. Individual microorganisms and their respective communities play unique roles in environments such as marine sites (both deep sea and marine surfaces), soil, and animal tissues, including human tissue.

SUMMARY

In one aspect of the disclosure, a method for identifying active microorganisms from a plurality of samples, analyzing identified microorganisms with at least one metadata, and creating an ensemble of microorganism based on the analysis is disclosed. Embodiments of the method include determining the absolute cell count of one or more active microorganism strains in a sample, wherein the one or more active microorganism strains is present in a microbial community in the sample. The one or more microorganism strains is a subtaxon of a microorganism type. Samples used in the methods provided herein can be of any environmental origin. For example, in one embodiment, the sample is from animal, soil (e.g., bulk soil or rhizosphere), air, saltwater, freshwater, wastewater sludge, sediment, oil, plant, an agricultural product, plant, or an extreme environment. In another embodiment, the animal sample is a blood, tissue, tooth, perspiration, fingernail, skin, hair, feces, urine, semen, mucus, saliva, gastrointestinal tract, rumen, muscle, brain, tissue, or organ sample. In one embodiment, a method for determining the absolute cell count of one or more active microorganism strains is provided.

According to some embodiments, a method of forming a bioensemble of active microorganism strains configured to alter a property in a target biological environment is provided. Such methods can comprise obtaining at least two samples (or sample sets) sharing at least one common environmental parameter (such as sample type, sample time, sample location, sample source type, etc.) and detecting the presence of a plurality of microorganism types in each sample. Then the absolute number of cells of each detected microorganism type of the plurality of microorganism types in each sample is determined (e.g., by way of non-limiting example, the dyeing procedures, cell sorting/FACS, etc., as discussed herein), and measuring a number of unique first markers in each sample, and quantity thereof, each unique first marker being a marker of a microorganism strain of a detected microorganism type. Certain detected microorganisms/strains can be omitted from further processing/analysis, depending on the embodiment, for example, for efficiency. The absolute cell count of some or each microorganism strain present in each sample is determined based on the number of each detected microorganism types in that sample and the number of unique first markers and quantity thereof in that sample. At least one unique second marker, indicative of activity (e.g., metabolic activity) is measured for each microorganism strain to determine active microorganism strains in each sample, and a set or list of active microorganisms strains and their respective absolute cell counts for each of the at least two samples is generated. The active microorganisms strains and respective absolute cell counts for each of the at least two samples with at least one measured metadata for each of the at least two samples are analyzed to identify relationships between each active microorganism strain and at least one measured metadata, measured metadata for each sample, and/or measured metadata for a sample set or the sample sets. Based on the analysis, a plurality of active microorganism strains are selected and combined with a carrier medium to form a bioensemble of active microorganisms, the bioensemble of active microorganisms configured to alter at least one property (that corresponds to the at least one metadata) of a target biological environment when the bioensemble is introduced into that target biological environment. Depending on the embodiment, the metadata can be one or more environmental parameter(s), and can be the same or relatively similar across samples or sample sets, have different values across different samples or sample sets. For example, the metadata for dairy cows could include feed and milk output, and the feed metadata value could be the same (i.e., the cows are fed the same feed) while the milk output could vary (i.e., the sample from one cow or set of samples from a particular herd of cows has an average milk output that is different from milk output corresponding to a sample from a second cow or sample set for a separate herd of cows).

According to some embodiments of the disclosure, methods for analyzing microbial communities are provided. Such methods can comprise obtaining at least two samples (or data for at least two samples), each sample including a heterogeneous microbial community, and detecting the presence of a plurality of microorganism types in each sample. An absolute number of cells of each detected microorganism type of the plurality of microorganism types in each sample is then determined (e.g., via FACS or other methods as discussed herein). A number of unique first markers in each sample, and quantity thereof, are measured, each unique first marker being a marker of a microorganism strain of a detected microorganism type. A value (activity, concentration, expression, etc.) of one or more unique second markers is measured, a unique second marker indicative of activity (e.g., metabolic activity) of a particular microorganism strain of a detected microorganism type, and the activity of each detected microorganism strain is determined based on the measured value of the one or more unique second markers (e.g., based on the value exceeding a specified set threshold). The proportional presence and/or respective ratios of each active detected microorganism strain are determined (e.g., based on the relative quantity of strains for each microorganism type, the number of each microorganism type/respective absolute cell counts per type, the absolute cell count of each detected active microorganism strain, first unique marker values, second unique marker values, etc.). Then each of the active detected microorganism strains (or a subset thereof) of the at least two samples are analyzed to identifying relationships and the strengths thereof between each active detected microorganism strain and the other active detected microorganism strains, and between each active detected microorganism strain and at least one measured metadata. The identified relationships are then displayed or otherwise output, and can be utilized for generation of a bioensemble. In some embodiments, only relationships that exceed a certain strength or weight are displayed. As detailed throughout the disclosure, bioensembles can be configured such that, when introduced into a target environment, a bioensemble can change or alter a property of the target environment (and especially a property that is related to the measured metadata).

According to some embodiments of the disclosure, methods comprise detecting the presence of a plurality of microorganism types in a plurality of samples and determining the absolute number of cells of each of the detected microorganism types in each sample. A number of unique first markers in each sample, and quantity thereof, can be measured, a unique first marker being a marker of a microorganism strain. A value or level of one or more unique second markers is measured, a unique second marker being indicative of metabolic activity of a particular microorganism strain. Based on measured value or level, an activity of each of the detected microorganism strains for each sample is determined or defined (e.g., based on the measured value or level exceeding a specified threshold). A weighted or cell-adjusted value of each active detected microorganism strain in the sample is determined (the weighted or cell-adjusted value is not relative abundance). In some implementations, the weighted or cell-adjusted value is the absolute cell count for a strain relative to the sum of all absolute cell counts for all strains.

Each of the detected active microorganism strains of each sample (or sample sets) is analyzed. The analysis can include identifying relationship and the strengths thereof between each detected active microorganism strain having a weighted value and every other active microorganism strain having a weighted value, and each active microorganism strain having a weighted value and one or more measured metadata.

The identified relationships (an in some embodiments, related data such as weighted values and strengths) can then be displayed or otherwise output, and can be utilized for generation of a synthetic ensemble. In some embodiments, the identified relationships for each metadata are displayed or output. In some embodiments, the displayed or output relationships identify or are configured to facilitate identification of one or more microbial strains responsible for a disease. In some embodiments, the displayed or output relationships identify or are configured to facilitate identification of one or more microbial strains to treat a disease or disorder.

In some embodiments, only relationships that exceed a certain strength or weight (e.g., exceeding a specified threshold or base value) are displayed or output. As detailed throughout the disclosure, synthetic ensembles can be configured such that, when introduced into a target environment, a synthetic ensemble can change or alter a property of the target environment (and especially a property that is related to the measured metadata). In some implementations, the above method can be used to form a synthetic ensemble of active microorganism strains configured to alter a property in a biological environment, and is based on two or more sample sets each having a plurality of environmental parameters, at least one parameter of the plurality of environmental parameters being a common environmental parameter that is similar between the two or more sample sets and at least one environmental parameter being a different environmental parameter that is different between each of the two or more sample sets. In some implementations, each sample set includes at least one sample comprising a heterogeneous microbial community obtained from a biological sample source. In some implementations, at least one of the active microorganism strains is a subtaxon of one or more microorganism types.

In some embodiments of the disclosure, the one or more microorganism types are one or more bacteria (e.g., *Mycoplasma*, coccus, *Bacillus, Rickettsia*, spirillum), fungi (e.g., filamentous fungi, yeast), nematodes, protozoans, archaea, algae, dinoflagellates, viruses (e.g., bacteriophages), viroids and/or a combination thereof. In one embodiment, the one or more microorganism strains is one or more bacteria (e.g., *Mycoplasma*, coccus, *Bacillus, Rickettsia*, spirillum), fungi (e.g., filamentous fungi, yeast), nematodes, protozoans, archaea, algae, dinoflagellates, viruses (e.g., bacteriophages), viroids and/or a combination thereof. In a further embodiment, the one or more microorganism strains is one or more fungal species or fungal sub-species. In a further embodiment, the one or more microorganism strains is one or more bacterial species or bacterial sub-species. In even a further embodiment, the sample is a ruminal sample. In some embodiments, the ruminal sample is from cattle. In even a further embodiment, the sample is a gastrointestinal sample. In some embodiments, the gastrointestinal sample is from a pig or chicken.

In some embodiments, the methods include determining the absolute cell count of one or more active microorganism strains in a sample, the presence of one or more microorganism types in the sample is detected and the absolute number of each of the one or more microorganism types in the sample is determined. A number of unique first markers is measured along with the quantity or abundance of each of the unique first markers. As described herein, a unique first marker is a marker of a unique microorganism strain. Activity is then assessed at the protein or RNA level by measuring the level of expression of one or more unique second markers. The unique second marker is the same or different as the first unique marker, and is a marker of activity of an organism strain. Based on the level of expression of one or more of the unique second markers, a determination is made which (if any) one or more microorganism strains are active. In one embodiment, a microorganism strain is considered active if it expresses the second unique marker at threshold level, or at a percentage above a threshold level. The absolute cell count of the one or more active microorganism strains is determined based upon the quantity of the one or more first markers of the one or more active microorganism strains and the absolute number of the microorganism types from which the one or more microorganism strains is a subtaxon.

In one embodiment, determining the number of each of the one or more organism types in the sample comprises subjecting the sample or a portion thereof to nucleic acid sequencing, centrifugation, optical microscopy, fluorescence microscopy, staining, mass spectrometry, microfluidics, quantitative polymerase chain reaction (qPCR) or flow cytometry.

In one embodiment, measuring the number of first unique markers in the sample comprises measuring the number of unique genomic DNA markers. In another embodiment, measuring the number of first unique markers in the sample comprises measuring the number of unique RNA markers. In another embodiment, measuring the number of unique first markers in the sample comprises measuring the number of unique protein markers. In another embodiment, measuring the number of unique first markers in the sample comprises measuring the number of unique metabolite markers. In a further embodiment, measuring the number of unique metabolite markers in the sample comprises measuring the number of unique carbohydrate markers, unique lipid markers or a combination thereof.

In another embodiment, measuring the number of unique first markers, and quantity thereof, comprises subjecting genomic DNA from the sample to a high throughput sequencing reaction. The measurement of a unique first marker in one embodiment, comprises a marker specific reaction, e.g., with primers specific for the unique first marker. In another embodiment, a metagenomic approach.

In one embodiment, measuring the level of expression of one or more unique second markers comprises subjecting RNA (e.g., miRNA, tRNA, rRNA, and/or mRNA) in the sample to expression analysis. In a further embodiment, the gene expression analysis comprises a sequencing reaction. In yet another embodiment, the RNA expression analysis comprises a quantitative polymerase chain reaction (qPCR), metatranscriptome sequencing, and/or transcriptome sequencing.

In some embodiments, measuring the number of second unique markers in the sample comprises measuring the number of unique protein markers. In some embodiments, measuring the number of unique second markers in the sample comprises measuring the number of unique metabolite markers. In some embodiments, measuring the number of unique metabolite markers in the sample comprises measuring the number of unique carbohydrate markers. In some embodiments, measuring the number of unique metabolite markers in the sample comprises measuring the number of unique lipid markers. In some embodiments, the absolute cell count of the one or more microorganism strains is measured in a plurality of samples. In further embodiments, the plurality of samples is obtained from the same environment or a similar environment. In some embodiments, the plurality of samples are obtained at a plurality of time points.

In some embodiments, measuring the level of one or more unique second markers comprises subjecting the sample or a portion thereof to mass spectrometry analysis. In some embodiments, measuring the level of expression of one more unique second markers comprises subjecting the sample or a portion thereof to metaribosome profiling and/or ribosome profiling.

In another aspect of the disclosure, a method for determining the absolute cell count of one or more active microorganism strains is determined in a plurality of samples, and the absolute cell count levels are related to one or more metadata (e.g., environmental) parameters. Relating the absolute cell count levels to one or more metadata parameters comprises in one embodiment, a co-occurrence measurement, a mutual information measurement, a linkage analysis, and/or the like. The one or more metadata parameters in one embodiment, is the presence of a second active microorganism strain. Accordingly, the absolute cell count values are used in one embodiment of this method to determine the co-occurrence of the one or more active microorganism strains in a microbial community with an environmental parameter. In another embodiment, the absolute cell count levels of the one or more active microorganism strains is related to an environmental parameter such as feed conditions, pH, nutrients or temperature of the environment from which the microbial community is obtained.

In this aspect, the absolute cell count of one or more active microorganism strains is related to one or more environmental parameters. The environmental parameter can be a parameter of the sample itself, e.g., pH, temperature, amount of protein in the sample, the presence of other microbes in the community. In one embodiment, the parameter is a particular genomic sequence of the host from which the sample is obtained (e.g., a particular genetic mutation). Alternatively, the environmental parameter is a parameter that affects a change in the identity of a microbial community (i.e., where the "identity" of a microbial community is characterized by the type of microorganism strains and/or number of particular microorganism strains in a community), or is affected by a change in the identity of a microbial community. For example, an environmental parameter in one embodiment, is the food intake of an animal or the amount of milk (or the protein or fat content of the milk) produced by a lactating ruminant. In some embodiments described herein, an environmental parameter is referred to as a metadata parameter.

In one embodiment, determining the co-occurrence of one or more active microorganism strains in the sample comprises creating matrices populated with linkages denoting one or more environmental parameters and active microorganism strain associations.

In one embodiment, determining the co-occurrence of one or more active organism strains and a metadata parameter comprises a network and/or cluster analysis method to measure connectivity of strains within a network, wherein the network is a collection of two or more samples that share a common or similar environmental parameter. In some embodiments, the network analysis and/or network analysis methods comprise one or more of graph theory, species community rules, Eigenvectors/modularity matrix, Gambit of the Group, and/or network measures. In some implementations, network measures include one or more of observation matrices, time-aggregated networks, hierarchical cluster analysis, node-level metrics and/or network level metrics. In some embodiments, node-level metrics include one or more of: degree, strength, betweenness centrality, Eigenvector centrality, page rank, and/or reach. In some embodiments, network level metrics include one or more of density, homophily/assortativity, and/or transitivity.

In some embodiments, network analysis comprises linkage analysis, modularity analysis, robustness measures, betweenness measures, connectivity measures, transitivity measures, centrality measures or a combination thereof. In another embodiment, the cluster analysis method comprises building a connectivity model, subspace model, distribution model, density model, or a centroid model. In another embodiment, the network analysis comprises predictive modeling of network through link mining and prediction, collective classification, link-based clustering, relational similarity, or a combination thereof. In another embodiment, the network analysis comprises mutual information, maximal information coefficient calculations, or other nonparametric methods between variables to establish connectivity. In another embodiment, the network analysis comprises differential equation based modeling of populations. In another embodiment, the network analysis comprises Lotka-Volterra modeling.

Based on the analysis, strain relationships can be displayed or otherwise output, and/or one or more active relevant strains are identified for including in a microbial ensemble.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 2 shows a general process flow determining the co-occurrence of one or more active microorganism strains in a sample or sample with one or more metadata (environmental) parameters, according to some embodiments.

FIG. 8 shows the results of a field trial in which dairy cows were administered a microbial ensemble prepared according to the disclosed methods; FIG. 8A shows the average number of pounds of milk fat produced over time; FIG. 8B shows the average number of pounds of milk protein produced over time; and FIG. 8C shows the average number of pounds of energy corrected milk (ECM) produced over time.

DETAILED DESCRIPTION

Figure 1A:
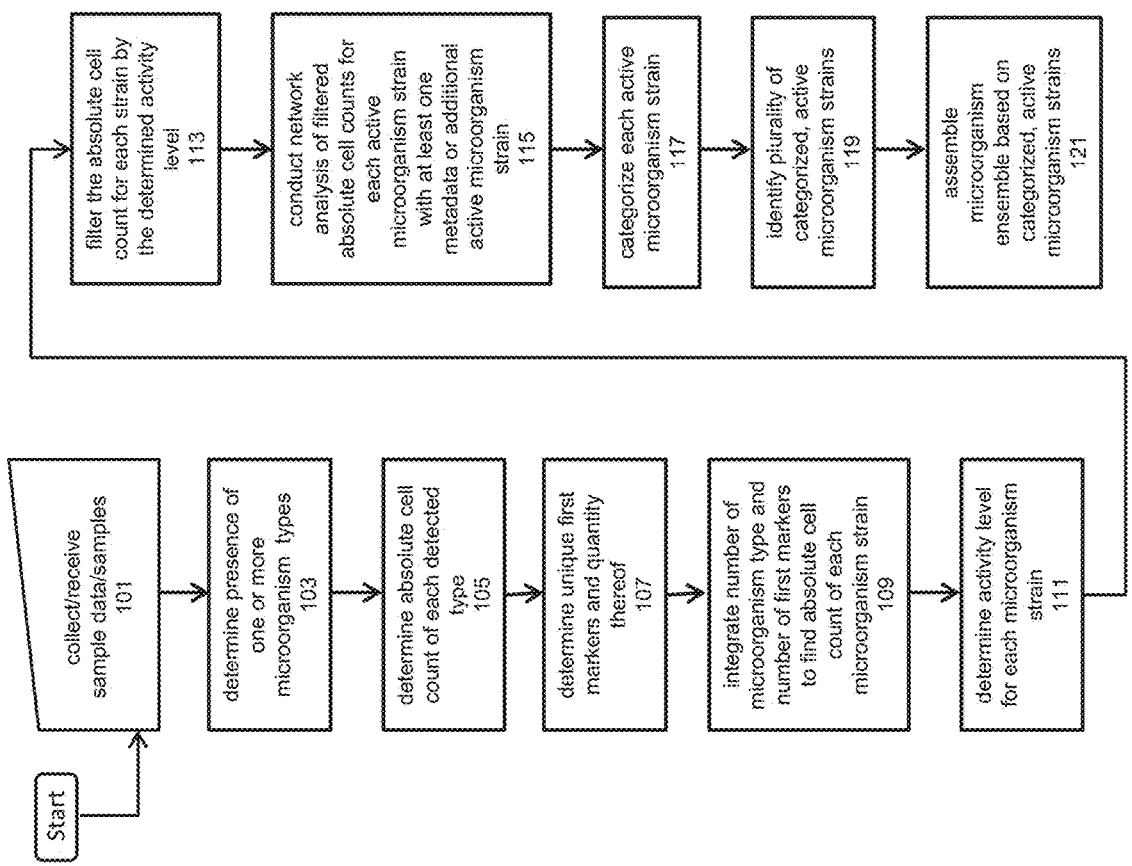
FIG. 1A shows an exemplary high-level process flow for screening and analyzing microorganism strains from complex heterogeneous communities, predicting functional relationships and interactions thereof, and selecting and synthesizing microbial ensembles based thereon, according to some embodiments.

Microbial communities are central to environmental processes in many different types ecosystems as well and the Earth's biogeochemistry, e.g., by cycling nutrients and fixing carbon (Falkowski et al. (1998) Science 281, pp. 237-240, incorporated by reference herein in its entirety for all purposes). However, because of community complexity and the lack of culturability of most of the members of any given microbial community, the molecular and ecological details as well as influencing factors of these processes are still poorly understood.

Microbial communities differ in qualitative and quantitative composition and each microbial community is unique, and its composition depends on the given ecosystem and/or environment in which it resides. The absolute cell count of microbial community members is subject to changes of the environment in which the community resides, as well as the physiological and metabolic changes caused by the microorganisms (e.g., cell division, protein expression, etc.). Changes in environmental parameters and/or the quantity of one active microorganism within a community can have far-reaching effects on the other microorganisms of the community and on the ecosystem and/or environment in which the community is found. To understand, predict, and react to changes in these microbial communities, it is necessary to identify the active microorganisms in a sample, and the number of the active microorganisms in the respective community. However, to date, the vast majority of studies of microbial community members have focused on the proportions of microorganisms in the particular microbial community, rather than absolute cell count (Segata et al. (2013). Molecular Systems Biology 9, p. 666, incorporated by reference herein in its entirety for all purposes).

Although microbial community compositions can be readily determined for example, via the use of high throughput sequencing approaches, a deeper understanding of how the respective communities are assembled and maintained is needed.

Microorganism communities are involved in critical processes such as biogeochemical cycling of essential elements, e.g., the cycling of carbon, oxygen, nitrogen, sulfur, phosphorus and various metals; and the respective community's structures, interactions and dynamics are critical to the biosphere's existence (Zhou et al. (2015). mBio 6(1): e02288-14. Doi:10.1128/mBio.02288-14, herein incorporated by reference in its entirety for all purposes). Such communities are highly heterogeneous and almost always include complex mixtures of bacteria, viruses, archaea, and other micro-eukaryotes such as fungi. The levels of microbe community heterogeneity in human environments such as the gut and vagina have been linked to diseases such as inflammatory bowel disease and bacterial vaginosis (Nature (2012). Vo. 486, p. 207, herein incorporated by reference in its entirety for all purposes). Notably however, even healthy individuals differ remarkably in the microbes that occupy tissues in such environments (Nature (2012). Vo. 486, p. 207).

As many microbes may be unculturable or otherwise difficult/expensive to culture, cultivation-independent approaches such as nucleic acid sequencing have advanced the understanding of the diversity of various microbial communities. Amplification and sequencing of the small subunit ribosomal RNA (SSU rRNA or 16s rRNA) gene was the foundational approach to the study of microbial diversity in a community, based in part on the gene's universal presence and relatively uniform rate of evolution. Advances in high-throughput methods have led to metagenomics analysis, where entire genomes of microbes are sequenced. Such methods do not require a priori knowledge of the community, enabling the discovery of new microorganism strains. Metagenomics, metatranscriptomics, metaproteomics and metabolomics all enable probing of a community to discern structure and function.

The ability to not only catalog the microorganisms in a community but to decipher which members are active, the number of those organisms, and co-occurrence of a microbial community member(s) with each other and with environmental parameter(s), for example, the co-occurrence of two microbes in a community in response to certain changes in the community's environment, would allow for the understanding of the importance of the respective environmental factor (e.g., climate, nutrients present, environmental pH) has on the identity of microbes within a microbial community (and their respective numbers), as well as the importance of certain community members have on the environment in which the community resides. The present disclosure addresses these and other needs.

As used in this specification, the singular forms "a," "an" and "the" include plural referents unless the context clearly dictates otherwise. Thus, for example, the term "an organism type" is intended to mean a single organism type or multiple organism types. For another example, the term "an environmental parameter" can mean a single environmental parameter or multiple environmental parameters, such that the indefinite article "a" or "an" does not exclude the possibility that more than one of environmental parameter is present, unless the context clearly requires that there is one and only one environmental parameter.

Reference throughout this specification to "one embodiment", "an embodiment", "one aspect", or "an aspect", "one implementation", or "an implementation" means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics can be combined in any suitable manner in one or more embodiments.

As used herein, in particular embodiments, the terms "about" or "approximately" when preceding a numerical value indicates the value plus or minus a range of 10%.

As used herein, "isolate," "isolated," "isolated microbe," and like terms, are intended to mean that the one or more microorganisms has been separated from at least one of the materials with which it is associated in a particular environment (for example soil, water, animal tissue). Thus, an "isolated microbe" does not exist in its naturally occurring environment; rather, it is through the various techniques described herein that the microbe has been removed from its natural setting and placed into a non-naturally occurring state of existence. Thus, the isolated strain may exist as, for example, a biologically pure culture, or as spores (or other forms of the strain) in association with an acceptable carrier.

As used herein, "microbial ensemble" refers to a composition comprising one or more active microbes identified by methods, systems, and/or apparatuses of the present disclosure and that does not naturally exist in a naturally occurring environment and/or at ratios or amounts that do not exist in a nature. For example, a microbial ensemble (also synthetic ensemble or bioensemble) or aggregate could be formed from one or more isolated microbe strains, along with an appropriate medium or carrier. Microbial ensembles can be applied or administered to a target, such as a target environment, population, individual, animal, and/or the like.

The microbial ensembles according to the disclosure are selected from sets, subsets, and/or groupings of active, interrelated individual microbial species, or strains of a species. The relationships and networks, as identified by methods of the disclosure, are grouped and/or linked based on carrying out one or more a common functions, or can be described as participating in, or leading to, or associated with, a recognizable parameter, such as a phenotypic trait of interest (e.g. increased milk production in a ruminant). The groups from which the microbial ensemble is selected, and/or the microbial ensemble itself, can include two or more species, strains of species, or strains of different species, of microbes. In some instances, the microbes coexist can within the groups and/or microbial ensemble symbiotically.

In certain aspects of the disclosure, microbial ensembles are or are based on one or more isolated microbes that exist as isolated and biologically pure cultures. It will be appreciated by one of skill in the art, that an isolated and biologically pure culture of a particular microbe, denotes that said culture is substantially free (within scientific reason) of other living organisms and contains only the individual microbe in question. The culture can contain varying concentrations of said microbe. The present disclosure notes that isolated and biologically pure microbes often "necessarily differ from less pure or impure materials." See, e.g. In re *Bergstrom*, 427 F.2d 1394, (CCPA 1970)(discussing purified prostaglandins), see also, In re *Bergy*, 596 F.2d 952 (CCPA 1979)(discussing purified microbes), see also, *Parke-Davis & Co. v. H. K. Mulford & Co.,* 189 F. 95 (S.D.N.Y. 1911) (Learned Hand discussing purified adrenaline), aff'd in part, rev'd in part, 196 F. 496 (2d Cir. 1912), each of which are incorporated herein by reference. Furthermore, in some aspects, implementation of the disclosure can require certain quantitative measures of the concentration, or purity limitations, that must be achieved for an isolated and biologically pure microbial culture to be used in the disclosed microbial ensembles. The presence of these purity values, in certain embodiments, is a further attribute that distinguishes the microbes identified by the presently disclosed method from those microbes existing in a natural state. See, e.g., *Merck & Co. v. Olin Mathieson Chemical Corp.,* 253 F.2d 156 (4th Cir. 1958) (discussing purity limitations for vitamin B12 produced by microbes), incorporated herein by reference.

As used herein, "carrier", "acceptable carrier", or "pharmaceutical carrier" refers to a diluent, adjuvant, excipient, or vehicle with which is used with or in the microbial ensemble. Such carriers can be sterile liquids, such as water and oils, including those of petroleum, animal, vegetable, or synthetic origin; such as peanut oil, soybean oil, mineral oil, sesame oil, and the like. Water or aqueous solution saline solutions and aqueous dextrose and glycerol solutions are preferably employed as carriers, in some embodiments as injectable solutions. Alternatively, the carrier can be a solid dosage form carrier, including but not limited to one or more of a binder (for compressed pills), a glidant, an encapsulating agent, a flavorant, and a colorant. The choice of carrier can be selected with regard to the intended route of administration and standard pharmaceutical practice. See Hardee and Baggo (1998. Development and Formulation of Veterinary Dosage Forms. 2nd Ed. CRC Press. 504 pg.); E. W. Martin (1970. Remington's Pharmaceutical Sciences. 17th Ed. Mack Pub. Co.); and Blaser et al. (US Publication US20110280840A1), each of which is herein expressly incorporated by reference in their entirety.

The terms "microorganism" and "microbe" are used interchangeably herein and refer to any microorganism that is of the domain Bacteria, Eukarya or Archaea. Microorganism types include without limitation, bacteria (e.g., *Mycoplasma*, coccus, *Bacillus, Rickettsia,* spirillum), fungi (e.g., filamentous fungi, yeast), nematodes, protozoans, archaea, algae, dinoflagellates, viruses (e.g., bacteriophages), viroids and/or a combination thereof. Organism strains are subtaxons of organism types, and can be for example, a species, sub-species, subtype, genetic variant, pathovar or serovar of a particular microorganism.

The term "marker" or "unique marker" as used herein is an indicator of unique microorganism type, microorganism strain or activity of a microorganism strain. A marker can be measured in biological samples and includes without limitation, a nucleic acid-based marker such as a ribosomal RNA gene, a peptide- or protein-based marker, and/or a metabolite or other small molecule marker.

The term "metabolite" as used herein is an intermediate or product of metabolism. A metabolite in one embodiment is a small molecule. Metabolites have various functions, including in fuel, structural, signaling, stimulatory and inhibitory effects on enzymes, as a cofactor to an enzyme, in defense, and in interactions with other organisms (such as pigments, odorants and pheromones). A primary metabolite is directly involved in normal growth, development and reproduction. A secondary metabolite is not directly involved in these processes but usually has an important ecological function. Examples of metabolites include but are not limited to antibiotics and pigments such as resins and terpenes, etc. Some antibiotics use primary metabolites as precursors, such as actinomycin which is created from the primary metabolite, tryptophan. Metabolites, as used herein, include small, hydrophilic carbohydrates; large, hydrophobic lipids and complex natural compounds.

In one aspect of the disclosure, a method for identifying relationships between a plurality of microorganism strains and one or more metadata and/or parameters is disclosed. As illustrated in FIG. 1A, samples and/or sample data for at least two samples is received from at least two sample sources 101, and for each sample, the presence of one or more microorganism types is determined 103. The number (cell count) of each detected microorganism type of the one or more microorganism types in each sample is determined 105, and a number of unique first markers in each sample, and quantity thereof is determined 107, each unique first marker being a marker of a microorganism strain. The number of each microorganism type and the number of the first markers is integrated to yield the absolute cell count of each microorganism strain present in each sample 109, and an activity level for each microorganism strain in each sample is determined 111 based on a measure of at least one unique second marker for each microorganism strain exceeding a specified threshold, a microorganism strain being identified as active if the measure of at least one unique second marker for that strain exceeds the corresponding threshold. The absolute cell count of each microorganism strain is then filtered by the determined activity to provide a set or list of active microorganisms strains and their respective absolute cell counts for each of the at least two samples 113. A network analysis of the set or list of filtered absolute cell counts of active microorganisms strains for each of the at least two samples with at least one measured metadata or additional active microorganism strain is conducted 115, the network analysis including determining maximal information coefficient scores between each active microorganism strain and every other active microorganism strain and determining maximal information coefficient scores between each active microorganism strain and the at least one measured metadata or additional active microorganism strain. The active microorganism strains can then be categorized based on function, predicted function and/or chemistry 117, and a plurality of active microorganism strains identified and output based on the categorization 119. In some embodiments, the method further comprises assembling an active microorganism ensemble from the identified plurality of microorganism strains 121, the microorganism ensemble configured to, when applied to a target, alter a property corresponding to the at least one measured metadata. The method can further comprise identifying at least one pathogen based on the output plurality of identified active microorganism strains (see Example 4 for additional detail). In some embodiments, the plurality of active microorganism strains can be utilized to assemble an active microorganism ensemble that is configured to, when applied to a target, address the at least one identified pathogen and/or treat a symptom associated with the at least one identified pathogen.

In one aspect of the disclosure, a method for determining the absolute cell count of one or more active microorganism strains in a sample or plurality of samples is provided, wherein the one or more active microorganism strains are present in a microbial community in the sample. The one or more microorganism strains is a subtaxon of one or more organism types (see method 1000 at FIG. 1B). For each sample, the presence of one or more microorganism types in the sample is detected (1001). The absolute number of each of the one or more organism types in the sample is determined (1002). The number of unique first markers is measured along with the quantity of each of the unique first markers (1003). As described herein, a unique first marker is a marker of a unique microorganism strain. Activity is then assessed at the protein and/or RNA level by measuring the level of expression of one or more unique second markers (1004). The unique second marker can be the same or different as the first unique marker, and is a marker of activity of an organism strain. Based on the level of expression of one or more of the unique second markers, a determination is made which (if any) microorganism strains are active (1005). A microorganism strain is considered active if it expresses the second unique marker at a particular level, or above a threshold level (1005), for example, at least about 10%, at least about 20%, at least about 30% or at least about 40% above a threshold level (it is to be understood that the various thresholds can be determined based on the particular application and/or implementation, for example, thresholds can vary by sample source(s), such as a particular species, sample origin location, metadata of interest, environment, etc.). The absolute cell count of the one or more active microorganism strains can be determined based upon the quantity of the one or more first markers of the one or more active microorganism strains and the absolute number of the organism types from which the one or more microorganism strains is a subtaxon.

Some embodiments of the disclosure can be configured for analyzing microbial communities. As illustrated by FIG. 1C, data for two or more samples (and/or sample sets) are obtained (1051), each sample including a heterogeneous microbial community, and a plurality of microorganism types is detected in each sample (1053). An absolute number of cells of each detected microorganism type of the plurality of microorganism types in each sample is then determined (1055), e.g., via FACS or other methods as discussed herein. Unique first markers in each sample, and quantity thereof, are measured (1057), each unique first marker being a marker of a microorganism strain of a detected microorganism type. A value (activity, concentration, expression, etc.) of one or more unique second markers is measured (1059), a unique second marker indicative of activity (e.g., metabolic activity) of a particular microorganism strain of a detected microorganism type, and the activity of each detected microorganism strain is determined (1061), based on the measured value of the one or more unique second markers (e.g., based on the value exceeding a specified set threshold). The respective ratios of each active detected microorganism strain in each sample are determined (1063), e.g., based on the respective absolute cell counts, values, etc. For example, in an illustrative implementation, cells form horse fecal samples were stained and counted. Then, total nucleic acids were isolated from each sample. The elutate was split into two parts and enzymatically purified to obtain either purified DNA or purified RNA. Purified RNA was stabilized through enzymatic conversion of RNA to cDNA. Illumina sequencing libraries were prepared for both DNA and cDNA using PCR to attach the appropriate barcodes and adapter regions, and to amplify the marker region. After sequencing, raw sequencing reads were quality trimmed and merged, and the total population of microbial strains was identified. Sequencing libraries derived from DNA samples were mapped back to the total population of microbial strains in order to identity which strains were present in each sample, and quantify the number of reads for each strain in each sample. The quantified read list was then integrated with the absolute cell count data to determine the absolute number of cells of each strain. After integrating the cell count data, reads from the cDNA libraries were mapped back to the strains in each sample in order to determine which strains were active in each sample. Inactive strains were removed from the output to generate a list of the respective ratios of each active detected microorganism strain in each sample.

Then each of the active detected microorganism strains (or a subset thereof) of the at least two samples are analyzed to identify relationships and the strengths thereof (1065) between and among each active detected microorganism strain and the other active detected microorganism strains, and between each active detected microorganism strain and at least one measured metadata. The identified relationships are then displayed or otherwise output (1067), e.g., on a graphical display/interface (see, e.g., FIG. 1D), and can be utilized for generation of a bioensemble (1069). In some embodiments, the display/output of relationships can be limited such that only relationships that exceed a certain strength or weight are displayed (1066a, 1066b).

Microbial ensembles according to the disclosure can be selected from sets, subsets, and/or groupings of active, interrelated individual microbial species, or strains of a species. The relationships and networks, as identified by methods of the disclosure, are grouped and/or linked based on carrying out one or more a common functions, or can be described as participating in, or leading to, or associated with, a recognizable parameter, such as a phenotypic trait of interest (e.g. increased milk production in a ruminant). In FIG. 1D, the Louvain community detection method was used to identify groups associated with dairy cow-relevant metadata parameters. Each node represents a specific rumen microorganism strain or a metadata parameter. The links between nodes represent significant relationships. Unconnected nodes are irrelevant microorganisms. Each colored "bubble" represents a group detected by the Louvain analysis. This grouping allows for prediction of the functionality of strains based on the groups they fall into.

Some embodiments of the disclosure are configured to leverage mutual information to rank the importance of native microbial strains residing in the gastrointestinal tract of the animal to specific animal traits. The maximal information coefficient (MIC) is calculated for all microorganisms and the desired animal trait. Relationships are scored on a scale of 0 to 1, with 1 representing a strong relationship between the microbial strain and animal trait and 0 representing no relationship. A cut-off based on this score is used to define useful and non-useful microorganisms with respect to the improvement of specific traits. FIGS. 1E and 1F depict examples of MIC score distributions for rumen microbial strains that share a relationship with milk fat efficiency. Here, the point where the curve shifts from exponential to linear (~0.45-0.5 for bacteria, and ~0.3 for fungi) represents the cut off between useful and non-useful microorganism strains. FIGS. 1G and 1H depict examples of MIC score distributions for rumen microbial strains that share a relationship with dairy efficiency. The point where the curve shifts from exponential to linear (~0.45-0.5 for bacteria, and ~0.25 for fungi) represents the cut off between useful and non-useful microorganism strains.

As provided in FIG. 2, in another aspect of the disclosure, the absolute cell count of one or more active microorganisms is determined in a plurality of samples, and the absolute cell count is related to a metadata (environmental parameter) (2001-2009). A plurality of samples are subjected to analysis for the absolute cell count of one or more active microorganism strains, wherein the one or more active microorganism strains is considered active if an activity measurement is at a threshold level or above a threshold level in at least one of the plurality of samples (2001-2006). The absolute cell count of the one or more active microorganism strains is then related to a metadata parameter of the particular implementation and/or application (2009).

In one embodiment, the plurality of samples is collected over time from the same environmental source (e.g., the same animal over a time course). In another embodiment, the plurality of samples is from a plurality of environmental sources (e.g., different animals). In one embodiment, the environmental parameter is the absolute cell count of a second active microorganism strain. In a further embodiment, the absolute cell count values of the one or more active microorganism strains is used to determine the co-occurrence of the one or more active microorganism strains, with a second active microorganism strain of the microbial community. In a further embodiment, a second environmental parameter is related to the absolute cell count of the one or more active microorganism strains and/or the absolute cell count of the second environmental strain.

Aspects of the disclosed embodiments are discussed throughout the disclosure.

The samples for use with the methods provided herein importantly can be of any type that includes a microbial community. For example, samples for use with the methods provided herein encompass without limitation, an animal sample (e.g., mammal, reptile, bird), soil, air, water (e.g., marine, freshwater, wastewater sludge), sediment, oil, plant, agricultural product, plant, soil (e.g., rhizosphere) and extreme environmental sample (e.g., acid mine drainage, hydrothermal systems). In the case of marine or freshwater samples, the sample can be from the surface of the body of water, or any depth of the body water, e.g., a deep sea sample. The water sample, in one embodiment, is an ocean, river or lake sample.

The animal sample in one embodiment is a body fluid. In another embodiment, the animal sample is a tissue sample. Non-limiting animal samples include tooth, perspiration, fingernail, skin, hair, feces, urine, semen, mucus, saliva, gastrointestinal tract. The animal sample can be, for example, a human, primate, bovine, porcine, canine, feline, rodent (e.g., mouse or rat), or bird sample. In one embodiment, the bird sample comprises a sample from one or more chickens. In another embodiment, the sample is a human sample. The human microbiome comprises the collection of microorganisms found on the surface and deep layers of skin, in mammary glands, saliva, oral mucosa, conjunctiva and gastrointestinal tract. The microorganisms found in the microbiome include bacteria, fungi, protozoa, viruses and archaea. Different parts of the body exhibit varying diversity of microorganisms. The quantity and type of microorganisms may signal a healthy or diseased state for an individual. The number of bacteria taxa are in the thousands, and viruses may be as abundant. The bacterial composition for a given site on a body varies from person to person, not only in type, but also in abundance or quantity.

In another embodiment, the sample is a ruminal sample. Ruminants such as cattle rely upon diverse microbial communities to digest their feed. These animals have evolved to use feed with poor nutritive value by having a modified upper digestive tract (reticulorumen or rumen) where feed is held while it is fermented by a community of anaerobic microbes. The rumen microbial community is very dense, with about $3 \times 10^{10}$ microbial cells per milliliter. Anaerobic fermenting microbes dominate in the rumen. The rumen microbial community includes members of all three domains of life: Bacteria, Archaea, and Eukarya. Ruminal fermentation products are required by their respective hosts for body maintenance and growth, as well as milk production (van Houtert (1993). Anim. Feed Sci. Technol. 43, pp. 189-225; Bauman et al. (2011). Annu. Rev. Nutr. 31, pp. 299-319; each incorporated by reference in its entirety for all purposes). Moreover, milk yield and composition has been reported to be associated with ruminal microbial communities (Sandri et al. (2014). Animal 8, pp. 572-579; Palmonari et al. (2010). J. Dairy Sci. 93, pp. 279-287; each incorporated by reference in its entirety for all purposes). Ruminal samples, in one embodiment, are collected via the process described in Jewell et al. (2015). Appl. Environ. Microbiol. 81, pp. 4697-4710, incorporated by reference herein in its entirety for all purposes.

In another embodiment, the sample is a soil sample (e.g., bulk soil or rhizosphere sample). It has been estimated that 1 gram of soil contains tens of thousands of bacterial taxa, and up to 1 billion bacteria cells as well as about 200 million fungal hyphae (Wagg et al. (2010). Proc Natl. Acad. Sci. USA 111, pp. 5266-5270, incorporated by reference in its entirety for all purposes). Bacteria, actinomycetes, fungi, algae, protozoa and viruses are all found in soil. Soil microorganism community diversity has been implicated in the structure and fertility of the soil microenvironment, nutrient acquisition by plants, plant diversity and growth, as well as the cycling of resources between above- and below-ground communities. Accordingly, assessing the microbial contents of a soil sample over time and the co-occurrence of active microorganisms (as well as the number of the active microorganisms) provides insight into microorganisms associated with an environmental metadata parameter such as nutrient acquisition and/or plant diversity.

The soil sample in one embodiment is a rhizosphere sample, i.e., the narrow region of soil that is directly influenced by root secretions and associated soil microorganisms. The rhizosphere is a densely populated area in which elevated microbial activities have been observed and plant roots interact with soil microorganisms through the exchange of nutrients and growth factors (San Miguel et al. (2014). Appl. Microbiol. Biotechnol. DOI 10.1007/s00253-014-5545-6, incorporated by reference in its entirety for all purposes). As plants secrete many compounds into the rhizosphere, analysis of the organism types in the rhizosphere may be useful in determining features of the plants which grow therein.

In another embodiment, the sample is a marine or freshwater sample. Ocean water contains up to one million microorganisms per milliliter and several thousand microbial types. These numbers may be an order of magnitude higher in coastal waters with their higher productivity and higher load of organic matter and nutrients. Marine microorganisms are crucial for the functioning of marine ecosystems; maintaining the balance between produced and fixed carbon dioxide; production of more than 50% of the oxygen on Earth through marine phototrophic microorganisms such as *Cyanobacteria*, diatoms and pico- and nanophytoplankton; providing novel bioactive compounds and metabolic pathways; ensuring a sustainable supply of seafood products by occupying the critical bottom trophic level in marine foodwebs. Organisms found in the marine environment include viruses, bacteria, archaea and some eukarya. Marine viruses may play a significant role in controlling populations of marine bacteria through viral lysis. Marine bacteria are important as a food source for other small microorganisms as well as being producers of organic matter. Archaea found throughout the water column in the ocean are pelagic Archaea and their abundance rivals that of marine bacteria.

In another embodiment, the sample comprises a sample from an extreme environment, i.e., an environment that harbors conditions that are detrimental to most life on Earth. Organisms that thrive in extreme environments are called extremophiles. Though the domain Archaea contains well-known examples of extremophiles, the domain bacteria can also have representatives of these microorganisms. Extremophiles include: acidophiles which grow at pH levels of 3 or below; alkaliphiles which grow at pH levels of 9 or above; anaerobes such as *Spinoloricus Cinzia* which does not require oxygen for growth; cryptoendoliths which live in microscopic spaces within rocks, fissures, aquifers and faults filled with groundwater in the deep subsurface; halophiles which grow in about at least 0.2M concentration of salt; hyperthermophiles which thrive at high temperatures (about 80-122° C.) such as found in hydrothermal systems; hypoliths which live underneath rocks in cold deserts; lithoautotrophs such as *Nitrosomonas europaea* which derive energy from reduced mineral compounds like pyrites and are active in geochemical cycling; metallotolerant organisms which tolerate high levels of dissolved heavy metals such as copper, cadmium, arsenic and zinc; oligotrophs which grow in nutritionally limited environments; osmophiles which grow in environments with a high sugar concentration; piezophiles (or barophiles) which thrive at high pressures such as found deep in the ocean or underground; psychrophiles/cryophiles which survive, grow and/or reproduce at temperatures of about −15° C. or lower; radioresistant organisms which are resistant to high levels of ionizing radiation; thermophiles which thrive at temperatures between 45-122° C.; xerophiles which can grow in extremely dry conditions. Polyextremophiles are organisms that qualify as extremophiles under more than one category and include thermoacidophiles (prefer temperatures of 70-80° C. and pH between 2 and 3). The Crenarchaeota group of Archaea includes the thermoacidophiles.

The sample can include microorganisms from one or more domains. For example, in one embodiment, the sample comprises a heterogeneous population of bacteria and/or fungi (also referred to herein as bacterial or fungal strains).

In the methods provided herein for determining the presence and absolute cell count of one or more microorganisms in a sample, for example the absolute cell count of one or more microorganisms in a plurality of samples collected from the same or different environments, and/or over multiple time points, the one or more microorganisms can be of any type. For example, the one or more microorganisms can be from the domain Bacteria, Archaea, Eukarya, or a combination thereof. Bacteria and Archaea are prokaryotic, having a very simple cell structure with no internal organelles. Bacteria can be classified into gram positive/no outer membrane, gram negative/outer membrane present and ungrouped phyla. Archaea constitute a domain or kingdom of single-celled microorganisms. Although visually similar to bacteria, archaea possess genes and several metabolic pathways that are more closely related to those of eukaryotes, notably the enzymes involved in transcription and translation. Other aspects of archaeal biochemistry are unique, such as the presence of ether lipids in their cell membranes. The Archaea are divided into four recognized phyla: Thaumarchaeota, Aigarchaeota, Crenarchaeota and Korarchaeota.

The domain of Eukarya comprises eukaryotic organisms, which are defined by membrane-bound organelles, such as the nucleus. Protozoa are unicellular eukaryotic organisms. All multicellular organisms are eukaryotes, including animals, plants and fungi. The eukaryotes have been classified into four kingdoms: Protista, Plantae, Fungi and Animalia. However, several alternative classifications exist. Another classification divides Eukarya into six kingdoms: Excavata (various flagellate protozoa); amoebozoa (lobose amoeboids and slime filamentous fungi); Opisthokonta (animals, fungi, choanoflagellates); Rhizaria (Foraminifera, Radiolaria, and various other amoeboid protozoa); Chromalveolata (Stramenopiles (brown algae, diatoms), Haptophyta, Cryptophyta (or cryptomonads), and Alveolata); Archaeplastida/Primoplantae (Land plants, green algae, red algae, and glaucophytes).

Within the domain of Eukarya, fungi are microorganisms that are predominant in microbial communities. Fungi include microorganisms such as yeasts and filamentous fungi as well as the familiar mushrooms. Fungal cells have cell walls that contain glucans and chitin, a unique feature of these organisms. The fungi form a single group of related organisms, named the Eumycota that share a common ancestor. The kingdom Fungi has been estimated at 1.5 million to 5 million species, with about 5% of these having been formally classified. The cells of most fungi grow as tubular, elongated, and filamentous structures called hyphae, which may contain multiple nuclei. Some species grow as unicellular yeasts that reproduce by budding or binary fission. The major phyla (sometimes called divisions) of fungi have been classified mainly on the basis of characteristics of their sexual reproductive structures. Currently, seven phyla are proposed: Microsporidia, Chytridiomycota, Blastocladi omycota, Neocallimastigomycota, Glomeromycota, Ascomycota, and Basidiomycota.

Microorganisms for detection and quantification by the methods described herein can also be viruses. A virus is a small infectious agent that replicates only inside the living cells of other organisms. Viruses can infect all types of life forms in the domains of Eukarya, Bacteria and Archaea. Virus particles (known as virions) consist of two or three parts: (i) the genetic material which can be either DNA or RNA; (ii) a protein coat that protects these genes; and in some cases (iii) an envelope of lipids that surrounds the protein coat when they are outside a cell. Seven orders have been established for viruses: the Caudovirales, Herpesvirales, Ligamenvirales, Mononegavirales, Nidovirales, Picornavirales, and Tymovirales. Viral genomes may be single-stranded (ss) or double-stranded (ds), RNA or DNA, and may or may not use reverse transcriptase (RT). In addition, ssRNA viruses may be either sense (+) or antisense (−). This classification places viruses into seven groups: I: dsDNA viruses (such as Adenoviruses, Herpesviruses, Poxviruses); II: (+) ssDNA viruses (such as Parvoviruses); III: dsRNA viruses (such as Reoviruses); IV: (+)ssRNA viruses (such as Picornaviruses, Togaviruses); V: (−)ssRNA viruses (such as Orthomyxoviruses, Rhabdoviruses); VI: (+)ssRNA-RT viruses with DNA intermediate in life-cycle (such as Retroviruses); VII: dsDNA-RT viruses (such as Hepadnaviruses).

Microorganisms for detection and quantification by the methods described herein can also be viroids. Viroids are the smallest infectious pathogens known, consisting solely of short strands of circular, single-stranded RNA without protein coats. They are mostly plant pathogens, some of which are of economical importance. Viroid genomes are extremely small in size, ranging from about 246 to about 467 nucleobases.

Figure 1B:
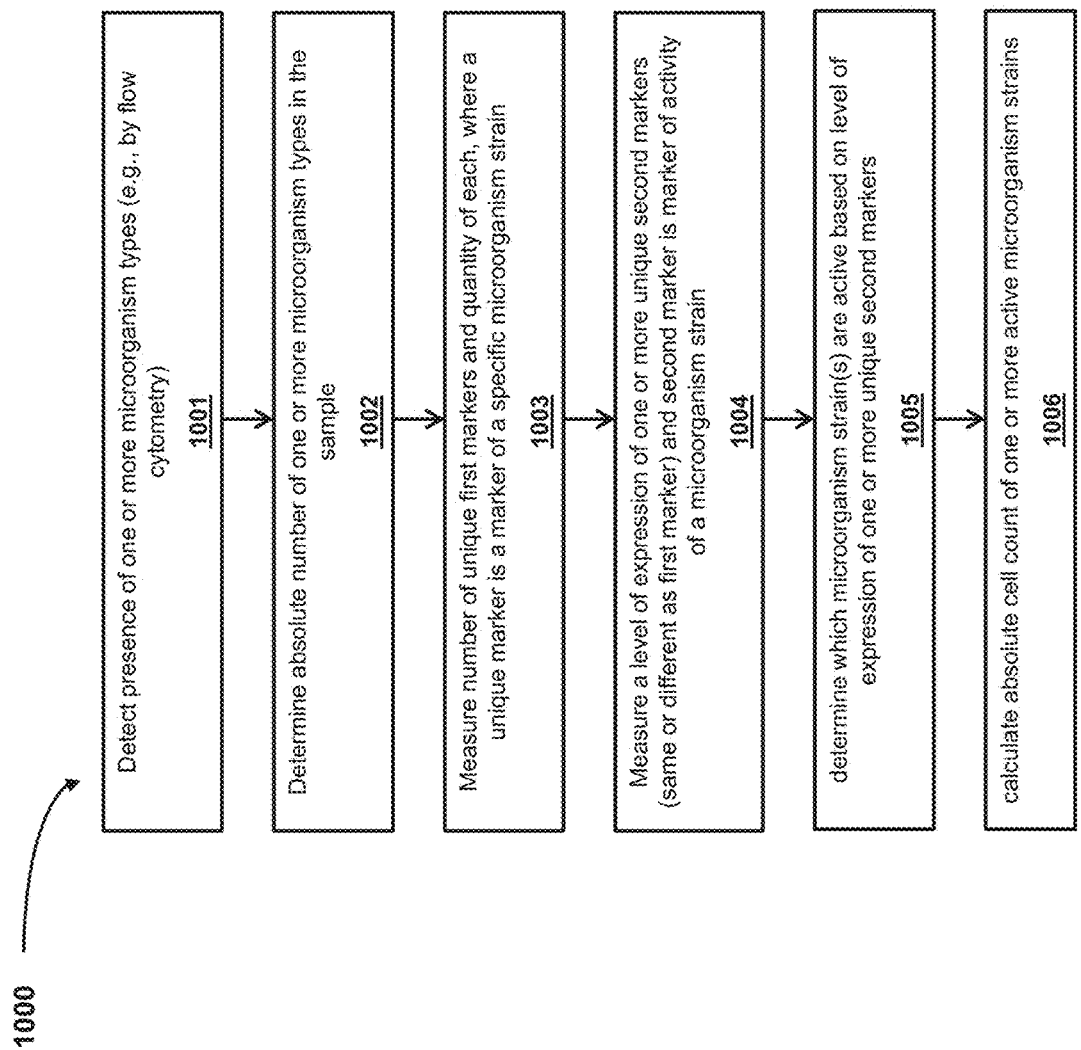
FIG. 1B shows a general process flow for determining the absolute cell count of one or more active microorganism strains, according to some embodiments.
Figure 1C:
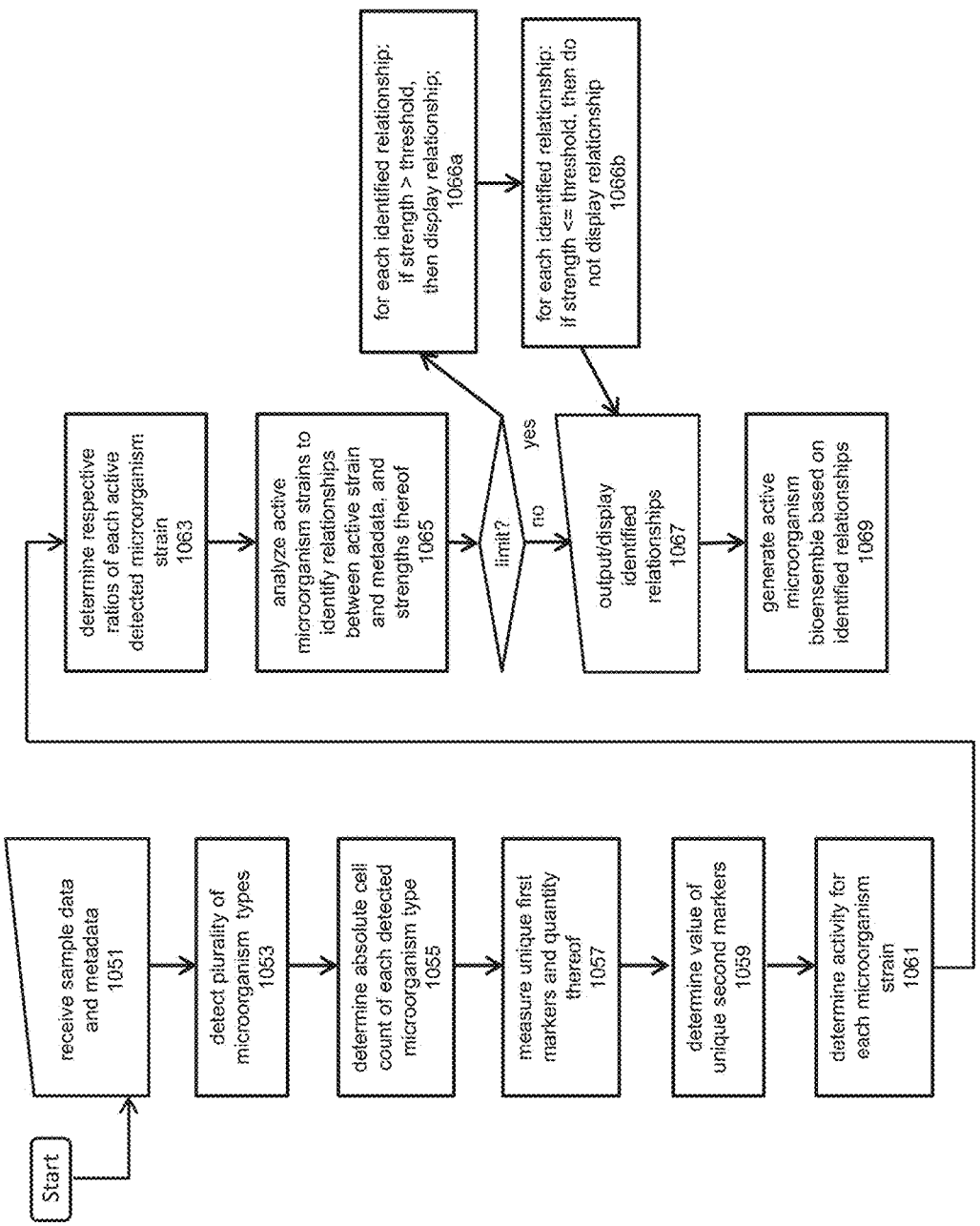
FIG. 1C shows a process flow for microbial community analysis, type/strain-metadata relationship determination, display, and bioensemble generation, according to some embodiments.
Figure 1D:
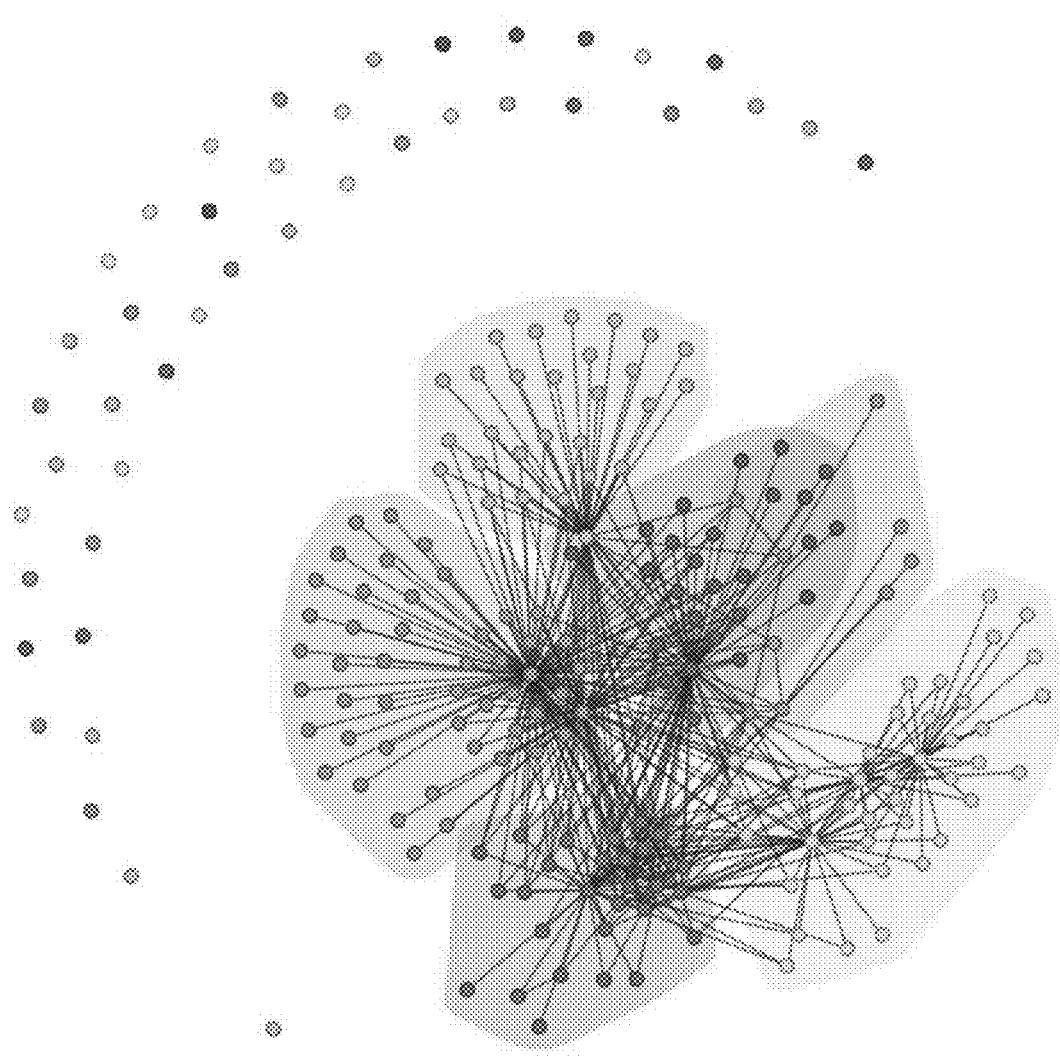
FIG. 1D illustrates exemplary visual output of analyzed strains and relationships, according to some embodiments.
Figure 1E:
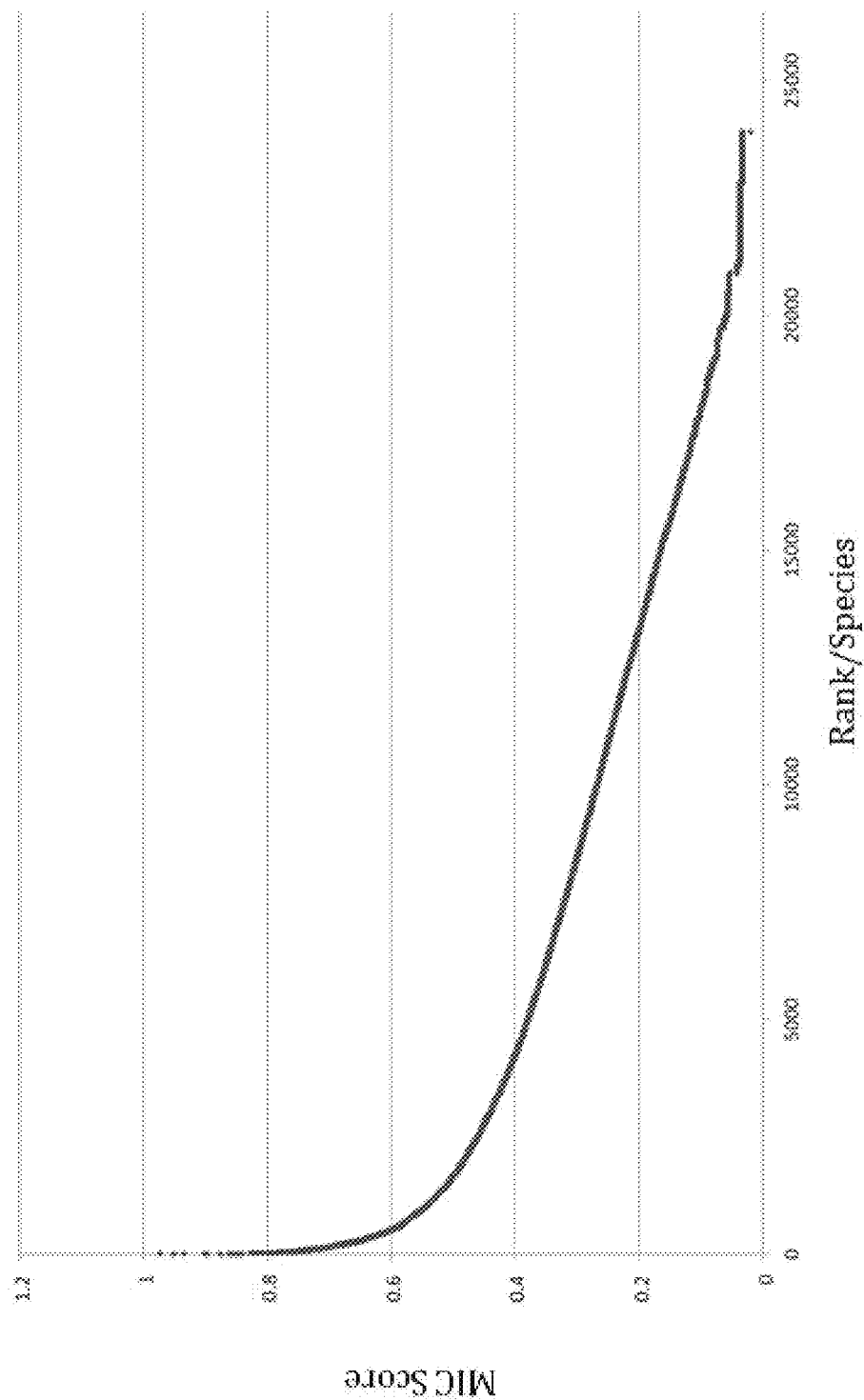
FIG. 1E illustrates MIC Score Distribution for Rumen Bacteria and Milk Fat Efficiency, according to some embodiments.
Figure 1F:
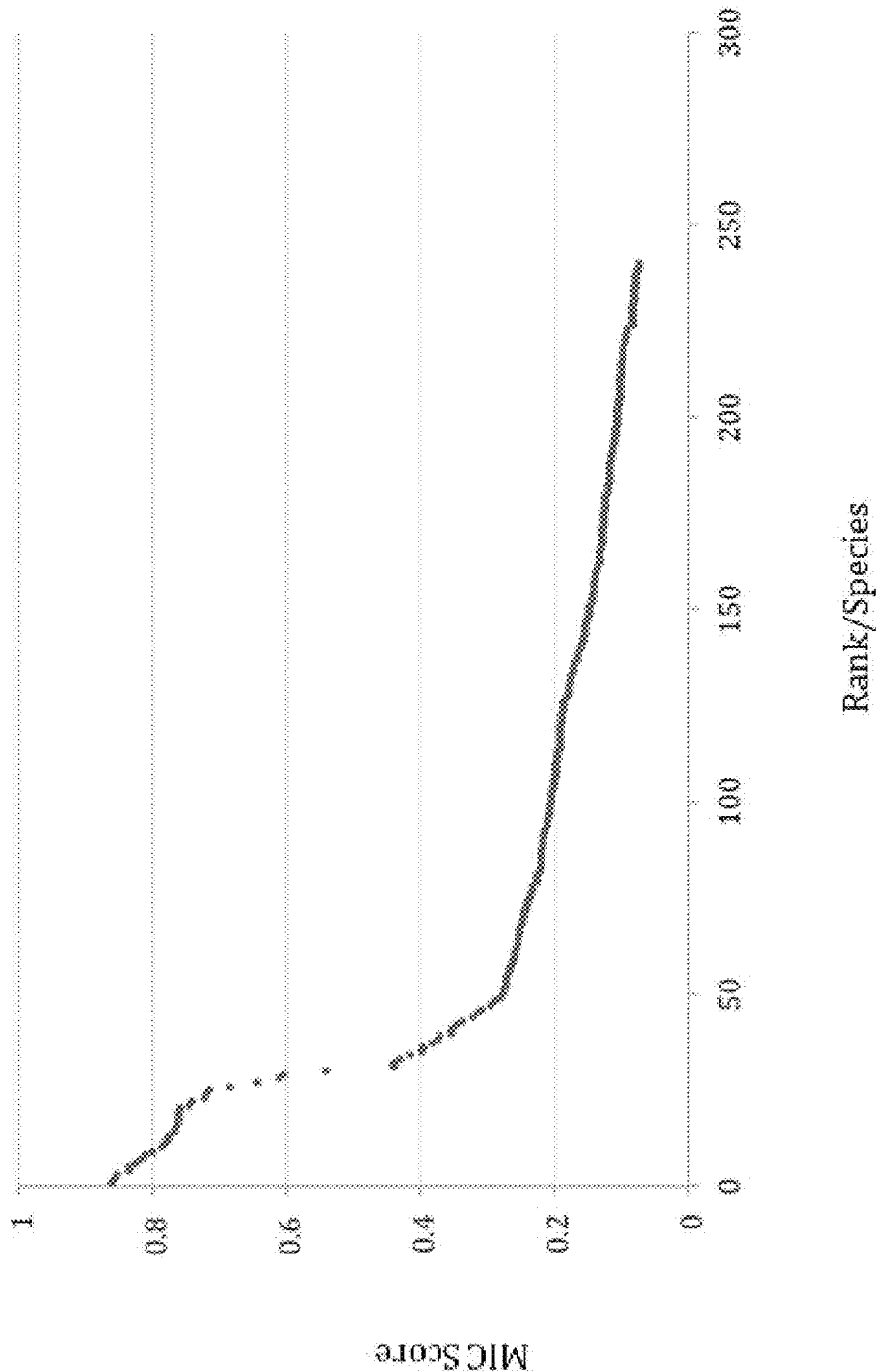
FIG. 1F illustrates MIC Score Distribution for Rumen Fungi and Milk Fat Efficiency, according to some embodiments.
Figure 1G:
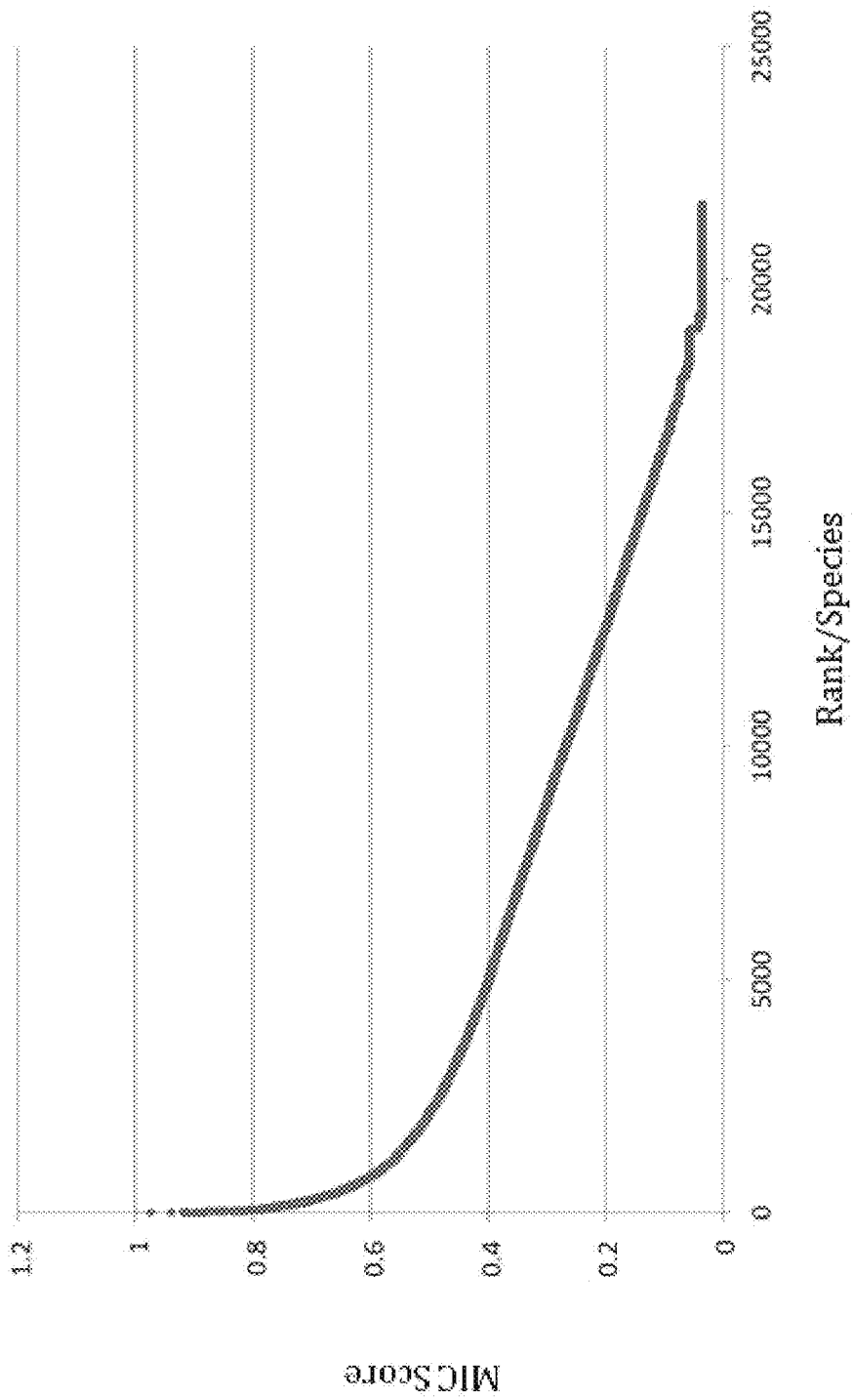
FIG. 1G illustrates MIC Score Distribution for Rumen Bacteria and Dairy Efficiency, according to some embodiments.
Figure 1H:
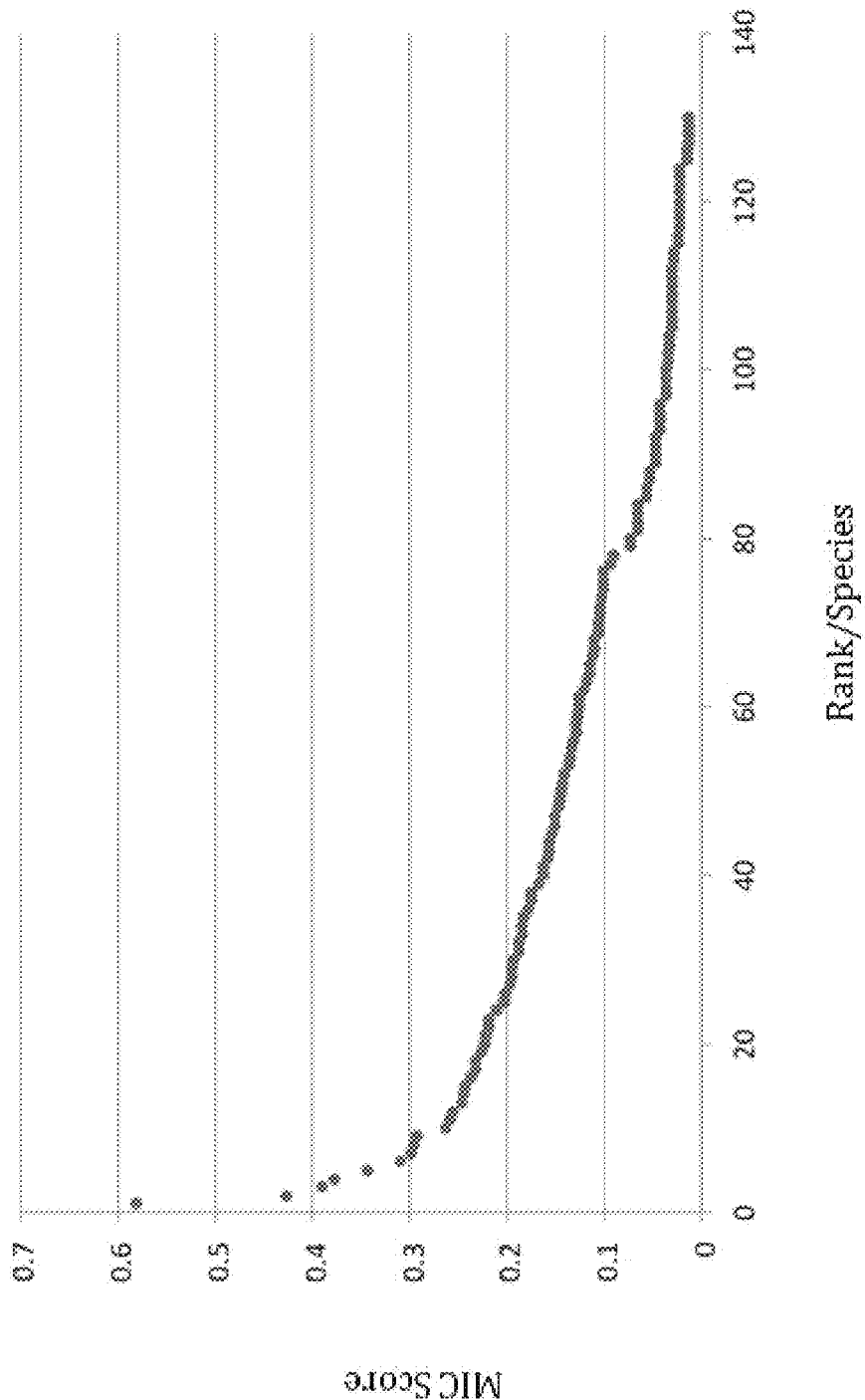
FIG. 1H illustrates MIC Score Distribution for Rumen Fungi and Dairy Efficiency, according to some embodiments.

According to the methods provided herein, a sample is processed to detect the presence of one or more microorganism types in the sample (FIG. 1B, 1001; FIG. 2, 2001). The absolute number of one or more microorganism organism type in the sample is determined (FIG. 1B, 1002; FIG. 2, 2002). The determination of the presence of the one or more organism types and the absolute number of at least one organism type can be conducted in parallel or serially. For example, in the case of a sample comprising a microbial community comprising bacteria (i.e., one microorganism type) and fungi (i.e., a second microorganism type), the user in one embodiment detects the presence of one or both of the organism types in the sample (FIG. 1B, 1001; FIG. 2, 2001). The user, in a further embodiment, determines the absolute number of at least one organism type in the sample—in the case of this example, the number of bacteria, fungi or combination thereof, in the sample (FIG. 1B, 1002; FIG. 2, 2002).

In one embodiment, the sample, or a portion thereof is subjected to flow cytometry (FC) analysis to detect the presence and/or number of one or more microorganism types (FIG. 1B, 1001, 1002; FIG. 2, 2001, 2002). In one flow cytometer embodiment, individual microbial cells pass through an illumination zone, at a rate of at least about $300*s^{-1}$, or at least about $500*s^{-1}$, or at least about $1000*s^{-1}$. However, one of ordinary skill in the art will recognize that this rate can vary depending on the type of instrument is employed. Detectors which are gated electronically measure the magnitude of a pulse representing the extent of light scattered. The magnitudes of these pulses are sorted electronically into "bins" or "channels," permitting the display of histograms of the number of cells possessing a certain quantitative property (e.g., cell staining property, diameter, cell membrane) versus the channel number. Such analysis allows for the determination of the number of cells in each "bin" which in embodiments described herein is an "microorganism type" bin, e.g., a bacteria, fungi, nematode, protozoan, archaea, algae, dinoflagellate, virus, viroid, etc.

In one embodiment, a sample is stained with one or more fluorescent dyes wherein a fluorescent dye is specific to a particular microorganism type, to enable detection via a flow cytometer or some other detection and quantification method that harnesses fluorescence, such as fluorescence microscopy. The method can provide quantification of the number of cells and/or cell volume of a given organism type in a sample. In a further embodiment, as described herein, flow cytometry is harnessed to determine the presence and quantity of a unique first marker and/or unique second marker of the organism type, such as enzyme expression, cell surface protein expression, etc. Two- or three-variable histograms or contour plots of, for example, light scattering versus fluorescence from a cell membrane stain (versus fluorescence from a protein stain or DNA stain) can also be generated, and thus an impression may be gained of the distribution of a variety of properties of interest among the cells in the population as a whole. A number of displays of such multiparameter flow cytometric data are in common use and are amenable for use with the methods described herein.

In one embodiment of processing the sample to detect the presence and number of one or more microorganism types, a microscopy assay is employed (FIG. 1B, 1001, 1002). In one embodiment, the microscopy is optical microscopy, where visible light and a system of lenses are used to magnify images of small samples. Digital images can be captured by a charge-couple device (CCD) camera. Other microscopic techniques include, but are not limited to, scanning electron microscopy and transmission electron microscopy. Microorganism types are visualized and quantified according to the aspects provided herein.

In another embodiment of the disclosure, in order to detect the presence and number of one or more microorganism types, each sample, or a portion thereof is subjected to fluorescence microscopy. Different fluorescent dyes can be used to directly stain cells in samples and to quantify total cell counts using an epifluorescence microscope as well as flow cytometry, described above. Useful dyes to quantify microorganisms include but are not limited to acridine orange (AO), 4,6-di-amino-2 phenylindole (DAPI) and 5-cyano-2,3 Dytolyl Tetrazolium Chloride (CTC). Viable cells can be estimated by a viability staining method such as the LIVE/DEAD® Bacterial Viability Kit (Bac-Light™) which contains two nucleic acid stains: the green-fluorescent SYTO 9™ dye penetrates all membranes and the red-fluorescent propidium iodide (PI) dye penetrates cells with damaged membranes. Therefore, cells with compromised membranes will stain red, whereas cells with undamaged membranes will stain green. Fluorescent in situ hybridization (FISH) extends epifluorescence microscopy, allowing for the fast detection and enumeration of specific organisms. FISH uses fluorescent labelled oligonucleotides probes (usually 15-25 basepairs) which bind specifically to organism DNA in the sample, allowing the visualization of the cells using an epifluorescence or confocal laser scanning microscope (CLSM). Catalyzed reporter deposition fluorescence in situ hybridization (CARD-FISH) improves upon the FISH method by using oligonucleotide probes labelled with a horse radish peroxidase (HRP) to amplify the intensity of the signal obtained from the microorganisms being studied. FISH can be combined with other techniques to characterize microorganism communities. One combined technique is high affinity peptide nucleic acid (PNA)-FISH, where the probe has an enhanced capability to penetrate through the Extracellular Polymeric Substance (EPS) matrix. Another example is LIVE/DEAD-FISH which combines the cell viability kit with FISH and has been used to assess the efficiency of disinfection in drinking water distribution systems.

In another embodiment, each sample, or a portion thereof is subjected to Raman micro-spectroscopy in order to determine the presence of a microorganism type and the absolute number of at least one microorganism type (FIG. 1B, 1001-1002; FIG. 2, 2001-2002). Raman micro-spectroscopy is a non-destructive and label-free technology capable of detecting and measuring a single cell Raman spectrum (SCRS). A typical SCRS provides an intrinsic biochemical "fingerprint" of a single cell. A SCRS contains rich information of the biomolecules within it, including nucleic acids, proteins, carbohydrates and lipids, which enables characterization of different cell species, physiological changes and cell phenotypes. Raman microscopy examines the scattering of laser light by the chemical bonds of different cell biomarkers. A SCRS is a sum of the spectra of all the biomolecules in one single cell, indicating a cell's phenotypic profile. Cellular phenotypes, as a consequence of gene expression, usually reflect genotypes. Thus, under identical growth conditions, different microorganism types give distinct SCRS corresponding to differences in their genotypes and can thus be identified by their Raman spectra.

In yet another embodiment, the sample, or a portion thereof is subjected to centrifugation in order to determine the presence of a microorganism type and the number of at least one microorganism type (FIG. 1B, 1001-1002; FIG. 2, 2001-2002). This process sediments a heterogeneous mixture by using the centrifugal force created by a centrifuge. More dense components of the mixture migrate away from the axis of the centrifuge, while less dense components of the mixture migrate towards the axis. Centrifugation can allow fractionation of samples into cytoplasmic, membrane and extracellular portions. It can also be used to determine localization information for biological molecules of interest. Additionally, centrifugation can be used to fractionate total microbial community DNA. Different prokaryotic groups differ in their guanine-plus-cytosine (G+C) content of DNA, so density-gradient centrifugation based on G+C content is a method to differentiate organism types and the number of cells associated with each type. The technique generates a fractionated profile of the entire community DNA and indicates abundance of DNA as a function of G+C content. The total community DNA is physically separated into highly purified fractions, each representing a different G+C content that can be analyzed by additional molecular techniques such as denaturing gradient gel electrophoresis (DGGE)/amplified ribosomal DNA restriction analysis (AR-DRA) (see discussion herein) to assess total microbial community diversity and the presence/quantity of one or more microorganism types.

In another embodiment, the sample, or a portion thereof is subjected to staining in order to determine the presence of a microorganism type and the number of at least one microorganism type (FIG. 1B, 1001-1002; FIG. 2, 2001-2002). Stains and dyes can be used to visualize biological tissues, cells or organelles within cells. Staining can be used in conjunction with microscopy, flow cytometry or gel electrophoresis to visualize or mark cells or biological molecules that are unique to different microorganism types. In vivo staining is the process of dyeing living tissues, whereas in vitro staining involves dyeing cells or structures that have been removed from their biological context. Examples of specific staining techniques for use with the methods described herein include, but are not limited to: gram staining to determine gram status of bacteria, endospore staining to identify the presence of endospores, Ziehl-Neelsen staining, haematoxylin and eosin staining to examine thin sections of tissue, papanicolaou staining to examine cell samples from various bodily secretions, periodic acid-Schiff staining of carbohydrates, Masson's trichome employing a three-color staining protocol to distinguish cells from the surrounding connective tissue, Romanowsky stains (or common variants that include Wright's stain, Jenner's stain, May-Grunwald stain, Leishman stain and Giemsa stain) to examine blood or bone marrow samples, silver staining to reveal proteins and DNA, Sudan staining for lipids and Conklin's staining to detect true endospores. Common biological stains include acridine orange for cell cycle determination; bismarck brown for acid mucins; carmine for glycogen; carmine alum for nuclei; Coomassie blue for proteins; Cresyl violet for the acidic components of the neuronal cytoplasm; Crystal violet for cell walls; DAPI for nuclei; eosin for cytoplasmic material, cell membranes, some extracellular structures and red blood cells; ethidium bromide for DNA; acid fuchsine for collagen, smooth muscle or mitochondria; haematoxylin for nuclei; Hoechst stains for DNA; iodine for starch; malachite green for bacteria in the Gimenez staining technique and for spores; methyl green for chromatin; methylene blue for animal cells; neutral red for Nissl substance; Nile blue for nuclei; Nile red for lipohilic entities; osmium tetroxide for lipids; rhodamine is used in fluorescence microscopy; safranin for nuclei. Stains are also used in transmission electron microscopy to enhance contrast and include phosphotungstic acid, osmium tetroxide, ruthenium tetroxide, ammonium molybdate, cadmium iodide, carbohydrazide, ferric chloride, hexamine, indium trichloride, lanthanum nitrate, lead acetate, lead citrate, lead(II) nitrate, periodic acid, phosphomolybdic acid, potassium ferricyanide, potassium ferrocyanide, ruthenium red, silver nitrate, silver proteinate, sodium chloroaurate, thallium nitrate, thiosemicarbazide, uranyl acetate, uranyl nitrate, and vanadyl sulfate.

In another embodiment, the sample, or a portion thereof is subjected to mass spectrometry (MS) in order to determine the presence of a microorganism type and the number of at least one microorganism type (FIG. 1B, 1001-1002; FIG. 2, 2001-2002). MS, as discussed below, can also be used to detect the presence and expression of one or more unique markers in a sample (FIG. 1B, 1003-1004; FIG. 2, 2003-2004). MS is used for example, to detect the presence and quantity of protein and/or peptide markers unique to microorganism types and therefore to provide an assessment of the number of the respective microorganism type in the sample. Quantification can be either with stable isotope labelling or label-free. De novo sequencing of peptides can also occur directly from MS/MS spectra or sequence tagging (produce a short tag that can be matched against a database). MS can also reveal post-translational modifications of proteins and identify metabolites. MS can be used in conjunction with chromatographic and other separation techniques (such as gas chromatography, liquid chromatography, capillary electrophoresis, ion mobility) to enhance mass resolution and determination.

In another embodiment, the sample, or a portion thereof is subjected to lipid analysis in order to determine the presence of a microorganism type and the number of at least one microorganism type (FIG. 1B, 1001-1002; FIG. 2, 2001-2002). Fatty acids are present in a relatively constant proportion of the cell biomass, and signature fatty acids exist in microbial cells that can differentiate microorganism types within a community. In one embodiment, fatty acids are extracted by saponification followed by derivatization to give the respective fatty acid methyl esters (FAMEs), which are then analyzed by gas chromatography. The FAME profile in one embodiment is then compared to a reference FAME database to identify the fatty acids and their corresponding microbial signatures by multivariate statistical analyses.

In the aspects of the methods provided herein, the number of unique first makers in the sample, or portion thereof (e.g., sample aliquot) is measured, as well as the quantity of each of the unique first markers (FIG. 1B, 1003; FIG. 2, 2003). A unique marker is a marker of a microorganism strain. It should be understood by one of ordinary skill in the art that depending on the unique marker being probed for and measured, the entire sample need not be analyzed. For example, if the unique marker is unique to bacterial strains, then the fungal portion of the sample need not be analyzed. As described above, in some embodiments, measuring the absolute cell count of one or more organism types in a sample comprises separating the sample by organism type, e.g., via flow cytometry.

Any marker that is unique to an organism strain can be employed herein. For example, markers can include, but are not limited to, small subunit ribosomal RNA genes (16S/18S rDNA), large subunit ribosomal RNA genes (23S/25S/28S rDNA), intercalary 5.8S gene, cytochrome c oxidase, beta-tubulin, elongation factor, RNA polymerase and internal transcribed spacer (ITS).

Ribosomal RNA genes (rDNA), especially the small subunit ribosomal RNA genes, i.e., 18S rRNA genes (18S rDNA) in the case of eukaryotes and 16S rRNA (16S rDNA) in the case of prokaryotes, have been the predominant target for the assessment of organism types and strains in a microbial community. However, the large subunit ribosomal RNA genes, 28S rDNAs, have been also targeted. rDNAs are suitable for taxonomic identification because: (i) they are ubiquitous in all known organisms; (ii) they possess both conserved and variable regions; (iii) there is an exponentially expanding database of their sequences available for comparison. In community analysis of samples, the conserved regions serve as annealing sites for the corresponding universal PCR and/or sequencing primers, whereas the variable regions can be used for phylogenetic differentiation. In addition, the high copy number of rDNA in the cells facilitates detection from environmental samples.

The internal transcribed spacer (ITS), located between the 18S rDNA and 28S rDNA, has also been targeted. The ITS is transcribed but spliced away before assembly of the ribosomes. The ITS region is composed of two highly variable spacers, ITS1 and ITS2, and the intercalary 5.8S gene. This rDNA operon occurs in multiple copies in genomes. Because the ITS region does not code for ribosome components, it is highly variable.

In one embodiment, the unique RNA marker can be an mRNA marker, an siRNA marker or a ribosomal RNA marker.

Protein-coding functional genes can also be used herein as a unique first marker. Such markers include but are not limited to: the recombinase A gene family (bacterial RecA, archaea RadA and RadB, eukaryotic Rad51 and Rad57, phage UvsX); RNA polymerase β subunit (RpoB) gene, which is responsible for transcription initiation and elongation; chaperonins. Candidate marker genes have also been identified for bacteria plus archaea: ribosomal protein S2 (rpsB), ribosomal protein S10 (rpsJ), ribosomal protein L1 (rplA), translation elongation factor EF-2, translation initiation factor IF-2, metalloendopeptidase, ribosomal protein L22, ffh signal recognition particle protein, ribosomal protein L4/L1e (rplD), ribosomal protein L2 (rplB), ribosomal protein S9 (rpsI), ribosomal protein L3 (rplC), phenylalanyl-tRNA synthetase beta subunit, ribosomal protein L14b/L23e (rplN), ribosomal protein S5, ribosomal protein S19 (rpsS), ribosomal protein S7, ribosomal protein L16/L10E (rplP), ribosomal protein S13 (rpsM), phenylalanyl-tRNA synthetase a subunit, ribosomal protein L15, ribosomal protein L25/L23, ribosomal protein L6 (rplF), ribosomal protein L11 (rplK), ribosomal protein L5 (rplE), ribosomal protein S12/S23, ribosomal protein L29, ribosomal protein S3 (rpsC), ribosomal protein S11 (rpsK), ribosomal protein L10, ribosomal protein S8, tRNA pseudouridine synthase B, ribosomal protein L18P/L5E, ribosomal protein S15P/S13e, Porphobilinogen deaminase, ribosomal protein S17, ribosomal protein L13 (rplM), phosphoribosylformylglycinamidine cyclo-ligase (rpsE), ribonuclease HII and ribosomal protein L24. Other candidate marker genes for bacteria include: transcription elongation protein NusA (nusA), rpoB DNA-directed RNA polymerase subunit beta (rpoB), GTP-binding protein EngA, rpoC DNA-directed RNA polymerase subunit beta', priA primosome assembly protein, transcription-repair coupling factor, CTP synthase (pyrG), secY preprotein translocase subunit SecY, GTP-binding protein Obg/CgtA, DNA polymerase I, rpsF 30S ribosomal protein S6, poA DNA-directed RNA polymerase subunit alpha, peptide chain release factor 1, rplI 50S ribosomal protein L9, polyribonucleotide nucleotidyltransferase, tsf elongation factor Ts (tsf), rplQ 50S ribosomal protein L17, tRNA (guanine-N(1)-)-methyltransferase (rplS), rplY probable 50S ribosomal protein L25, DNA repair protein RadA, glucose-inhibited division protein A, ribosome-binding factor A, DNA mismatch repair protein MutL, smpB SsrA-binding protein (smpB), N-acetylglucosaminyl transferase, S-adenosyl-methyltransferase MraW, UDP-N-acetylmuramoylalanine-D-glutamate ligase, rplS 50S ribosomal protein L19, rplT 50S ribosomal protein L20 (rplT), ruvA Holliday junction DNA helicase, ruvB Holliday junction DNA helicase B, serS seryl-tRNA synthetase, rplU 50S ribosomal protein L21, rpsR 30S ribosomal protein 518, DNA mismatch repair protein MutS, rpsT 30S ribosomal protein S20, DNA repair protein RecN, frr ribosome recycling factor (frr), recombination protein RecR, protein of unknown function UPF0054, miaA tRNA isopentenyltransferase, GTP-binding protein YchF, chromosomal replication initiator protein DnaA, dephospho-CoA kinase, 16S rRNA processing protein RimM, ATP-cone domain protein, 1-deoxy-D-xylulose 5-phosphate reductoisomerase, 2C-methyl-D-erythritol 2,4-cyclodiphosphate synthase, fatty acid/phospholipid synthesis protein PlsX, tRNA(Ile)-lysidine synthetase, dnaG DNA primase (dnaG), ruvC Holliday junction resolvase, rpsP 30S ribosomal protein 516, Recombinase A recA, riboflavin biosynthesis protein RibF, glycyl-tRNA synthetase beta subunit, trmU tRNA (5-methylaminomethyl-2-thiouridylate)-methyltransferase, rpmI 50S ribosomal protein L35, hemE uroporphyrinogen decarboxylase, Rod shape-determining protein, rpmA 50S ribosomal protein L27 (rpmA), peptidyl-tRNA hydrolase, translation initiation factor IF-3 (infC), UDP-N-acetylmuramyl-tripeptide synthetase, rpmF 50S ribosomal protein L32, rplL 50S ribosomal protein L7/L12 (rplL), leuS leucyl-tRNA synthetase, ligA NAD-dependent DNA ligase, cell division protein FtsA, GTP-binding protein TypA, ATP-dependent Clp protease, ATP-binding subunit ClpX, DNA replication and repair protein RecF and UDP-N-acetylenolpyruvoylglucosamine reductase.

Phospholipid fatty acids (PLFAs) can also be used as unique first markers according to the methods described herein. Because PLFAs are rapidly synthesized during microbial growth, are not found in storage molecules and degrade rapidly during cell death, it provides an accurate census of the current living community. All cells contain fatty acids (FAs) that can be extracted and esterified to form fatty acid methyl esters (FAMEs). When the FAMEs are analyzed using gas chromatography-mass spectrometry, the resulting profile constitutes a 'fingerprint' of the microorganisms in the sample. The chemical compositions of membranes for organisms in the domains Bacteria and Eukarya are comprised of fatty acids linked to the glycerol by an ester-type bond (phospholipid fatty acids (PLFAs)). In contrast, the membrane lipids of Archaea are composed of long and branched hydrocarbons that are joined to glycerol by an ether-type bond (phospholipid ether lipids (PLELs)). This is one of the most widely used non-genetic criteria to distinguish the three domains. In this context, the phospholipids derived from microbial cell membranes, characterized by different acyl chains, are excellent signature molecules, because such lipid structural diversity can be linked to specific microbial taxa.

As provided herein, in order to determine whether an organism strain is active, the level of expression of one or more unique second markers, which can be the same or different as the first marker, is measured (FIG. 1B, 1004; FIG. 2, 2004). Unique first markers are described above. The unique second marker is a marker of microorganism activity. For example, in one embodiment, the mRNA or protein expression of any of the first markers described above is considered a unique second marker for the purposes of this disclosure.

In one embodiment, if the level of expression of the second marker is above a threshold level (e.g., a control level) or at a threshold level, the microorganism is considered to be active (FIG. 1B, 1005; FIG. 2, 2005). Activity is determined in one embodiment, if the level of expression of the second marker is altered by at least about 5%, at least about 10%, at least about 15%, at least about 20%, at least about 25%, or at least about 30%, as compared to a threshold level, which in some embodiments, is a control level.

Second unique markers are measured, in one embodiment, at the protein, RNA or metabolite level. A unique second marker is the same or different as the first unique marker.

As provided above, a number of unique first markers and unique second markers can be detected according to the methods described herein. Moreover, the detection and quantification of a unique first marker is carried out according to methods known to those of ordinary skill in the art (FIG. 1B, 1003-1004, FIG. 2, 2003-2004).

Nucleic acid sequencing (e.g., gDNA, cDNA, rRNA, mRNA) in one embodiment is used to determine absolute cell count of a unique first marker and/or unique second marker. Sequencing platforms include, but are not limited to, Sanger sequencing and high-throughput sequencing methods available from Roche/454 Life Sciences, Illumina/Solexa, Pacific Biosciences, Ion Torrent and Nanopore. The sequencing can be amplicon sequencing of particular DNA or RNA sequences or whole metagenome/transcriptome shotgun sequencing.

Traditional Sanger sequencing (Sanger et al. (1977) DNA sequencing with chain-terminating inhibitors. Proc Natl. Acad. Sci. USA, 74, pp. 5463-5467, incorporated by reference herein in its entirety) relies on the selective incorporation of chain-terminating dideoxynucleotides by DNA polymerase during in vitro DNA replication and is amenable for use with the methods described herein.

In another embodiment, the sample, or a portion thereof is subjected to extraction of nucleic acids, amplification of DNA of interest (such as the rRNA gene) with suitable primers and the construction of clone libraries using sequencing vectors. Selected clones are then sequenced by Sanger sequencing and the nucleotide sequence of the DNA of interest is retrieved, allowing calculation of the number of unique microorganism strains in a sample.

454 pyrosequencing from Roche/454 Life Sciences yields long reads and can be harnessed in the methods described herein (Margulies et al. (2005) Nature, 437, pp. 376-380; U.S. Pat. Nos. 6,274,320; 6,258,568; 6,210,891, each of which is herein incorporated in its entirety for all purposes). Nucleic acid to be sequenced (e.g., amplicons or nebulized genomic/metagenomic DNA) have specific adapters affixed on either end by PCR or by ligation. The DNA with adapters is fixed to tiny beads (ideally, one bead will have one DNA fragment) that are suspended in a water-in-oil emulsion. An emulsion PCR step is then performed to make multiple copies of each DNA fragment, resulting in a set of beads in which each bead contains many cloned copies of the same DNA fragment. Each bead is then placed into a well of a fiber-optic chip that also contains enzymes necessary for the sequencing-by-synthesis reactions. The addition of bases (such as A, C, G, or T) trigger pyrophosphate release, which produces flashes of light that are recorded to infer the sequence of the DNA fragments in each well. About 1 million reads per run with reads up to 1,000 bases in length can be achieved. Paired-end sequencing can be done, which produces pairs of reads, each of which begins at one end of a given DNA fragment. A molecular barcode can be created and placed between the adapter sequence and the sequence of interest in multiplex reactions, allowing each sequence to be assigned to a sample bioinformatically.

Illumina/Solexa sequencing produces average read lengths of about 25 basepairs (bp) to about 300 bp (Bennett et al. (2005) Pharmacogenomics, 6:373-382; Lange et al. (2014). BMC Genomics 15, p. 63; Fadrosh et al. (2014) Microbiome 2, p. 6; Caporaso et al. (2012) ISME J, 6, p. 1621-1624; Bentley et al. (2008) Accurate whole human genome sequencing using reversible terminator chemistry. Nature, 456:53-59). This sequencing technology is also sequencing-by-synthesis but employs reversible dye terminators and a flow cell with a field of oligos attached. DNA fragments to be sequenced have specific adapters on either end and are washed over a flow cell filled with specific oligonucleotides that hybridize to the ends of the fragments. Each fragment is then replicated to make a cluster of identical fragments. Reversible dye-terminator nucleotides are then washed over the flow cell and given time to attach. The excess nucleotides are washed away, the flow cell is imaged, and the reversible terminators can be removed so that the process can repeat and nucleotides can continue to be added in subsequent cycles. Paired-end reads that are 300 bases in length each can be achieved. An Illumina platform can produce 4 billion fragments in a paired-end fashion with 125 bases for each read in a single run. Barcodes can also be used for sample multiplexing, but indexing primers are used.

The SOLiD (Sequencing by Oligonucleotide Ligation and Detection, Life Technologies) process is a "sequencing-by-ligation" approach, and can be used with the methods described herein for detecting the presence and quantity of a first marker and/or a second marker (FIG. 1B, 1003-1004; FIG. 2, 2003-2004) (Peckham et al. SOLiD™ Sequencing and 2-Base Encoding. San Diego, Calif.: American Society of Human Genetics, 2007; Mitra et al. (2013) Analysis of the intestinal microbiota using SOLiD 16S rRNA gene sequencing and SOLiD shotgun sequencing. BMC Genomics, 14(Suppl 5): S16; Mardis (2008) Next-generation DNA sequencing methods. Annu Rev Genomics Hum Genet, 9:387-402; each incorporated by reference herein in its entirety). A library of DNA fragments is prepared from the sample to be sequenced, and are used to prepare clonal bead populations, where only one species of fragment will be present on the surface of each magnetic bead. The fragments attached to the magnetic beads will have a universal P1 adapter sequence so that the starting sequence of every fragment is both known and identical. Primers hybridize to the P1 adapter sequence within the library template. A set of four fluorescently labelled di-base probes compete for ligation to the sequencing primer. Specificity of the di-base probe is achieved by interrogating every 1st and 2nd base in each ligation reaction. Multiple cycles of ligation, detection and cleavage are performed with the number of cycles determining the eventual read length. The SOLiD platform can produce up to 3 billion reads per run with reads that are 75 bases long. Paired-end sequencing is available and can be used herein, but with the second read in the pair being only 35 bases long. Multiplexing of samples is possible through a system akin to the one used by Illumina, with a separate indexing run.

The Ion Torrent system, like 454 sequencing, is amenable for use with the methods described herein for detecting the presence and quantity of a first marker and/or a second marker (FIG. 1B, 1003-1004; FIG. 2, 2003-2004). It uses a plate of microwells containing beads to which DNA fragments are attached. It differs from all of the other systems, however, in the manner in which base incorporation is detected. When a base is added to a growing DNA strand, a proton is released, which slightly alters the surrounding pH. Microdetectors sensitive to pH are associated with the wells on the plate, and they record when these changes occur. The different bases (A, C, G, T) are washed sequentially through the wells, allowing the sequence from each well to be inferred. The Ion Proton platform can produce up to 50 million reads per run that have read lengths of 200 bases. The Personal Genome Machine platform has longer reads at 400 bases. Bidirectional sequencing is available. Multiplexing is possible through the standard in-line molecular barcode sequencing.

Pacific Biosciences (PacBio) SMRT sequencing uses a single-molecule, real-time sequencing approach and in one embodiment, is used with the methods described herein for detecting the presence and quantity of a first marker and/or a second marker (FIG. 1B, 1003-1004; FIG. 2, 2003-2004). The PacBio sequencing system involves no amplification step, setting it apart from the other major next-generation sequencing systems. In one embodiment, the sequencing is performed on a chip containing many zero-mode waveguide (ZMW) detectors. DNA polymerases are attached to the ZMW detectors and phospholinked dye-labeled nucleotide incorporation is imaged in real time as DNA strands are synthesized. The PacBio system yields very long read lengths (averaging around 4,600 bases) and a very high number of reads per run (about 47,000). The typical "paired-end" approach is not used with PacBio, since reads are typically long enough that fragments, through CCS, can be covered multiple times without having to sequence from each end independently. Multiplexing with PacBio does not involve an independent read, but rather follows the standard "in-line" barcoding model.

In one embodiment, where the first unique marker is the ITS genomic region, automated ribosomal intergenic spacer analysis (ARISA) is used in one embodiment to determine the number and identity of microorganism strains in a sample (FIG. 1B, 1003, FIG. 2, 2003) (Ranjard et al. (2003). Environmental Microbiology 5, pp. 1111-1120, incorporated by reference in its entirety for all purposes). The ITS region has significant heterogeneity in both length and nucleotide sequence. The use of a fluorescence-labeled forward primer and an automatic DNA sequencer permits high resolution of separation and high throughput. The inclusion of an internal standard in each sample provides accuracy in sizing general fragments.

In another embodiment, fragment length polymorphism (RFLP) of PCR-amplified rDNA fragments, otherwise known as amplified ribosomal DNA restriction analysis (ARDRA), is used to characterize unique first markers and the quantity of the same in samples (FIG. 1B, 1003, FIG. 2, 2003) (for additional detail, see Massol-Deya et al. (1995). Mol. Microb. Ecol. Manual. 3.3.2, pp. 1-18, the entirety of which is herein incorporated by reference for all purposes). rDNA fragments are generated by PCR using general primers, digested with restriction enzymes, electrophoresed in agarose or acrylamide gels, and stained with ethidium bromide or silver nitrate.

One fingerprinting technique used in detecting the presence and abundance of a unique first marker is single-stranded-conformation polymorphism (SSCP) (see Lee et al. (1996). Appl Environ Microbiol 62, pp. 3112-3120; Scheinert et al. (1996). J. Microbiol. Methods 26, pp. 103-117; Schwieger and Tebbe (1998). Appl. Environ. Microbiol. 64, pp. 4870-4876, each of which is incorporated by reference herein in its entirety). In this technique, DNA fragments such as PCR products obtained with primers specific for the 16S rRNA gene, are denatured and directly electrophoresed on a non-denaturing gel. Separation is based on differences in size and in the folded conformation of single-stranded DNA, which influences the electrophoretic mobility. Reannealing of DNA strands during electrophoresis can be prevented by a number of strategies, including the use of one phosphorylated primer in the PCR followed by specific digestion of the phosphorylated strands with lambda exonuclease and the use of one biotinylated primer to perform magnetic separation of one single strand after denaturation. To assess the identity of the predominant populations in a given microbial community, in one embodiment, bands are excised and sequenced, or SSCP-patterns can be hybridized with specific probes. Electrophoretic conditions, such as gel matrix, temperature, and addition of glycerol to the gel, can influence the separation.

In addition to sequencing based methods, other methods for quantifying expression (e.g., gene, protein expression) of a second marker are amenable for use with the methods provided herein for determining the level of expression of one or more second markers (FIG. 1B, 1004; FIG. 2, 2004). For example, quantitative RT-PCR, microarray analysis, linear amplification techniques such as nucleic acid sequence based amplification (NASBA) are all amenable for use with the methods described herein, and can be carried out according to methods known to those of ordinary skill in the art.

In another embodiment, the sample, or a portion thereof is subjected to a quantitative polymerase chain reaction (PCR) for detecting the presence and quantity of a first marker and/or a second marker (FIG. 1B, 1003-1004; FIG. 2, 2003-2004). Specific microorganism strains activity is measured by reverse transcription of transcribed ribosomal and/or messenger RNA (rRNA and mRNA) into complementary DNA (cDNA), followed by PCR (RT-PCR).

In another embodiment, the sample, or a portion thereof is subjected to PCR-based fingerprinting techniques to detect the presence and quantity of a first marker and/or a second marker (FIG. 1B, 1003-1004; FIG. 2, 2003-2004). PCR products can be separated by electrophoresis based on the nucleotide composition. Sequence variation among the different DNA molecules influences the melting behavior, and therefore molecules with different sequences will stop migrating at different positions in the gel. Thus electrophoretic profiles can be defined by the position and the relative intensity of different bands or peaks and can be translated to numerical data for calculation of diversity indices. Bands can also be excised from the gel and subsequently sequenced to reveal the phylogenetic affiliation of the community members. Electrophoresis methods can include, but are not limited to: denaturing gradient gel electrophoresis (DGGE), temperature gradient gel electrophoresis (TGGE), single-stranded-conformation polymorphism (SSCP), restriction fragment length polymorphism analysis (RFLP) or amplified ribosomal DNA restriction analysis (ARDRA), terminal restriction fragment length polymorphism analysis (T-RFLP), automated ribosomal intergenic spacer analysis (ARISA), randomly amplified polymorphic DNA (RAPD), DNA amplification fingerprinting (DAF) and Bb-PEG electrophoresis.

In another embodiment, the sample, or a portion thereof is subjected to a chip-based platform such as microarray or microfluidics to determine the quantity of a unique first marker and/or presence/quantity of a unique second marker (FIG. 1B, 1003-1004, FIG. 2, 2003-2004). The PCR products are amplified from total DNA in the sample and directly hybridized to known molecular probes affixed to microarrays. After the fluorescently labeled PCR amplicons are hybridized to the probes, positive signals are scored by the use of confocal laser scanning microscopy. The microarray technique allows samples to be rapidly evaluated with replication, which is a significant advantage in microbial community analyses. The hybridization signal intensity on microarrays can be directly proportional to the quantity of the target organism. The universal high-density 16S microarray (e.g., PHYLOCHIP) contains about 30,000 probes of 16SrRNA gene targeted to several cultured microbial species and "candidate divisions". These probes target all 121 demarcated prokaryotic orders and allow simultaneous detection of 8,741 bacterial and archaeal taxa. Another microarray in use for profiling microbial communities is the Functional Gene Array (FGA). Unlike PHYLOCHPs, FGAs are designed primarily to detect specific metabolic groups of bacteria. Thus, FGA not only reveal the community structure, but they also shed light on the in situ community metabolic potential. FGA contain probes from genes with known biological functions, so they are useful in linking microbial community composition to ecosystem functions. An FGA termed GEOCHIP contains >24,000 probes from all known metabolic genes involved in various biogeochemical, ecological, and environmental processes such as ammonia oxidation, methane oxidation, and nitrogen fixation.

A protein expression assay, in one embodiment, is used with the methods described herein for determining the level of expression of one or more second markers (FIG. 1B, 1004; FIG. 2, 2004). For example, in one embodiment, mass spectrometry or an immunoassay such as an enzyme-linked immunosorbant assay (ELISA) is utilized to quantify the level of expression of one or more unique second markers, wherein the one or more unique second markers is a protein.

In one embodiment, the sample, or a portion thereof is subjected to Bromodeoxyuridine (BrdU) incorporation to determine the level of a second unique marker (FIG. 1B, 1004; FIG. 2, 2004). BrdU, a synthetic nucleoside analog of thymidine, can be incorporated into newly synthesized DNA of replicating cells. Antibodies specific for BRdU can then be used for detection of the base analog. Thus BrdU incorporation identifies cells that are actively replicating their DNA, a measure of activity of a microorganism according to one embodiment of the methods described herein. BrdU incorporation can be used in combination with FISH to provide the identity and activity of targeted cells.

In one embodiment, the sample, or a portion thereof is subjected to microautoradiography (MAR) combined with FISH to determine the level of a second unique marker (FIG. 1B, 1004; FIG. 2, 2004). MAR-FISH is based on the incorporation of radioactive substrate into cells, detection of the active cells using autoradiography and identification of the cells using FISH. The detection and identification of active cells at single-cell resolution is performed with a microscope. MAR-FISH provides information on total cells, probe targeted cells and the percentage of cells that incorporate a given radiolabelled substance. The method provides an assessment of the in situ function of targeted microorganisms and is an effective approach to study the in vivo physiology of microorganisms. A technique developed for quantification of cell-specific substrate uptake in combination with MAR-FISH is known as quantitative MAR (QMAR).

In one embodiment, the sample, or a portion thereof is subjected to stable isotope Raman spectroscopy combined with FISH (Raman-FISH) to determine the level of a second unique marker (FIG. 1B, 1004; FIG. 2, 2004). This technique combines stable isotope probing, Raman spectroscopy and FISH to link metabolic processes with particular organisms. The proportion of stable isotope incorporation by cells affects the light scatter, resulting in measurable peak shifts for labelled cellular components, including protein and mRNA components. Raman spectroscopy can be used to identify whether a cell synthesizes compounds including, but not limited to: oil (such as alkanes), lipids (such as triacylglycerols (TAG)), specific proteins (such as heme proteins, metalloproteins), cytochrome (such as P450, cytochrome c), chlorophyll, chromophores (such as pigments for light harvesting carotenoids and rhodopsins), organic polymers (such as polyhydroxyalkanoates (PHA), polyhydroxybutyrate (PHB)), hopanoids, steroids, starch, sulfide, sulfate and secondary metabolites (such as vitamin B12).

In one embodiment, the sample, or a portion thereof is subjected to DNA/RNA stable isotope probing (SIP) to determine the level of a second unique marker (FIG. 1B, 1004; FIG. 2, 2004). SIP enables determination of the microbial diversity associated with specific metabolic pathways and has been generally applied to study microorganisms involved in the utilization of carbon and nitrogen compounds. The substrate of interest is labelled with stable isotopes (such as $^{13}C$ or $^{15}N$) and added to the sample. Only microorganisms able to metabolize the substrate will incorporate it into their cells. Subsequently, $^{13}C$-DNA and $^{15}N$-DNA can be isolated by density gradient centrifugation and used for metagenomic analysis. RNA-based SIP can be a responsive biomarker for use in SIP studies, since RNA itself is a reflection of cellular activity.

In one embodiment, the sample, or a portion thereof is subjected to isotope array to determine the level of a second unique marker (FIG. 1B, 1004; FIG. 2, 2004). Isotope arrays allow for functional and phylogenetic screening of active microbial communities in a high-throughput fashion. The technique uses a combination of SIP for monitoring the substrate uptake profiles and microarray technology for determining the taxonomic identities of active microbial communities. Samples are incubated with a $^{14}C$-labeled substrate, which during the course of growth becomes incorporated into microbial biomass. The $^{14}C$-labeled rRNA is separated from unlabeled rRNA and then labeled with fluorochromes. Fluorescent labeled rRNA is hybridized to a phylogenetic microarray followed by scanning for radioactive and fluorescent signals. The technique thus allows simultaneous study of microbial community composition and specific substrate consumption by metabolically active microorganisms of complex microbial communities.

In one embodiment, the sample, or a portion thereof is subjected to a metabolomics assay to determine the level of a second unique marker (FIG. 1B, 1004; FIG. 2, 2004). Metabolomics studies the metabolome which represents the collection of all metabolites, the end products of cellular processes, in a biological cell, tissue, organ or organism. This methodology can be used to monitor the presence of microorganisms and/or microbial mediated processes since it allows associating specific metabolite profiles with different microorganisms. Profiles of intracellular and extracellular metabolites associated with microbial activity can be obtained using techniques such as gas chromatography-mass spectrometry (GC-MS). The complex mixture of a metabolomic sample can be separated by such techniques as gas chromatography, high performance liquid chromatography and capillary electrophoresis. Detection of metabolites can be by mass spectrometry, nuclear magnetic resonance (NMR) spectroscopy, ion-mobility spectrometry, electrochemical detection (coupled to HPLC) and radiolabel (when combined with thin-layer chromatography).

According to the embodiments described herein, the presence and respective number of one or more active microorganism strains in a sample are determined (FIG. 1B, 1006; FIG. 2, 2006). For example, strain identity information obtained from assaying the number and presence of first markers is analyzed to determine how many occurrences of a unique first marker are present, thereby representing a unique microorganism strain (e.g., by counting the number of sequence reads in a sequencing assay). This value can be represented in one embodiment as a percentage of total sequence reads of the first maker to give a percentage of unique microorganism strains of a particular microorganism type. In a further embodiment, this percentage is multiplied by the number of microorganism types (obtained at step 1002 or 2002, see FIG. 1B and FIG. 2) to give the absolute cell count of the one or more microorganism strains in a sample and a given volume.

The one or more microorganism strains are considered active, as described above, if the level of second unique marker expression is at a threshold level, higher than a threshold value, e.g., higher than at least about 5%, at least about 10%, at least about 20% or at least about 30% over a control level.

In another aspect of the disclosure, a method for determining the absolute cell count of one or more microorganism strains is determined in a plurality of samples (FIG. 2, see in particular, 2007). For a microorganism strain to be classified as active, it need only be active in one of the samples. The samples can be taken over multiple time points from the same source, or can be from different environmental sources (e.g., different animals).

The absolute cell count values over samples are used in one embodiment to relate the one or more active microorganism strains, with an environmental parameter (FIG. 2, 2008). In one embodiment, the environmental parameter is the presence of a second active microorganism strain. Relating the one or more active microorganism strains to the environmental parameter, in one embodiment, is carried out by determining the co-occurrence of the strain and parameter by network analysis and/or graph theory.

In one embodiment, determining the co-occurrence of one or more active microorganism strains with an environmental parameter comprises a network and/or cluster analysis method to measure connectivity of strains or a strain with an environmental parameter within a network, wherein the network is a collection of two or more samples that share a common or similar environmental parameter. Examples of measurement of independence are provided and discussed herein, and additional details can be understood by configuring the teachings and methods of: Blomqvist "On a measure of dependence between two random variables" The Annals of Mathematical Statistics (1950): 593-600; Hollander et al. "Nonparametric statistical methods—Wiley series in probability and statistics Texts and references section" (1999); and/or Blum et al. "Distribution free tests of independence based on the sample distribution function" The Annals of Mathematical Statistics (1961): 485-498; the entirety of each of the aforementioned publications being herein expressly incorporated by reference for all purposes.

In another embodiment, correlation methods including Pearson correlation, Spearman correlation, Kendall correlation, Canonical Correlation Analysis, Likelihood ratio tests (e.g., by adapting the teachings and methods detailed in Wilks, S. S. "On the Independence of k Sets of Normally Distributed Statistical Variables" Econometrica, Vol. 3, No. 3, July 1935, pp 309-326, the entirety of which is herein expressly incorporated by reference for all purposes), and canonical correlation analysis are used establish connectivity between variables. Multivariate extensions of these methods, Maximal correlation (see, e.g., Alfréd Rényi "On measures of dependence" Acta mathematica hungarica 10.3-4 (1959): 441-451, herein expressly incorporated by reference in its entirety), or both (MAC) can be used when appropriate, depending on the number of variables being compared. Some embodiments utilize Maximal Correlation Analysis and/or other multivariate correlation measures configured for discovering multi-dimensional patterns (for example, by adapting the methods and teachings of "Multivariate Maximal Correlation Analysis," Nguyen et al., Proceedings of the 31st International Conference on Machine Learning, Beijing, China, 2014, which is herein expressly incorporated by reference in its entirety for all purposes). In some embodiments, network metrics and analysis, such as discussed by Farine et al, in "Constructing, Conducting and Interpreting Animal Social Network Analysis" Journal of Animal Ecology, 2015, 84, pp. 1144-1163. doi:10.1111/1365-2656.12418 (the entirety of which is herein expressly incorporated by reference for all purposes) can be utilized and configured for the disclosure.

In some embodiments, network analysis comprises nonparametric approaches (e.g., by adapting the teaching and methods detailed in Taskinen et al. "Multivariate nonparametric tests of independence." Journal of the American Statistical Association 100.471 (2005): 916-925; and Gieser et al. "A Nonparametric Test of Independence Between Two Vectors." Journal of the American Statistical Association, Vol. 92, No. 438, June, 1977, pp 561-567; entirety of each of being herein expressly incorporated by reference for all purposes), including mutual information Maximal Information Coefficient, Maximal Information Entropy (MIE; e.g., by adapting the teachings and methods of Zhang Ya-hong et al. "Detecting Multivariable Correlation with Maximal Information Entropy[J]" Journal of Electronics & Information Technology, 2015-01 (37(1): 123-129), the entirety of which is herein expressly incorporated by reference for all purposes), Kernel Canonical Correlation Analysis (KCCA; e.g., by adapting the teachings and methods detailed in Bach et al. "Kernel Independent Component Analysis" Journal of Machine Learning Research 3 (2002) 1-48, the entirety of which is herein expressly incorporated by reference for all purposes), Alternating Conditional Expectation or backfitting algorithms (ACE; e.g., by adapting the teaching and methods detailed in Breiman et al. "Estimating Optimal Transformations for Multiple Regression and Correlation: Rejoinder." Journal of the American Statistical Association 80, no. 391 (1985): 614-19, doi:10.2307/2288477, the entirety of which is herein expressly incorporated by reference for all purposes), Distance correlation measure (dcor;

e.g., by adapting the teaching and methods detailed in Szekely et al. "Measuring and Testing Dependence by Correlation of Distances" The Annals of Statistics, 2007, Vol. 35, No. 6, 2769-2794, doi:10.1214/009053607000000505, the entirety of which is herein expressly incorporated by reference for all purposes), Brownian distance covariance (dcov; e.g., by adapting the teaching and methods detailed in Szekely et al. "Brownian Distance Covariance" The Annals of Applied Statistics, 2009, Vol. 3, No. 4, 1236-1265, Doi:10.1214/09-AOAS312, the entirety of which is herein expressly incorporated by reference for all purposes), Hilbert-Schmidt Independence Criterion (HSCI/CHSI; e.g., by adapting the teachings and methods detailed in Gretton et al. "A Kemal Two-Sample Test" Journal of Machine Learning Research 13 (2012) 723-773, and Poczos et al. "Copula-based Kernel Dependency Measures" Carnegie Mellow University, Research Showcase@CMU, Proceedings of the 29th International Conference on Machine Learning, each of which is herein expressly incorporated by reference in their entireties for all purposes), Randomized Dependence Coefficient (RDC; e.g., by adapting the teaching and methods detailed in Lopez-Paz et al. "The Randomized Dependence Coefficient" Advances in Neural Information Processing Systems (2013), the entirety of which is herein expressly incorporated by reference for all purposes) to establish connectivity between variables. In some embodiments, one or more of these methods can be coupled to bagging or boosting methods, or k nearest neighbor estimators (e.g., by adapting the teaching and methods detailed in: Breiman, "Arcing Classifiers" The Annals of Statistics, 1998, Vol. 26, No. 3, 801-849; Liu, "Modified Bagging of Maximal Information Coefficient for Genome-wide Identification" Int. J. Data Mining and Bioinformatics, Vol. 14, No. 3, 2016, pp. 229-257; and/or Gao et al. "Efficient Estimation of Mutual Information for Strongly Dependent Variables" Proceedings of the 18th International Conference on Artificial Intelligence and Statistics (AISTATS), 2015, San Diego, Calif., JMLR: W&CP Volume 38; each of which is herein expressly incorporated by reference in its entirety for all purposes).

In some embodiments, the network analysis comprises node-level analysis, including degree, strength, betweenness centrality, eigenvector centrality, page rank, and reach. In another embodiment, the network analysis comprises network level metrics, including density, homophily or assortativity, transitivity, linkage analysis, modularity analysis, robustness measures, betweenness measures, connectivity measures, transitivity measures, centrality measures or a combination thereof. In others embodiments, species community rules (see, e.g., Connor et al. "The Assembly of Species Communities: Chance or Competition?" Ecology, Vol. 60, No. 6 (December, 1979), pp. 1132-1140, the entirety of which is herein incorporated by reference for all purposes) are applied to the network, which can include leveraging Gambit of the Group assumptions (e.g., by applying the methods and teachings of Franks et al. "Sampling Animal Association Networks with the Gambit of the Group" Behav Ecol Sociobiol (2010) 64:493, doi:10.1007/x00265-0098-0865-8, the entirety of which is herein expressly incorporated by reference for all purposes). In some embodiments, eigenvectors/modularity matrix analysis methods can be used, e.g., by configuring the teachings and methods as discussed by Mark E J Newman in "Finding community structure in networks using the eigenvectors of matrices" Physical Review E 74.3 (2006): 036104, the entirety of which is herein expressly incorporated by reference for all purposes.

In some embodiments, time-aggregated networks or time-ordered networks are utilized. In another embodiment, the cluster analysis method comprises building or constructing an observation matrix, connectivity model, subspace model, distribution model, density model, or a centroid model, using community detection in graphs, and/or using community detection algorithms such as, by way of non-limiting example, the Louvain, Bron-Kerbosch, Girvan-Newman, Clauset-Newman-Moore, Pons-Latapy, and Wakita-Tsurumi algorithms.

In some embodiments, the cluster analysis method is a heuristic method based on modularity optimization. In a further embodiment, the cluster analysis method is the Louvain method (see, e.g., the method described by Blondel et al. (2008) Fast unfolding of communities in large networks. Journal of Statistical Mechanics: Theory and Experiment, Volume 2008, October 2008, incorporated by reference herein in its entirety for all purposes, and which can be adapted for use in the methods disclosed herein).

In other embodiments, the network analysis comprises predictive modeling of network through link mining and prediction, collective classification, link-based clustering, hierarchical cluster analysis, relational similarity, or a combination thereof. In another embodiment, the network analysis comprises differential equation based modeling of populations. In another embodiment, the network analysis comprises Lotka-Volterra modeling.

In some embodiments, relating the one or more active microorganism strains to an environmental parameter (e.g., determining the co-occurrence) in the sample comprises creating matrices populated with linkages denoting environmental parameter and microorganism strain associations.

In some embodiments, the multiple sample data obtained at step 2007 (e.g., over two or more samples which can be collected at two or more time points where each time point corresponds to an individual sample) is compiled. In a further embodiment, the number of cells of each of the one or more microorganism strains in each sample is stored in an association matrix (which can be in some embodiments, a quantity matrix). In one embodiment, the association matrix is used to identify associations between active microorganism strains in a specific time point sample using rule mining approaches weighted with association (e.g., quantity) data. Filters are applied in one embodiment to remove insignificant rules.

In some embodiments, the absolute cell count of one or more, or two or more active microorganism strains is related to one or more environmental parameters (FIG. 2, 2008), e.g., via co-occurrence determination. Environmental parameters can be selected depending on the sample(s) to be analyzed and are not restricted by the methods described herein. The environmental parameter can be a parameter of the sample itself, e.g., pH, temperature, amount of protein in the sample. Alternatively, the environmental parameter is a parameter that affects a change in the identity of a microbial community (i.e., where the "identity" of a microbial community is characterized by the type of microorganism strains and/or number of particular microorganism strains in a community), or is affected by a change in the identity of a microbial community. For example, an environmental parameter in one embodiment, is the food intake of an animal or the amount of milk (or the protein or fat content of the milk) produced by a lactating ruminant. In one embodiment, the environmental parameter is the presence, activity and/or quantity of a second microorganism strain in the microbial community, present in the same sample. In some embodiments described herein, an environmental parameter is referred to as a metadata parameter, and vice-versa.

Other examples of metadata parameters include but are not limited to genetic information from the host from which the sample was obtained (e.g., DNA mutation information), sample pH, sample temperature, expression of a particular protein or mRNA, nutrient conditions (e.g., level and/or identity of one or more nutrients) of the surrounding environment/ecosystem), susceptibility or resistance to disease, onset or progression of disease, susceptibility or resistance of the sample to toxins, efficacy of xenobiotic compounds (pharmaceutical drugs), biosynthesis of natural products, or a combination thereof.

For example, according to one embodiment, microorganism strain number changes are calculated over multiple samples according to the method of FIG. 2 (i.e., at 2001-2007). Strain number changes of one or more active strains over time is compiled (e.g., one or more strains that have initially been identified as active according to step 2006), and the directionality of change is noted (i.e., negative values denoting decreases, positive values denoting increases). The number of cells over time is represented as a network, with microorganism strains representing nodes and the quantity weighted rules representing edges. Markov chains and random walks are leveraged to determine connectivity between nodes and to define clusters. Clusters in one embodiment are filtered using metadata in order to identify clusters associated with desirable metadata (FIG. 2, 2008).

In a further embodiment, microorganism strains are ranked according to importance by integrating cell number changes over time and strains present in target clusters, with the highest changes in cell number ranking the highest.

Network and/or cluster analysis method in one embodiment, is used to measure connectivity of the one or more strains within a network, wherein the network is a collection of two or more samples that share a common or similar environmental parameter. In one embodiment, network analysis comprises linkage analysis, modularity analysis, robustness measures, betweenness measures, connectivity measures, transitivity measures, centrality measures or a combination thereof. In another embodiment, network analysis comprises predictive modeling of network through link mining and prediction, social network theory, collective classification, link-based clustering, relational similarity, or a combination thereof. In another embodiment, network analysis comprises mutual information, maximal information coefficient calculations, or other nonparametric methods between variables to establish connectivity. In another embodiment, network analysis comprises differential equation based modeling of populations. In yet another embodiment, network analysis comprises Lotka-Volterra modeling.

Cluster analysis method comprises building a connectivity model, subspace model, distribution model, density model, or a centroid model.

Network and cluster based analysis, for example, to carry out method step 2008 of FIG. 2, can be carried out via a processor, component and/or module. As used herein, a component and/or module can be, for example, any assembly, instructions and/or set of operatively-coupled electrical components, and can include, for example, a memory, a processor, electrical traces, optical connectors, software (executing in hardware) and/or the like.

Figure 3A:
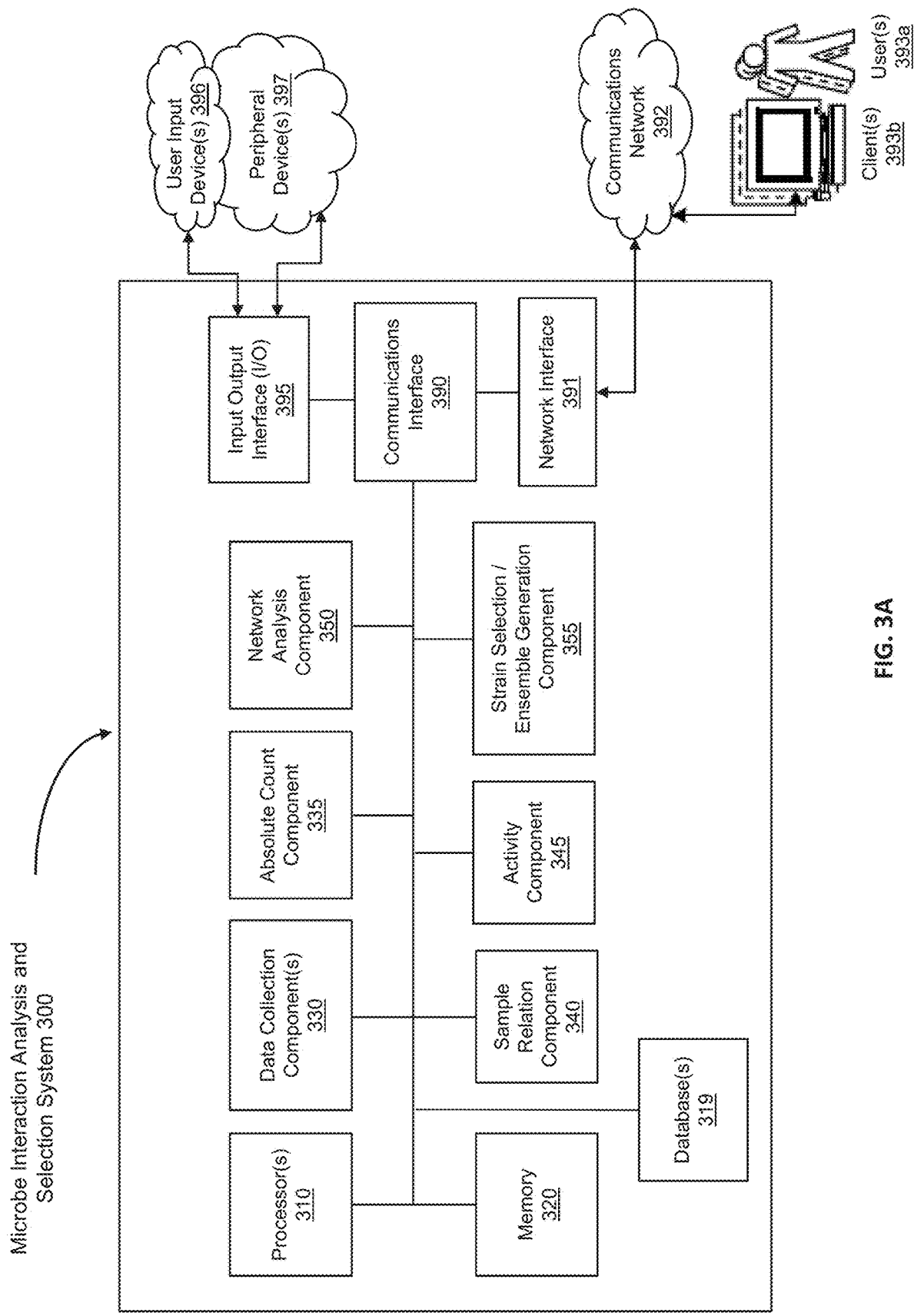
FIG. 3A is a schematic diagram that illustrates an exemplary microbe interaction analysis and selection system 300, according to some embodiments.

FIG. 3A is a schematic diagram that illustrates a microbe analysis, screening and selection platform and system 300, according to an embodiment. A platform according to the disclosure can include systems and processes to determine multi-dimensional interspecies interactions and dependencies within natural microbial communities, and an example is described with respect to FIG. 3A. FIG. 3A is an architectural diagram, and therefore certain aspects are omitted to improve the clarity of the description, though these aspects should be apparent to one of skill when viewed in the context of the disclosure.

As shown in FIG. 3A, the microbe screening and selection platform and system 300 can include one or more processors 310, a database 319, a memory 320, a communications interface 390, an input/output interface configured to interact with user input devices 396 and peripheral devices 397 (including but not limited to data collection and analysis devices, such as FACS, selection/incubation/formulation devices, and/or additional databases/data sources, remote data collection devices (e.g., devices that can collect metadata environmental data, such as sample characteristics, temperature, weather, etc., including mobile smart phones running apps to collect such information as well as other mobile or stationary devices), a network interface 391 configured to receive and transmit data over communications network 392 (e.g., LAN, WAN, and/or the Internet) to clients 393b (which can include user interfaces and/or displays, such as graphical displays) and users 393a; a data collection component 330, an absolute count component 335, a sample relation component 340, an activity component 345, a network analysis component 350, and a strain selection/microbial ensemble generation component 355. In some embodiments, the microbe screening system 300 can be a single physical device. In other embodiments, the microbe screening system 300 can include multiple physical devices (e.g., operatively coupled by a network), each of which can include one or multiple component and/or module shown in FIG. 3A.

Each component or module in the microbe screening system 300 can be operatively coupled to each remaining component and/or module. Each component and/or module in the microbe screening system 300 can be any combination of hardware and/or software (stored and/or executing in hardware) capable of performing one or more specific functions associated with that component and/or module.

The memory 320 can be, for example, a random-access memory (RAM) (e.g., a dynamic RAM, a static RAM), a flash memory, a removable memory, a hard drive, a database and/or so forth. In some embodiments, the memory 320 can include, for example, a database (e.g., as in 319), process, application, virtual machine, and/or some other software components, programs and/or modules (stored and/or executing in hardware) or hardware components/modules configured to execute a microbe screening process and/or one or more associated methods for microbe screening and ensemble generation (e.g., via the data collection component 330, the absolute count component 335, the sample relation component 340, the activity component 345, the network analysis component 350, the strain selection/microbial ensemble generation component 355 (and/or similar modules)). In such embodiments, instructions of executing the microbe screening and/or ensemble generation process and/or the associated methods can be stored within the memory 320 and executed at the processor 310. In some embodiments, data collected via the data collection component 330 can be stored in a database 319 and/or in the memory 320.

The processor 310 can be configured to control, for example, the operations of the communications interface 390, write data into and read data from the memory 320, and execute the instructions stored within the memory 320. The processor 310 can also be configured to execute and/or control, for example, the operations of the data collection component 330, the absolute count component 335, the sample relation component 340, the activity component, and the network analysis component 350, as described in further detail herein. In some embodiments, under the control of the processor(s) 310 and based on the methods or processes stored within the memory 320, the data collection component 330, absolute count component 335, sample relation component 340, activity component 345, network analysis component 350, and strain selection/ensemble generation component 355 can be configured to execute a microbe screening, selection and synthetic ensemble generation process, as described in further detail herein.

The communications interface 390 can include and/or be configured to manage one or multiple ports of the microbe screening system 300 (e.g., via input out interface(s) 395). In some instances, for example, the communications interface 390 (e.g., a Network Interface Card (NIC)) can include one or more line cards, each of which can include one or more ports (operatively) coupled to devices (e.g., peripheral devices 397 and/or user input devices 396). A port included in the communications interface 390 can be any entity that can actively communicate with a coupled device or over a network 392 (e.g., communicate with end-user devices 393b, host devices, servers, etc.). In some embodiments, such a port need not necessarily be a hardware port, but can be a virtual port or a port defined by software. The communication network 392 can be any network or combination of networks capable of transmitting information (e.g., data and/or signals) and can include, for example, a telephone network, an Ethernet network, a fiber-optic network, a wireless network, and/or a cellular network. The communication can be over a network such as, for example, a Wi-Fi or wireless local area network ("WLAN") connection, a wireless wide area network ("WWAN") connection, and/or a cellular connection. A network connection can be a wired connection such as, for example, an Ethernet connection, a digital subscription line ("DSL") connection, a broadband coaxial connection, and/or a fiber-optic connection. For example, the microbe screening system 300 can be a host device configured to be accessed by one or more compute devices 393b via a network 392. In such a manner, the compute devices can provide information to and/or receive information from the microbe screening system 300 via the network 392. Such information can be, for example, information for the microbe screening system 300 to collect, relate, determine, analyze and/or generate ensembles of active, network-analyzed microbes, as described in further detail herein. Similarly, the compute devices can be configured to retrieve and/or request determined information from the microbe screening system 300.

In some embodiments, the communications interface 390 can include and/or be configured to include input/output interfaces 395. The input/output interfaces can accept, communicate, and/or connect to user input devices, peripheral devices, cryptographic processor devices, and/or the like. In some instances, one output device can be a video display, which can include, for example, a Cathode Ray Tube (CRT) or Liquid Crystal Display (LCD), LED, or plasma based monitor with an interface (e.g., Digital Visual Interface (DVI) circuitry and cable) that accepts signals from a video interface. In such embodiments, the communications interface 390 can be configured to, among other functions, receive data and/or information, and send microbe screening modifications, commands, and/or instructions.

The data collection component 330 can be any hardware and/or software component and/or module (stored in a memory such as the memory 320 and/or executing in hardware such as the processor 310) configured to collect, process, and/or normalize data for analysis on multi-dimensional interspecies interactions and dependencies within natural microbial communities performed by the absolute count component 335, sample relation component 340, activity component 345, network analysis component 350, and/or strain selection/ensemble generation component 355. In some embodiments, the data collection component 330 can be configured to determine absolute cell count of one or more active organism strains in a given volume of a sample. Based on the absolute cell count of one more active microorganism strains, the data collection component 330 can identify active strains within absolute cell count datasets using marker sequences. The data collection component 330 can continuously collect data for a period of time to represent the dynamics of microbial populations within a sample. The data collection component 330 can compile temporal data and store the number of cells of each active organism strain in a quantity matrix in a memory such as the memory 320.

The sample relation component 340 and the network analysis component 350 can be configured to collectively determine multi-dimensional interspecies interactions and dependencies within natural microbial communities. The sample relation component 340 can be any hardware and/or software component (stored in a memory such as the memory 320 and/or executing in hardware such as the processor 310) configured to relate a metadata parameter (environmental parameter, e.g., via co-occurrence) to presence of one or more active microorganism strains. In some embodiments, the sample relation component 340 can relate the one or more active organism strains to one or more environmental parameters.

The network analysis component 350 can be any hardware and/or software component (stored in a memory such as the memory 320 and/or executing in hardware such as the processor 310) configured to determine co-occurrence of one or more active microorganism strains in a sample to an environmental (metadata) parameter. In some embodiments, based on the data collected by the data collection component 330, and the relation between the one or more active microorganism strains to one or more environmental parameters determined by the sample relation component 340, the network analysis component 350 can create matrices populated with linkages denoting environmental parameters and microorganism strain associations, the absolute cell count of the one or more active microorganism strains and the level of expression of the one or more unique second markers to represent one or more networks of a heterogeneous population of microorganism strains. For example, the network analysis can use an association (quantity and/or abundance) matrix to identify associations between an active microorganism strain and a metadata parameter (e.g., the associations of two or more active microorganism strains) in a sample using rule mining approaches weighted with quantity data. In some embodiments, the network analysis component 350 can apply filters to select and/or remove rules. The network analysis component 350 can calculate cell number changes of active strains over time, noting directionality of change (i.e., negative values denoting decreases, positive values denoting increases). The network analysis component 350 can represent matrix as a network, with microorganism strains representing nodes and the quantity weighted rules representing edges. The network analysis component 350 can use leverage markov chains and random walks to determine connectivity between nodes and to define clusters. In some embodiments, the network analysis component 350 can filter clusters using metadata in order to identify clusters associated with desirable metadata. In some embodiments, the network analysis component 350 can rank target microorganism strains by integrating cell number changes over time and strains present in target clusters, with highest changes in cell number ranking the highest.

In some embodiments, the network analysis includes linkage analysis, modularity analysis, robustness measures, betweenness measures, connectivity measures, transitivity measures, centrality measures or a combination thereof. In another embodiment, a cluster analysis method can be used including building a connectivity model, subspace model, distribution model, density model, or a centroid model. In another embodiment, the network analysis includes predictive modeling of network through link mining and prediction, collective classification, link-based clustering, relational similarity, or a combination thereof. In another embodiment, the network analysis comprises mutual information, maximal information coefficient calculations, or other nonparametric methods between variables to establish connectivity. In another embodiment, the network analysis includes differential equation based modeling of populations. In another embodiment, the network analysis includes Lotka-Volterra modeling.

Figure 3B:
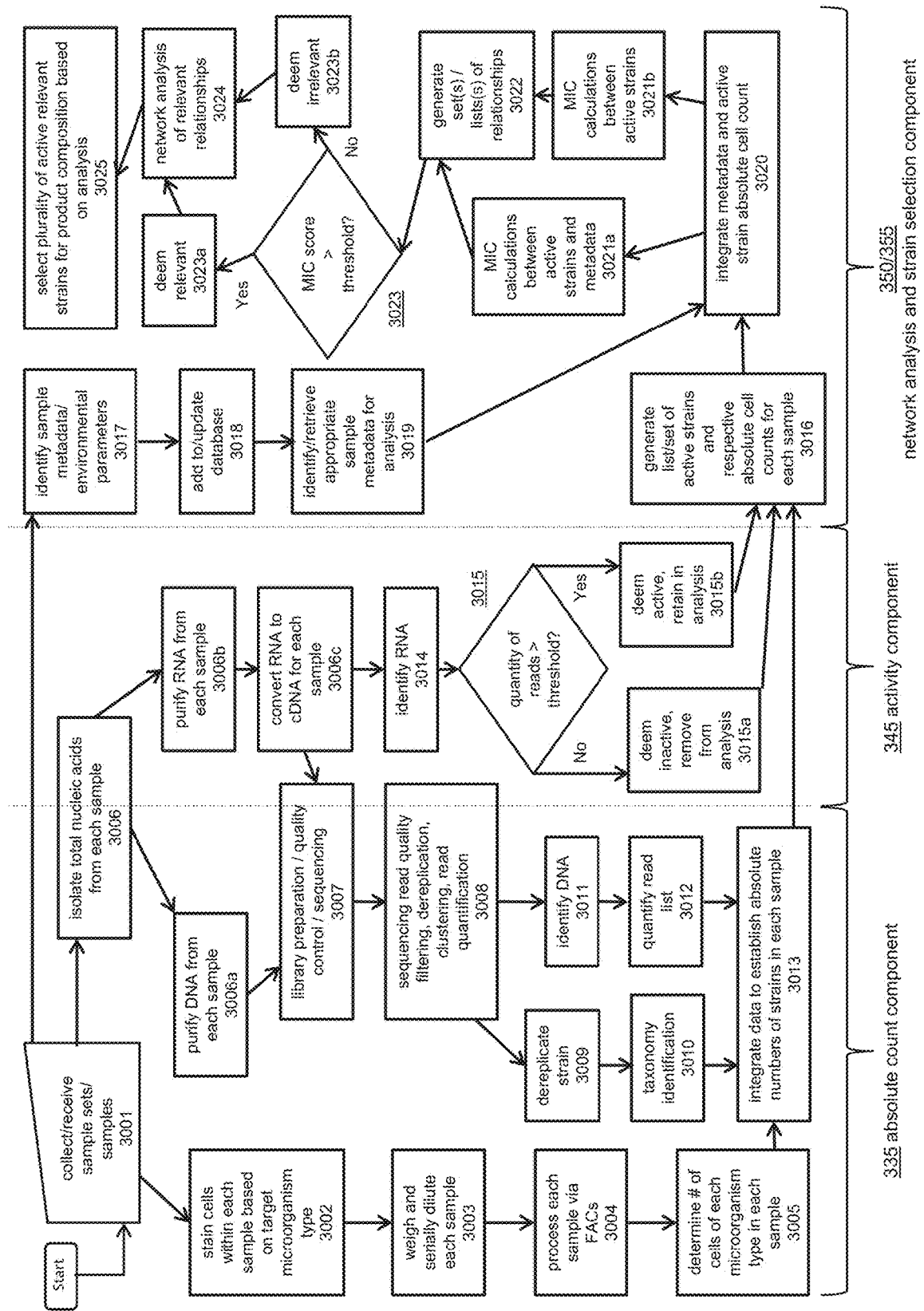
FIG. 3B is example process flow for use with such a system. Systems and processes to determine multi-dimensional interspecies interactions and dependencies within natural microbial communities, identify active microbes, and select a plurality of active microbes to form an ensemble, aggregate or other synthetic grouping of microorganisms that will alter specified parameter(s) and/or related measures, is described with respect to FIGS. 3A and 3B.

FIG. 3B shows an exemplary logic flow according to one embodiment of the disclosure. To begin, a plurality of samples and/or sample sets are collected and/or received 3001. It is to be understood that as used herein, "sample" can refer to one or more samples, a sample set, a plurality of samples (e.g., from particular population), such that when two or more different samples are discussed, that is for ease of understanding, and each sample can include a plurality of sub sample (e.g., when a first sample and second sample are discussed, the first sample can include 2, 3, 4, 5 or more sub samples, collected from a first population, and the second sample can include 2, 3, 4, 5 or more sub samples collected from a second population, or alternatively, collected from the first population but at a different point in time, such as one week or one month after collection of the first sub-sample). When sub-samples are collected, individual collection indicia and parameters for each sub-sample can be monitored and stored, including environmental parameters, qualitative and/or quantitative observations, population member identity (e.g., so when sample are collected from the same population at two or more different time, the sub-samples are paired by identify, so subsample at time 1 from animal 1 is linked to a subsample collected from that same animal at time 2, and so forth).

For each sample, sample set, and/or subsample, the cells are stained based on the target organism type 3002, each sample/subsample or portion thereof is weighed and serially diluted 3003, and processed 3004 to determine the number of cells of each microorganism type in each sample/sub-sample. In one exemplary implementation, a cell sorter can be used to count individual bacterial and fungal cells from samples, such as from an environmental sample. As part of the disclosure, specific dyes were developed to enable counting of microorganisms that previously were not countable according to the traditional methods. Following the methods of the disclosure, specific dyes are used to stain cell walls (e.g., for bacteria and/or fungi), and discrete populations of target cells can be counted from a greater population based on cellular characteristics using lasers. In one specific example, environmental samples are prepared and diluted into isotonic buffer solution and stained with dyes: (a) for bacteria, the following dyes can be used to stain—DNA: Sybr Green, Respiration: 5-cyano-2,3-ditolyltetrazolium chloride and/or CTC, Cell wall: Malachite Green and/or Crystal Violet; (b) for fungi, the following dyes can be used to stain—Cell wall: Calcofluor White, Congo Red, Trypan Blue, Direct Yellow 96, Direct Yellow 11, Direct Black 19, Direct Orange 10, Direct Red 23, Direct Red 81, Direct Green 1, Direct Violet 51, Wheat Germ Agglutinin—WGA, Reactive Yellow 2, Reactive Yellow 42, Reactive Black 5, Reactive Orange 16, Reactive Red 23, Reactive Green 19, and/or Reactive Violet 5.

In the development of this disclosure, it was advantageously discovered that although direct and reactive dyes are typically associated with the staining of cellulose-based materials (i.e., cotton, flax, and viscose rayon), they can also be used to stain chitin and chitosan because of the presence of β-(1→4)-linked N-acetylglucosamine chains, and β-(1→4)-linked D-glucosamine and N-acetyl-D-glucosamine chains, respectively. When these subunits assemble into a chain, a flat, fiber-like structure very similar to cellulose chains is formed. Direct dyes adhere to chitin and/or chitosan molecules via Van der Waals forces between the dye and the fiber molecule. The more surface area contact between the two, the stronger the interaction. Reactive dyes, on the other hand, form a covalent bond to the chitin and/or chitosan.

Each dyed sample is loaded onto the FACs 3004 for counting. The sample can be run through a microfluidic chip with a specific size nozzle (e.g., 100 μm, selected depending on the implementation and application) that generates a stream of individual droplets (e.g., approximately $1/10^{th}$ of a microliter (0.1 μL)). These variables (nozzle size, droplet formation) can be optimized for each target microorganism type. Ideally, encapsulated in each droplet is one cell, or "event," and when each droplet is hit by a laser, anything that is dyed is excited and emits a different wavelength of light. The FACs optically detects each emission, and can plot them as events (e.g., on a 2D graph). A typical graph consists of one axis for size of event (determined by "forward scatter"), and the other for intensity of fluorescence. "Gates" can be drawn around discrete population on these graphs, and the events in these gates can be counted.

Figure 3C:
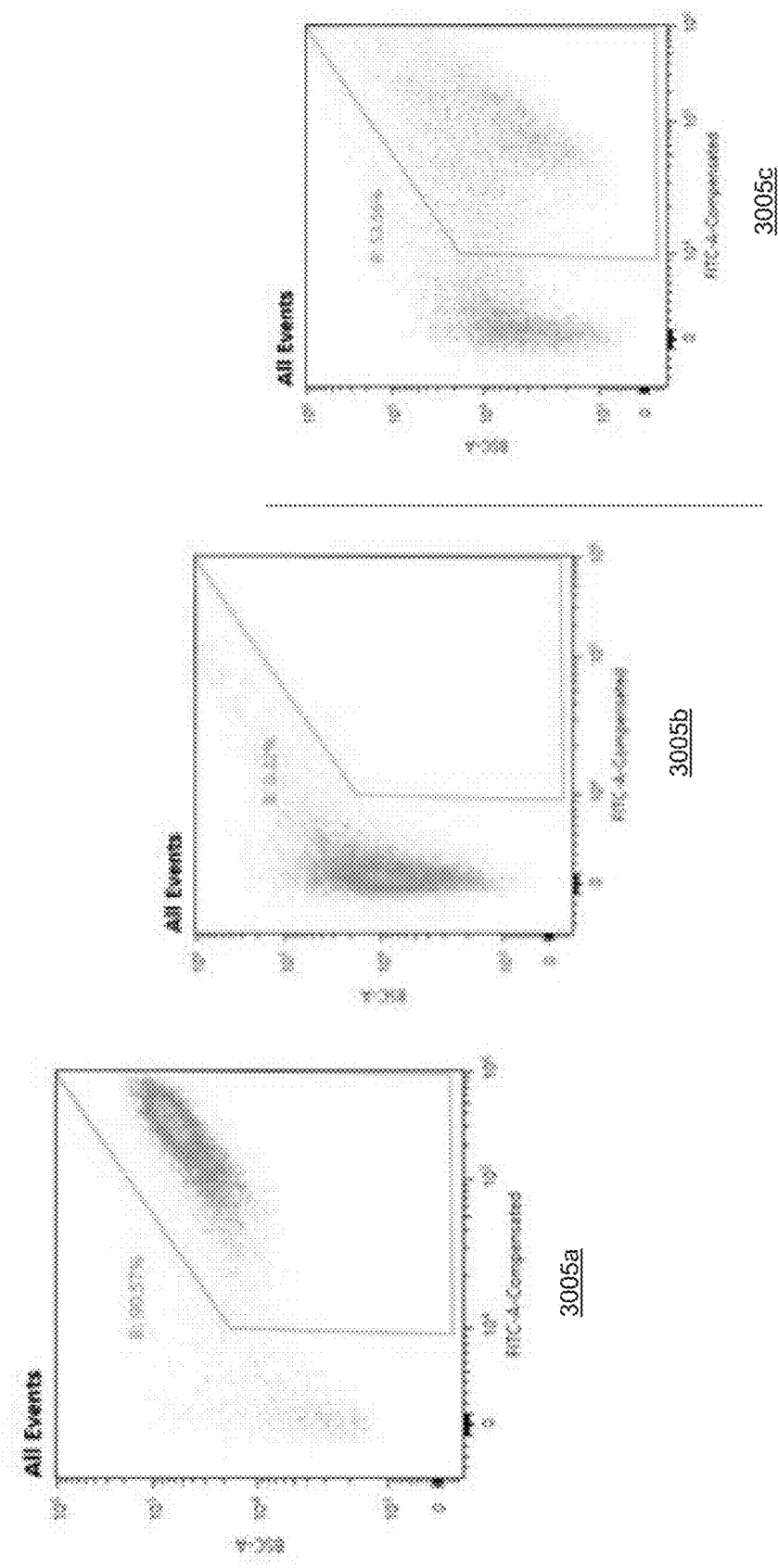
FIGS. 3C and 3D provides exemplary data illustrating some aspects of the disclosure.

FIG. 3C shows example data from fungi stained with Direct Yellow; includes yeast monoculture 3005*a* (positive control, left), *E. coli* 3005*b* (negative control, middle), and environmental sample 3005*c* (experimental, right). In the figure, "back scatter" (BSC-A) measures complexity of event, while FITC measures intensity of fluorescent emission from Direct Yellow. Each dot represents one event, and density of events is indicated by color change from green to red. Gate B indicates general area in which targeted events, in this case fungi stained with Direct Yellow, are expected to be found.

Returning to FIG. 3B, beginning with the two or more samples 3001 collected from one or more sources (including samples collected from an individual animal or single geographical location over time; from two or more groups differing in geography, breed, performance, diet, disease, etc.; from one or more groups that experience a physiological perturbation or event; and/or the like) the samples can be analyzed to establish absolute counts using flow cytometry, including staining 3002, as discussed above. Samples are weighed and serially diluted 3003, and processed using a FACs 3004. Output from the FACs is then processed to determine the absolute number of the desired organism type in each sample 3005. The following code fragment shows an exemplary methodology for such processing, according to one embodiment:

```
# User defined variables

# volume=volume of sample measured by FACs
# dilution=dilution factor
# beads_num=counting bead factor
# total_volume=total volume of sample (if applicable) in mL

# Note on total_volume: This is can be directly measured (i.e.
# rumen evacuation to measure entire volume content of the rumen),
# or via a stable tracer (i.e. use of an undigestible marker dosed
# in a known quantity in order to backcalculate volume of small
# intestine.)
Read FACsoutput as x
for i in range(len(x)):
    holder=x[i]
    mule=[ ]
    for j in range(len(holder)):
        beads=holder[−1]
        if beads==0:
            temp=(((holder[j]/beads_num)*(51300/volume))*1000)
                *dilution*100*total_volume
            mule.append(temp)
        else:
            temp=(((holder[j]holder[−1])*(51300/volume))*1000)*dilution*100*total_volume
            mule.append(temp)
        organism_type_1=mule[column_location]
        call=sample_names[i]
        cell_count=[call, organism_type_1]
savetxt(output_file,cell_count)
output_file.close( )
```

The total nucleic acids are isolated from each sample 3006. The nucleic acid sample elutate is split into two parts (typically, two equal parts), and each part is enzymatically purified to obtain either purified DNA 3006a or purified RNA 3006b. Purified RNA is stabilized through an enzymatic conversion to cDNA 3006c. Sequencing libraries (e.g., ILLUMINA sequencing libraries) are prepared for both the purified DNA and purified cDNA using PCR to attach the appropriate barcodes and adapter regions, and to amplify the marker region appropriate for measuring the desired organism type 3007. Library quality can be assessed and quantified, and all libraries can then be pooled and sequenced.

Raw sequencing reads are quality trimmed and merged 3008. Processed reads are dereplicated and clustered to generate a set or list of all of the unique strains present in the plurality of samples 3009. This set or list can be used for taxonomic identification of each strain present in the plurality of samples 3010. Sequencing libraries derived from DNA samples can be identified 3011, and sequencing reads from the identified DNA libraries are mapped back to the set or list of dereplicated strains in order to identity which strains are present in each sample, and quantify the number of reads for each strain in each sample 3012. The quantified read list is then integrated with the absolute cell count of target microorganism type in order to determine the absolute number or cell count of each strain 3013. The following code fragment shows an exemplary methodology for such processing, according to one embodiment:

```
# User defined variables

# input=quantified count output from sequence analysis
# count=calculated absolute cell count of organism type
# taxonomy=predicted taxonomy of each strain

Read absolute cell count file as counts
Read taxonomy file as tax
ncols=len(counts)
num_samples=ncols/2
tax_level=[ ]
tax_level.append(unique(taxonomy['kingdom'].values.ravel( )))
tax_level.append(unique(taxonomy['phylum'].values.ravel( )))
tax_level.append(unique(taxonomy['class'].values.ravel( )))
tax_level.append(unique(taxonomy['order'].values.ravel( )))
tax_level.append(unique(taxonomy['family'].values.ravel( )))
tax_level.append(unique(taxonomy['genus'].values.ravel( )))
tax_level.append(unique(taxonomy['species'].values.ravel( )))
tax_counts=merge(left=counts,right=tax)
# Species level analysis
tax_counts.to_csv('species.txt')
# Only pull DNA samples
data_mule=loadcsv('species.txt',    usecols=xrange(2, ncols,2))
data_mule_normalized=data_mule/sum(data_mule)
data_mule_with_counts=data_mule_normalized*counts
Repeat for every taxonomic level
```

Sequencing libraries derived from cDNA samples are identified 3014. Sequencing reads from the identified cDNA libraries are then mapped back to the list of dereplicated strains in order to determine which strains are active in each sample. If the number of reads is below a specified or designated threshold 3015, the strain is deemed or identified as inactive and is removed from subsequent analysis 3015a. If the number of reads exceeds the threshold 3015, the strain is deemed or identified as active and remains in the analysis 3015b. Inactive strains are then filtered from the output 3013 to generate a set or list of active strains and respective absolute numbers/cell counts for each sample 3016. The following code fragment shows an exemplary methodology for such processing, according to one embodiment:

```
# continued using variables from above
# Only pull RNA samples
active_data_mule=loadcsv('species.csv', usecols=xrange (3,ncols+1,2))
threshold=percentile(active_data_mule, 70)
for i in range(len(active_data_mule)):
    if data_mule_activity>=threshold
        multiplier[i]=1
    else
        multiplier[i]=0
active_data_mule_with_counts=multiplier*data_mule_with_counts
Repeat for every taxonomic level
```

Qualitative and quantitative metadata (e.g., environmental parameters, etc.) is identified, retrieved, and/or collected for each sample 3017 (set of samples, subsamples, etc.) and stored 3018 in a database (e.g., 319). Appropriate metadata can be identified, and the database is queried to pull identified and/or relevant metadata for each sample being analyzed 3019, depending on the application/implementation. The subset of metadata is then merged with the set or list of active strains and their corresponding absolute numbers/cell counts to create a large species and metadata by sample matrix 3020.

The maximal information coefficient (MIC) is then calculated between strains and metadata 3021a, and between strains 3021b. Results are pooled to create a set or list of all relationships and their corresponding MIC scores 3022. If the relationship scores below a given threshold 3023, the relationship is deemed/identified as irrelevant 3023b. If the relationship is above a given threshold 3023, the relationship deemed/identified as relevant 3023a, and is further subject to network analysis 3024. The following code fragment shows an exemplary methodology for such analysis, according to one embodiment:

Read total list of relationships file as links
threshold=0.8
for i in range(len(links)):
    if links>=threshold
        multiplier[i]=1
    else
        multiplier[i]=0
    end if
links_temp=multiplier*links
final_links=links_temp[links_temp !=0]
savetxt(output_file,final_links)
output_file.close( )

Based on the output of the network analysis, active strains are selected 3025 for preparing products (e.g., ensembles, aggregates, and/or other synthetic groupings) containing the selected strains. The output of the network analysis can also be used to inform the selection of strains for further product composition testing.

The use of thresholds is discussed above for analyses and determinations. Thresholds can be, depending on the implementation and application: (1) empirically determined (e.g., based on distribution levels, setting a cutoff at a number that removes a specified or significant portion of low level reads); (2) any non-zero value; (3) percentage/percentile based; (4) only strains whose normalized second marker (i.e., activity) reads is greater than normalized first marker (cell count) reads; (5) log 2 fold change between activity and quantity or cell count; (6) normalized second marker (activity) reads is greater than mean second marker (activity) reads for entire sample (and/or sample set); and/or any magnitude threshold described above in addition to a statistical threshold (i.e., significance testing). The following example provides thresholding detail for distributions of RNA-based second marker measurements with respect to DNA-based first marker measurements, according to one embodiment.

The small intestine contents of one male Cobb500 was collected and subjected to analysis according to the disclosure. Briefly, the total number of bacterial cells in the sample was determined using FACs (e.g., 3004). Total nucleic acids were isolated (e.g., 3006) from the fixed small intestine sample. DNA (first marker) and cDNA (second marker) sequencing libraries were prepared (e.g., 3007), and loaded onto an ILLUMINA MISEQ. Raw sequencing reads from each library were quality filtered, dereplicated, clustered, and quantified (e.g., 3008). The quantified strain lists from both the DNA-based and cDNA-based libraries were integrated with the cell count data to establish the absolute number of cells of each strain within the sample (e.g., 3013). Although cDNA is not necessarily a direct measurement of strain quantity (i.e., highly active strains may have many copies of the same RNA molecule), the cDNA-based library was integrated with cell counting data in this example to maintain the same normalization procedure used for the DNA library.

Figure 3D:
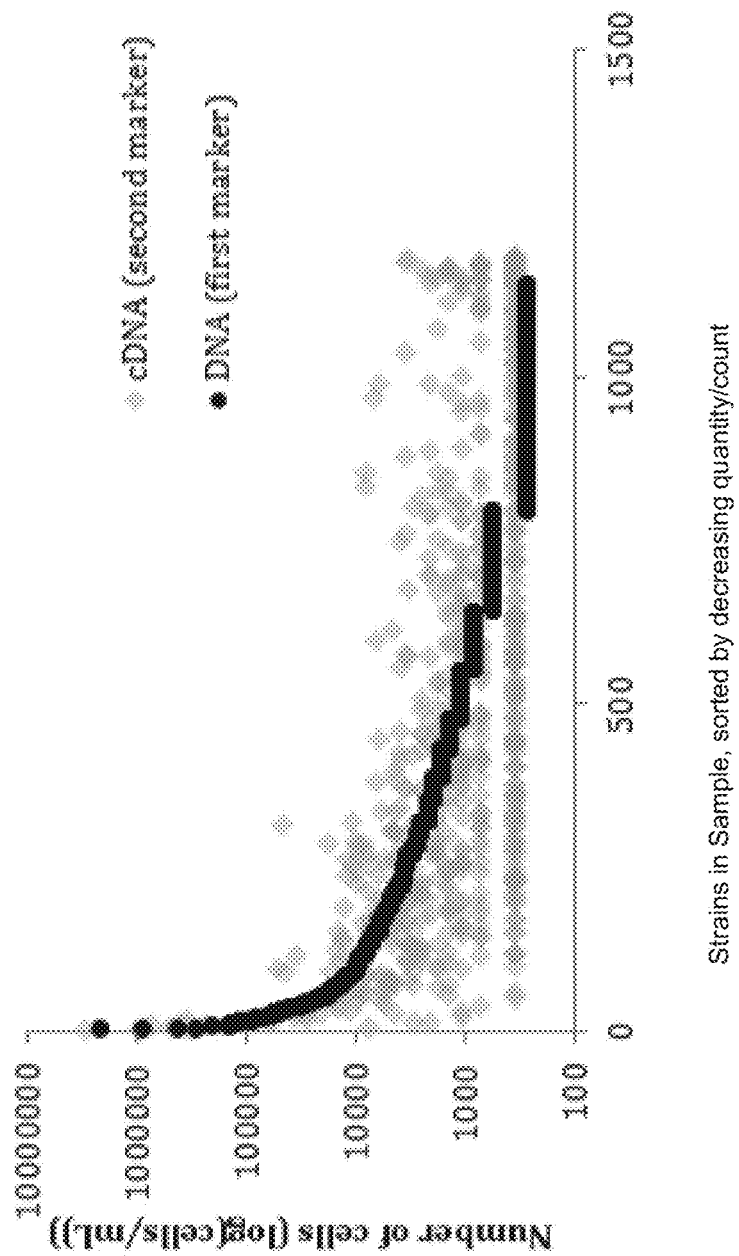

After analysis, 702 strains (46 unique) were identified in the cDNA-based library and 1140 strains were identified in the DNA-based library. If using 0 as the activity threshold (i.e. keeping any nonzero value), 57% of strains within this sample that had a DNA-based first marker were also associated with a cDNA-based second marker. These strains are identified as/deemed the active portion of the microbial community, and only these strains continue into subsequent analysis. If the threshold is made more stringent and only strains whose second marker value exceed the first marker value are considered active, only 289 strains (25%) meet the threshold. The strains that meet this threshold correspond to those above the DNA (first marker) line in FIG. 3D.

The disclosure includes a variety of methods identifying a plurality of active microbe strains that influence each other as well as one or more parameters or metadata, and selecting identified microbes for use in a microbial ensemble that includes a select subset of a microbial community of individual microbial species, or strains of a species, that are linked in carrying out or influence a common function, or can be described as participating in, or leading to, or associated with, a recognizable parameter, such as a phenotypic trait of interest (e.g. increased milk production in a ruminant). The disclosure also includes a variety of systems and apparatuses that perform and/or facilitate the methods.

In some embodiments, the method, comprises: obtaining at least two samples sharing at least one common characteristic (such as sample geolocation, sample type, sample source, sample source individual, sample target animal, sample time, breed, diet, temperature, etc.) and having a least one different characteristic (such as sample geolocation/temporal location, sample type, sample source, sample source individual, sample target animal, sample time, breed, diet, temperature, etc., different from the common characteristic). For each sample, detecting the presence of one or more microorganism types, determining a number of each detected microorganism type of the one or more microorganism types in each sample; and measuring a number of unique first markers in each sample, and quantity thereof, each unique first marker being a marker of a microorganism strain. This is followed by integrating the number of each microorganism type and the number of the first markers to yield the absolute cell count of each microorganism strain present in each sample; measuring at least one unique second marker for each microorganism strain based on a specified threshold to determine an activity level for that microorganism strain in each sample; filtering the absolute cell count by the determined activity to provide a set or list of active microorganisms strains and their respective absolute cell counts for each of the at least two samples; comparing the filtered absolute cell counts of active microorganisms strains for each of the at least two samples with each other and with at least one measured metadata for each of the at least two samples and categorizing the active microorganism strains into one of at least two groups, at least three groups, at least four groups, at least five groups, at least six groups, at least seven groups, at least eight groups, at least nine groups, at least 10 groups, at least 15 groups, at least 20 groups, at least 25 groups, at least 50 groups, at least 75 groups, or at least 100 groups, based on predicted function and/or chemistry. For example, the comparison can be network analysis that identifies the ties between the respective microbial strains and between each microbial strain and metadata, and/or between the metadata and the microbial strains. At least one microorganism can be selected from the at least two groups, and combined to form an ensemble of microorganisms configured to alter a property corresponding to the at least one metadata (e.g., a property in a target, such as milk production in a cow or cow population). Forming the ensemble can include isolating the microorganism strain or each microorganism strain, selecting a previously isolated microorganism strain based on the analysis, and/or incubating/growing specific microorganism strains based on the analysis, and combining the strains, including at particular amounts/counts and/or ratios and/or media/carrier(s) based on the application, to form the microbial ensemble. The ensemble can include an appropriate medium, carrier, and/or pharmaceutical carrier that enables delivery of the microorganisms in the ensemble in such a way that they can influence the recipient (e.g., increase milk production).

Measurement of the number of unique first markers can include measuring the number of unique genomic DNA markers in each sample, measuring the number of unique RNA markers in each sample, measuring the number of unique protein markers in each sample, and/or measuring the number of unique metabolite markers in each sample (including measuring the number of unique lipid markers in each sample and/or measuring the number of unique carbohydrate markers in each sample).

In some embodiments, measuring the number of unique first markers, and quantity thereof, includes subjecting genomic DNA from each sample to a high throughput sequencing reaction and/or subjecting genomic DNA from each sample to metagenome sequencing. The unique first markers can include at least one of an mRNA marker, an siRNA marker, and/or a ribosomal RNA marker. The unique first markers can additionally or alternatively include at least one of a sigma factor, a transcription factor, nucleoside associated protein, and/or metabolic enzyme.

In some embodiments, measuring the at least one unique second marker includes measuring a level of expression of the at least one unique second marker in each sample, and can include subjecting mRNA in the sample to gene expression analysis. The gene expression analysis can include a sequencing reaction, a quantitative polymerase chain reaction (qPCR), metatranscriptome sequencing, and/or transcriptome sequencing.

In some embodiments, measuring the level of expression of the at least one unique second marker includes subjecting each sample or a portion thereof to mass spectrometry analysis and/or subjecting each sample or a portion thereof to metaribosome profiling, or ribosome profiling. The one or more microorganism types includes bacteria, archaea, fungi, protozoa, plant, other eukaryote, viruses, viroids, or a combination thereof, and the one or more microorganism strains includes one or more bacterial strains, archaeal strains, fungal strains, protozoa strains, plant strains, other eukaryote strains, viral strains, viroid strains, or a combination thereof. The one or more microorganism strains can be one or more fungal species or sub-species, and/or the one or more microorganism strains can be one or more bacterial species or sub-species.

In some embodiments, determining the number of each of the one or more microorganism types in each sample includes subjecting each sample or a portion thereof to sequencing, centrifugation, optical microscopy, fluorescent microscopy, staining, mass spectrometry, microfluidics, quantitative polymerase chain reaction (qPCR), gel electrophoresis, and/or flow cytometry.

Unique first markers can include a phylogenetic marker comprising a 5S ribosomal subunit gene, a 16S ribosomal subunit gene, a 23S ribosomal subunit gene, a 5.8S ribosomal subunit gene, a 18S ribosomal subunit gene, a 28S ribosomal subunit gene, a cytochrome c oxidase subunit gene, a β-tubulin gene, an elongation factor gene, an RNA polymerase subunit gene, an internal transcribed spacer (ITS), or a combination thereof. Measuring the number of unique markers, and quantity thereof, can include subjecting genomic DNA from each sample to a high throughput sequencing reaction, subjecting genomic DNA to genomic sequencing, and/or subjecting genomic DNA to amplicon sequencing.

In some embodiments, the at least one different characteristic includes: a collection time at which each of the at least two samples was collected, such that the collection time for a first sample is different from the collection time of a second sample, a collection location (either geographical location difference and/or individual sample target/animal collection differences) at which each of the at least two samples was collected, such that the collection location for a first sample is different from the collection location of a second sample. The at least one common characteristic can include a sample source type, such that the sample source type for a first sample is the same as the sample source type of a second sample. The sample source type can be one of animal type, organ type, soil type, water type, sediment type, oil type, plant type, agricultural product type, bulk soil type, soil rhizosphere type, plant part type, and/or the like. In some embodiments, the at least one common characteristic includes that each of the at least two samples are gastrointestinal samples, which can be, in some implementations, ruminal samples. In some implementations, the common/different characteristics provided herein can be, instead, different/common characteristics between certain samples. In some embodiments, the at least one common characteristic includes animal sample source type, each sample having a further common characteristic such that each sample is a tissue sample, a blood sample, a tooth sample, a perspiration sample, a fingernail sample, a skin sample, a hair sample, a feces sample, a urine sample, a semen sample, a mucus sample, a saliva sample, a muscle sample, a brain sample, or an organ sample.

In some embodiments, the above method can further comprise obtaining at least one further sample from a target, based on the at least one measured metadata, wherein the at least one further sample from the target shares at least one common characteristic with the at least two samples. Then, for the at least one further sample from the target, detecting the presence of one or more microorganism types, determining a number of each detected microorganism type of the one or more microorganism types, measuring a number of unique first markers and quantity thereof, integrating the number of each microorganism type and the number of the first markers to yield the absolute cell count of each microorganism strain present, measuring at least one unique second marker for each microorganism strain to determine an activity level for that microorganism strain, filtering the absolute cell count by the determined activity to provide a set or list of active microorganisms strains and their respective absolute cell counts for the at least one further sample from the target. In such embodiments, the selection of the at least one microorganism strain from the at least two groups is based on the set or list of active microorganisms strain(s) and the/their respective absolute cell counts for the at least one further sample from the target such that the formed ensemble is configured to alter a property of the target that corresponds to the at least one metadata. For example, using such an implementation, a microbial ensemble could be identified from samples taken from Holstein cows, and a target sample taken from a Jersey cow or water buffalo, where the analysis identified the same, substantially similar, or similar network relationships between the same or similar microorganism strains from the original sample and the target sample(s).

In some embodiments, comparing the filtered absolute cell counts of active microorganisms strains for each of the at least two samples with at least one measured metadata or additional active microorganism strain for each of the at least two samples includes determining the co-occurrence of the one or more active microorganism strains in each sample with the at least one measured metadata or additional active microorganism strain. The at least one measured metadata can include one or more parameters, wherein the one or more parameters is at least one of sample pH, sample temperature, abundance of a fat, abundance of a protein, abundance of a carbohydrate, abundance of a mineral, abundance of a vitamin, abundance of a natural product, abundance of a specified compound, bodyweight of the sample source, feed intake of the sample source, weight gain of the sample source, feed efficiency of the sample source, presence or absence of one or more pathogens, physical characteristic(s) or measurement(s) of the sample source, production characteristics of the sample source, or a combination thereof. Parameters can also include abundance of whey protein, abundance of casein protein, and/or abundance of fats in milk produced by the sample source.

In some embodiments, determining the co-occurrence of the one or more active microorganism strains and the at least one measured metadata or additional active microorganism strain in each sample can include creating matrices populated with linkages denoting metadata and microorganism strain associations in two or more sample sets, the absolute cell count of the one or more active microorganism strains and the measure of the one or more unique second markers to represent one or more networks of a heterogeneous microbial community or communities. Determining the co-occurrence of the one or more active microorganism strains and the at least one measured metadata or additional active microorganism strain and categorizing the active microorganism strains can include network analysis and/or cluster analysis to measure connectivity of each microorganism strain within a network, the network representing a collection of the at least two samples that share a common characteristic, measured metadata, and/or related environmental parameter. The network analysis and/or cluster analysis can include linkage analysis, modularity analysis, robustness measures, betweenness measures, connectivity measures, transitivity measures, centrality measures, or a combination thereof. The cluster analysis can include building a connectivity model, subspace model, distribution model, density model, and/or a centroid model. Network analysis can, in some implementations, include predictive modeling of network(s) through link mining and prediction, collective classification, link-based clustering, relational similarity, a combination thereof, and/or the like. The network analysis can comprise differential equation based modeling of populations and/or Lotka-Volterra modeling. The analysis can be a heuristic method. In some embodiments, the analysis can be the Louvain method. The network analysis can include nonparametric methods to establish connectivity between variables, and/or mutual information and/or maximal information coefficient calculations between variables to establish connectivity.

For some embodiments, the method for forming an ensemble of active microorganism strains configured to alter a property or characteristic in an environment based on two or more sample sets that share at least one common or related environmental parameter between the two or more sample sets and that have at least one different environmental parameter between the two or more sample sets, each sample set comprising at least one sample including a heterogeneous microbial community, wherein the one or more microorganism strains is a subtaxon of one or more organism types, comprises: detecting the presence of a plurality of microorganism types in each sample; determining the absolute number of cells of each of the detected microorganism types in each sample; and measuring the number of unique first markers in each sample, and quantity thereof, wherein a unique first marker is a marker of a microorganism strain. Then, at the protein or RNA level, measuring the level of expression of one or more unique second markers, wherein a unique second marker is a marker of activity of a microorganism strain, determining activity of the detected microorganism strains for each sample based on the level of expression of the one or more unique second markers exceeding a specified threshold, calculating the absolute cell count of each detected active microorganism strains in each sample based upon the quantity of the one or more first markers and the absolute number of cells of the microorganism types from which the one or more microorganism strains is a subtaxon, wherein the one or more active microorganism strains expresses the second unique marker above the specified threshold. The co-occurrence of the active microorganism strains in the samples with at least one environmental parameter is then determined based on maximal information coefficient network analysis to measure connectivity of each microorganism strain within a network, wherein the network is the collection of the at least two or more sample sets with at least one common or related environmental parameter. A plurality of active microorganism strains from the one or more active microorganism strains is selected based on the network analysis, and an ensemble of active microorganism strains is formed from the selected plurality of active microorganism strains, the ensemble of active microorganism strains configured to selectively alter a property or characteristic of an environment when the ensemble of active microorganism strains is introduced into that environment. For some implementations, at least one measured indicia of at least one common or related environmental factor for a first sample set is different from a measured indicia of the at least one common or related environmental factor for a second sample set. For example, if the samples/sample sets are from cows, the first sample set can be from cows fed on a grass diet, while the second sample set can be from cows fed on a corn diet. While one sample set could be a single sample, it could alternatively be a plurality of samples, and a measured indicia of at least one common or related environmental factor for each sample within a sample set is substantially similar (e.g., samples in one set all taken from a herd on grass feed), and an average measured indicia for one sample set is different from the average measured indicia from another sample set (first sample set is from a herd on grass feed, and the second sample set is samples from a herd on corn feed). There may be additional difference and similarities that are taken into account in the analysis, such as differing breeds, differing diets, differing performance, differing age, differing feed additives, differing growth stage, differing physiological characteristics, differing state of health, differing elevations, differing environmental temperatures, differing season, different antibiotics, etc. While in some embodiments each sample set comprises a plurality of samples, and a first sample set is collected from a first population and a second sample set is collected from a second population, in additional or alternative embodiments, each sample set comprises a plurality of samples, and a first sample set is collected from a first population at a first time and a second sample set is collected from the first population at a second time different from the first time. For example, the first sample set could be taken at a first time from a herd of cattle while they were being feed on grass, and a second sample set could be taken at a second time (e.g., 2 months later), where the herd had been switched over to corn feed right after the first sample set was taken. In such embodiments, the samples can be collected and the analysis performed on the population, and/or can include specific reference to individual animals so that the changes that happened to individual animals over the time period could be identified, and a finer level of data granularity provided. In some embodiments, a method for forming a synthetic ensemble of active microorganism strains configured to alter a property in a biological environment, based on two or more samples (or sample sets, each set comprising at least one sample), each having a plurality of environmental parameters (and/or metadata), at least one parameter of the plurality of environmental parameters being a common environmental parameter that is similar between the two or more samples or sample sets and at least one environmental parameter being a different environmental parameter that is different between each of the two or more samples or sample sets, each sample set including at least one sample comprising a heterogeneous microbial community obtained from a biological sample source, at least one of the active microorganism strains being a subtaxon of one or more organism types, comprises: detecting the presence of a plurality of microorganism types in each sample; determining the absolute number of cells of each of the detected microorganism types in each sample; measuring the number of unique first markers in each sample, and quantity thereof, a unique first marker being a marker of a microorganism strain; measuring the level (e.g., level of expression) of one or more unique second markers, wherein a unique second marker is a marker of activity of a microorganism strain; determining activity of each of the detected microorganism strains for each sample based on the level (e.g., level of expression) of the one or more unique second markers exceeding a specified threshold to identify one or more active microorganism strains; calculating the absolute cell count of each detected active microorganism strain in each sample from the quantity (relative quantity, proportional number, proportional quantity, percentage quantity, etc.) of each of the one or more unique first markers and the absolute number of cells of the respective or corresponding microorganism types from which the one or more microorganism strains is a subtaxon (wherein the calculating is mathematical function such as multiplication, dot operator, and/or other operation), the one or more active microorganism strains having or expressing one or more unique second markers above the specified threshold; analyzing the active microorganism strains of the two or more sample sets, the analyzing including conducting nonparametric network analysis of each of the active microorganism strains for each of the two or more sample sets, the at least one common environmental parameter, and the at least one different environmental parameter, the nonparametric network analysis including determining the maximal information coefficient score between each active microorganism strain and every other active microorganism strain and determining the maximal information coefficient score between each active microorganism strain and the at least one different environmental parameter; selecting a plurality of active microorganism strains from the one or more active microorganism strains based on the nonparametric network analysis; and forming a synthetic ensemble of active microorganism strains comprising the selected plurality of active microorganism strains and a microbial carrier medium, the ensemble of active microorganism strains configured to selectively alter a property of a biological environment when the synthetic ensemble of active microorganism strains is introduced into that biological environment. Depending on the embodiment or implementation, the at least two samples or sample sets can comprise three samples, four samples, five samples, six samples, seven samples, eight samples, nine samples, ten samples, eleven samples, twelve samples, thirteen samples, fourteen samples, fifteen samples, sixteen samples, seventeen samples, eighteen samples, nineteen samples, twenty samples, twenty one samples, twenty two samples, twenty three samples, twenty four samples, twenty five samples, twenty six samples, twenty seven samples, twenty eight samples, twenty nine samples, thirty samples, thirty five samples, forty samples, forty five samples, fifty samples, sixty samples, seventy samples, eighty samples, ninety samples, one hundred samples, one hundred fifty samples, two hundred samples, three hundred samples, four hundred samples, five hundred samples, six hundred samples, and/or the like. The total number of samples can, depending on the embodiment/implementation, can be less than 5, from 5 to 10, 10 to 15, 15 to 20, 20 to 30, 30 to 40, 40 to 50, 50 to 60, 60 to 70, 70 to 80, 80 to 90, 90 to 100, less than 100, more than 100, less than 200 more than 200, less than 300, more than 300, less than 400, more than 400, less than 500, more than 500, less than 1000, more than 1000, less than 5000, less than 10000, less than 20000, and so forth.

In some embodiments, at least one common or related environmental factor includes nutrient information, dietary information, animal characteristics, infection information, health status, and/or the like.

The at least one measured indicia can include sample pH, sample temperature, abundance of a fat, abundance of a protein, abundance of a carbohydrate, abundance of a mineral, abundance of a vitamin, abundance of a natural product, abundance of a specified compound, bodyweight of the sample source, feed intake of the sample source, weight gain of the sample source, feed efficiency of the sample source, presence or absence of one or more pathogens, physical characteristic(s) or measurement(s) of the sample source, production characteristics of the sample source, abundance of whey protein in milk produced by the sample source, abundance of casein protein produced by the sample source, and/or abundance of fats in milk produced by the sample source, or a combination thereof.

Measuring the number of unique first markers in each sample can, depending on the embodiment, comprise measuring the number of unique genomic DNA markers, measuring the number of unique RNA markers, and/or measuring the number of unique protein markers. The plurality of microorganism types can include one or more bacteria, archaea, fungi, protozoa, plant, other eukaryote, virus, viroid, or a combination thereof.

In some embodiments, determining the absolute number of each of the microorganism types in each sample includes subjecting the sample or a portion thereof to sequencing, centrifugation, optical microscopy, fluorescent microscopy, staining, mass spectrometry, microfluidics, quantitative polymerase chain reaction (qPCR), gel electrophoresis and/or flow cytometry. In some embodiments, one or more active microorganism strains is a subtaxon of one or more microbe types selected from one or more bacteria, archaea, fungi, protozoa, plant, other eukaryote, virus, viroid, or a combination thereof. In some embodiments, one or more active microorganism strains is one or more bacterial strains, archaeal strains, fungal strains, protozoa strains, plant strains, other eukaryote strains, viral strains, viroid strains, or a combination thereof. In some embodiments, one or more active microorganism strains is one or more bacterial species or subspecies. In some embodiments, one or more active microorganism strains is one or more fungal species or subspecies.

In some embodiments, at least one unique first marker comprises a phylogenetic marker comprising a 5S ribosomal subunit gene, a 16S ribosomal subunit gene, a 23S ribosomal subunit gene, a 5.8S ribosomal subunit gene, a 18S ribosomal subunit gene, a 28S ribosomal subunit gene, a cytochrome c oxidase subunit gene, a beta-tubulin gene, an elongation factor gene, an RNA polymerase subunit gene, an internal transcribed spacer (ITS), or a combination thereof.

In some embodiments, measuring the number of unique first markers, and quantity thereof, comprises subjecting genomic DNA from each sample to a high throughput sequencing reaction, and/or subjecting genomic DNA from each sample to metagenome sequencing. In some implementations, unique first markers can include an mRNA marker, an siRNA marker, and/or a ribosomal RNA marker. In some implementations, unique first markers can include a sigma factor, a transcription factor, nucleoside associated protein, metabolic enzyme, or a combination thereof.

In some embodiments, measuring the level of expression of one or more unique second markers comprises subjecting mRNA in each sample to gene expression analysis, and in some implementations, gene expression analysis comprises a sequencing reaction. In some implementations, the gene expression analysis comprises a quantitative polymerase chain reaction (qPCR), metatranscriptome sequencing, and/or transcriptome sequencing.

In some embodiments, measuring the level of expression of one or more unique second markers includes subjecting each sample or a portion thereof to mass spectrometry analysis, metaribosome profiling, and/or ribosome profiling.

In some embodiments, measuring the level of expression of the at least one or more unique second markers includes subjecting each sample or a portion thereof to metaribosome profiling or ribosome profiling (Ribo-Seq) (see, e.g., Ingolia, N. T., S. Ghaemmaghami, J. R. Newman, and J. S. Weissman, 2009, "Genome-wide analysis in vivo of translation with nucleotide resolution using ribosome profiling" Science 324:218-223; Ingolia, N. T., 2014, "Ribosome profiling: new views of translation, from single codons to genome scale" Nat. Rev. Genet. 15:205-213; each of which is incorporated by reference in it entirety for all purposes). Ribo-seq is a molecular technique that can be used to determine in vivo protein synthesis at the genome-scale. This method directly measures which transcripts are being actively translated via footprinting ribosomes as they bind and interact with mRNA. The bound mRNA regions are then processed and subjected to high-throughput sequencing reactions. Ribo-seq has been shown to have a strong correlation with quantitative proteomics (see, e.g., Li, G. W., D. Burkhardt, C. Gross, and J. S. Weissman. 2014 "Quantifying absolute protein synthesis rates reveals principles underlying allocation of cellular resources" Cell 157:624-635, the entirety of which is herein expressly incorporated by reference).

The source type for the samples can be one of animal, soil, air, saltwater, freshwater, wastewater sludge, sediment, oil, plant, an agricultural product, bulk soil, soil rhizosphere, plant part, vegetable, an extreme environment, or a combination thereof. In some implementations, each sample is a digestive tract and/or ruminal sample. In some implementations, samples can be tissue samples, blood samples, tooth samples, perspiration samples, fingernail samples, skin samples, hair samples, feces samples, urine samples, semen samples, mucus samples, saliva samples, muscle samples, brain samples, tissue samples, and/or organ samples.

Depending on the implementation, a microbial ensemble of the disclosure can comprise two or more substantially pure microbes or microbe strains, a mixture of desired microbes/microbe strains, and can also include any additional components that can be administered to a target, e.g., for restoring microbiota to an animal. Microbial ensembles made according to the disclosure can be administered with an agent to allow the microbes to survive a target environment (e.g., the gastrointestinal tract of an animal, where the ensemble is configured to resist low pH and to grow in the gastrointestinal environment). In some embodiments, microbial ensembles can include one or more agents that increase the number and/or activity of one or more desired microbes or microbe strains, said strains being present or absent from the microbes/strains included in the ensemble. Non-limiting examples of such agents include fructooligosaccharides (e.g., oligofructose, inulin, inulin-type fructans), galactooligosaccharides, amino acids, alcohols, and mixtures thereof (see Ramirez-Farias et al. 2008. Br. J. Nutr. 4:1-10 and Pool-Zobel and Sauer 2007. J. Nutr. 137:2580-2584 and supplemental, each of which is herein incorporated by reference in their entireties for all purposes).

Microbial strains identified by the methods of the disclosure can be cultured/grown prior to inclusion in an ensemble. Media can be used for such growth, and can include any medium suitable to support growth of a microbe, including, by way of non-limiting example, natural or artificial including gastrin supplemental agar, LB media, blood serum, and/or tissue culture gels. It should be appreciated that the media can be used alone or in combination with one or more other media. It can also be used with or without the addition of exogenous nutrients. The medium can be modified or enriched with additional compounds or components, for example, a component which may assist in the interaction and/or selection of specific groups of microorganisms and/or strains thereof. For example, antibiotics (such as penicillin) or sterilants (for example, quaternary ammonium salts and oxidizing agents) could be present and/or the physical conditions (such as salinity, nutrients (for example organic and inorganic minerals (such as phosphorus, nitrogenous salts, ammonia, potassium and micronutrients such as cobalt and magnesium), pH, and/or temperature) could be modified.

As discussed above, systems and apparatuses can be configured according to the disclosure, and in some embodiments, can comprise a processor and memory, the memory storing processor-readable/issuable instructions to perform the method(s). In one embodiment, a system and/or apparatus are configured to perform the method. Also disclosed are processor-implementations of the methods, as discussed with reference to FIG. 3A. For example, a processor-implemented method, can comprise: receiving sample data from at least two samples sharing at least one common characteristic and having a least one different characteristic; for each sample, determining the presence of one or more microorganism types in each sample; determining a number of cells of each detected microorganism type of the one or more microorganism types in each sample; determining a number of unique first markers in each sample, and quantity thereof, each unique first marker being a marker of a microorganism strain; integrating, via one or more processors, the number of each microorganism type and the number of the first markers to yield the absolute cell count of each microorganism strain present in each sample; determining an activity level for each microorganism strain in each sample based on a measure of at least one unique second marker for each microorganism strain exceeding a specified threshold, a microorganism strain being identified as active if the measure of at least one unique second marker for that strain exceeds the corresponding threshold; filtering the absolute cell count of each microorganism strain by the determined activity to provide a list of active microorganisms strains and their respective absolute cell counts for each of the at least two samples; analyzing via one or more processors the filtered absolute counts of active microorganisms strains for each of the at least two samples with at least one measured metadata or additional active microorganism strain for each of the at least two samples and categorizing the active microorganism strains based on function, predicted function, and/or chemistry; identifying a plurality of active microorganism strains based on the categorization; and outputting the identified plurality of active microorganism strains for assembling an active microorganism ensemble configured to, when applied to a target, alter a property of the target corresponding to the at least one measured metadata. In some embodiments, the output can be utilized in the generation, synthesis, evaluation, and/or testing of synthetic and/or transgenic microbes and microbe strains. Some embodiments can include a processor-readable non-transitory computer readable medium that stores instructions for performing and/or facilitating execution of the method(s). In some embodiments, analysis and screening methods, apparatuses, and systems according to the disclosure can be used for identifying problematic microorganisms and strains, such as pathogens, as discussed in Example 4 below. In such situations, a known symptom metadata, such as lesion score, would be used in the network analysis of the samples.

It is intended that the systems and methods described herein can be performed by software (stored in memory and/or executed on hardware), hardware, or a combination thereof. Hardware components and/or modules can include, for example, a general-purpose processor, a field programmable gate array (FPGA), and/or an application specific integrated circuit (ASIC). Software components and/or modules (executed on hardware) can be expressed in a variety of software languages (e.g., computer code), including Unix utilities, C, C++, Java™, JavaScript (e.g., ECMAScript 6), Ruby, SQL, SAS®, the R programming language/software environment, Visual Basic™, and other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

Some embodiments described herein relate to devices with a non-transitory computer-readable medium (also can be referred to as a non-transitory processor-readable medium or memory) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing components and/or modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

While various embodiments of FIG. 3A have been described above, it should be understood that they have been presented by way of example only, and not limitation. Where methods and steps described above indicate certain events occurring in certain order, the ordering of certain steps can be modified. Additionally, certain of the steps can be performed concurrently in a parallel process when possible, as well as performed sequentially as described above. Although various embodiments have been described as having particular features and/or combinations of components, other embodiments are possible having any combination or sub-combination of any features and/or components from any of the embodiments described herein. Furthermore, although various embodiments are described as having a particular entity associated with a particular compute device, in other embodiments different entities can be associated with other and/or different compute devices.

EXPERIMENTAL DATA AND EXAMPLES

The present disclosure is further illustrated by reference to the following Experimental Data and Examples. However, it should be noted that these Experimental Data and Examples, like the embodiments described above, are illustrative and are not to be construed as restricting the scope of the disclosure in any way.

Example 1

Reference is made to steps provided at FIG. 2.

2000: Cells from a cow rumen sample are sheared off matrix. This can be done via blending or mixing the sample vigorously through sonication or vortexing followed by differential centrifugation for matrix removal from cells. Centrifugation can include a gradient centrifugation step using Nycodenz or Percoll.

2001: Organisms are stained using fluorescent dyes that target specific organism types. Flow cytometry is used to discriminate different populations based on staining properties and size.

2002: The absolute number of organisms in the sample is determined by, for example, flow cytometry. This step yields information about how many organism types (such as bacteria, archaea, fungi, viruses or protists) are in a given volume.

2003: A cow rumen sample is obtained and cells adhered to matrix are directly lysed via bead beating. Total nucleic acids are purified. Total purified nucleic acids are treated with RNAse to obtain purified genomic DNA (gDNA). qPCR is used to simultaneously amplify specific markers from the bulk gDNA and to attach sequencing adapters and barcodes to each marker. The qPCR reaction is stopped at the beginning of exponential amplification to minimize PCR-related bias. Samples are pooled and multiplexed sequencing is performed on the pooled samples using an Illumina Miseq.

2004: Cells from a cow rumen sample adhered to matrix are directly lysed via bead beating. Total nucleic acids are purified using a column-based approach. Total purified nucleic acids are treated with DNAse to obtain purified RNA. Total RNA is converted to cDNA using reverse transcriptase. qPCR is used to simultaneously amplify specific markers from the bulk cDNA and to attach sequencing adapters and barcodes to each marker. The qPCR reaction is stopped at the beginning of exponential amplification to minimize PCR-related bias. Samples are pooled and multiplexed sequencing is performed on the pooled samples using an Illumina Miseq.

2005: Sequencing output (fastq files) is processed by removing low quality base pairs and truncated reads. DNA-based datasets are analyzed using a customized UPARSE pipeline, and sequencing reads are matched to existing database entries to identify strains within the population. Unique sequences are added to the database. RNA-based datasets are analyzed using a customized UPARSE pipeline. Active strains are identified using an updated database.

2006: Using strain identity data obtained in the previous step (2005), the number of reads representing each strain is determined and represented as a percentage of total reads. The percentage is multiplied by the counts of cells (2002) to calculate the absolute cell count of each organism type in a sample and a given volume. Active strains are identified within absolute cell count datasets using the marker sequences present in the RNA-based datasets along with an appropriate threshold. Strains that do not meet the threshold are removed from analysis.

2007: Repeat 2003-2006 to establish time courses representing the dynamics of microbial populations within multiple cow rumens. Compile temporal data and store the number of cells of each active organism strain and metadata for each sample in a quantity or abundance matrix. Use quantity matrix to identify associations between active strains in a specific time point sample using rule mining approaches weighted with quantity data. Apply filters to remove insignificant rules.

2008: Calculate cell number changes of active strains over time, noting directionality of change (i.e., negative values denoting decreases, positive values denoting increases). Represent matrix as a network, with organism strains representing nodes and the quantity weighted rules representing edges. Leverage markov chains and random walks to determine connectivity between nodes and to define clusters. Filter clusters using metadata in order to identify clusters associated with desirable metadata (environmental parameter(s)). Rank target organism strains by integrating cell number changes over time and strains present in target clusters, with highest changes in cell number ranking the highest.

Example 2

Experimental Design and Materials and Methods

Objective:

Determine rumen microbial community constituents that impact the production of milk fat in dairy cows.

Animals:

Eight lactating, ruminally cannulated, Holstein cows were housed in individual tie-stalls for use in the experiment. Cows were fed twice daily, milked twice a day, and had continuous access to fresh water. One cow (cow 1) was removed from the study after the first dietary Milk Fat Depression due to complications arising from an abortion prior to the experiment.

Experimental Design and Treatment:

The experiment used a crossover design with 2 groups and 1 experimental period. The experimental period lasted 38 days: 10 days for the covariate/wash-out period and 28 days for data collection and sampling. The data collection period consisted of 10 days of dietary Milk Fat Depression (MFD) and 18 days of recovery. After the first experimental period, all cows underwent a 10-day wash out period prior to the beginning of period 2.

Dietary MFD was induced with a total mixed ration (TMR) low in fiber (29% NDF) with high starch degradability (70% degradable) and high polyunsaturated fatty acid levels (PUFA, 3.7%). The Recovery phase included two diets variable in starch degradability. Four cows were randomly assigned to the recovery diet high in fiber (37% NDF), low in PUFA (2.6%), and high in starch degradability (70% degradable). The remaining four cows were fed a recovery diet high in fiber (37% NDF), low in PUFA (2.6%), but low in starch degradability (35%).

During the 10-day covariate and 10-day wash out periods, cows were fed the high fiber, low PUFA, and low starch degradability diet.

Samples and Measurements:

Milk yield, dry matter intake, and feed efficiency were measured daily for each animal throughout the covariate, wash out, and sample collection periods. TMR samples were measured for nutrient composition. During the collection period, milk samples were collected and analyzed every 3 days. Samples were analyzed for milk component concentrations (milk fat, milk protein, lactose, milk urea nitrogen, somatic cell counts, and solids) and fatty acid compositions.

Rumen samples were collected and analyzed for microbial community composition and activity every 3 days during the collection period. The rumen was intensively sampled 0, 2, 4, 6, 8, 10, 12, 14, 16, 18, 20, and 22 hours after feeding during day 0, day 7, and day 10 of the dietary MFD. Similarly, the rumen was intensively sampled 0, 2, 4, 6, 8, 10, 12, 14, 16, 18, 20, and 22 hours after feeding on day 16 and day 28 during the recovery period. Rumen contents were analyzed for pH, acetate concentration, butyrate concentration, propionate concentration, isoacid concentration, and long chain and CLA isomer concentrations.

Rumen Sample Preparation and Sequencing: After collection, rumen samples were centrifuged at 4,000 rpm in a swing bucket centrifuge for 20 minutes at 4° C. The supernatant was decanted, and an aliquot of each rumen content sample (1-2 mg) was added to a sterile 1.7 mL tube prefilled with 0.1 mm glass beads. A second aliquot was collected and stored in an empty, sterile 1.7 mL tube for cell counting.

Rumen samples with glass beads (1st aliquot) were homogenized with bead beating to lyse microorganisms. DNA and RNA was extracted and purified from each sample and prepared for sequencing on an Illumina Miseq. Samples were sequenced using paired-end chemistry, with 300 base pairs sequenced on each end of the library. Rumen samples in empty tubes (2nd aliquot) were stained and put through a flow cytometer to quantify the number of cells of each microorganism type in each sample.

Sequencing Read Processing and Data Analysis:

Sequencing reads were quality trimmed and processed to identify bacterial species present in the rumen based on a marker gene. Count datasets and activity datasets were integrated with the sequencing reads to determine the absolute cell numbers of active microbial species within the rumen microbial community. Production characteristics of the cow over time, including pounds of milk produced, were linked to the distribution of active microorganisms within each sample over the course of the experiment using mutual information. Maximal information coefficient (MIC) scores were calculated between pounds of milk fat produced and the absolute cell count of each active microorganism. Microorganisms were ranked by MIC score, and microorganisms with the highest MIC scores were selected as the target species most relevant to pounds of milk produced.

Tests cases to determine the impact of count data, activity data, and count and activity on the final output were run by omitting the appropriate datasets from the sequencing analysis. To assess the impact of using a linear correlation rather than the MIC on target selection, Pearson's coefficients were also calculated for pounds of milk fat produced as compared to the relative abundance of all microorganisms and the absolute cell count of active microorganisms.

Results and Discussion

Relative Abundances vs. Absolute Cell Counts

The top 15 target species were identified for the dataset that included cell count data (absolute cell count, Table 2) and for the dataset that did not include cell count data (relative abundance, Table 1) based on MIC scores. Activity data was not used in this analysis in order to isolate the effect of cell count data on final target selection. Ultimately, the top 8 targets were the same between the two datasets. Of the remaining 7, 5 strains were present on both lists in varying order. Despite the differences in rank for these 5 strains, the calculated MIC score for each strain was the identical between the two lists. The two strains present on the absolute cell count list but not the relative abundance list, ascus 111 and ascus 288, were rank 91 and rank 16, respectively, on the relative abundance list. The two strains present on the relative abundance list but not the absolute cell count list, ascus 102 and ascus 252, were rank 50 and rank 19, respectively, on the absolute cell count list. These 4 strains did have different MIC scores on each list, thus explaining their shift in rank and subsequent impact on the other strains in the list.

TABLE 1

Top 15 Target Strains using Relative Abundance with no Activity Filter

| Target Strain | MIC | Nearest Taxonomy |
|---|---|---|
| ascus_7 | 0.97384 | d: Bacteria(1.0000), p: Firmicutes(0.9922), c: Clostridia(0.8756), o: Clostridiales(0.5860), f: Ruminococcaceae(0.3217), g: *Ruminococcus*(0.0605) |
| ascus_82 | 0.97173 | d: Bacteria(1.0000), p: Firmicutes(0.8349), c: Clostridia(0.5251), o: Clostridiales(0.2714), f: Ruminococcaceae(0.1062), g: *Saccharofermentans*(0.0073) |
| ascus_209 | 0.95251 | d: Bacteria(1.0000), p: TM7(0.9991), g: TM7_genera_incertae_sedis(0.8645) |
| ascus_126 | 0.91477 | d: Bacteria(1.0000), p: Firmicutes(0.8349), c: Clostridia(0.5251), o: Clostridiales(0.2714), f: Ruminococcaceae(0.1242), g: *Saccharofermentans*(0.0073) |
| ascus_1366 | 0.89713 | d: Bacteria(1.0000), p: TM7(0.9445), g: TM7_genera_incertae_sedis(0.0986) |
| ascus_1780 | 0.89466 | d: Bacteria(0.9401), p: Bacteroidetes(0.4304), c: Bacteroidia(0.0551), o: Bacteroidales(0.0198), f: Prevotellaceae(0.0067), g: *Prevotella*(0.0052) |
| ascus_64 | 0.89453 | d: Bacteria(1.0000), p: Firmicutes(0.9922), c: Clostridia(0.8823), o: Clostridiales(0.6267), f: Ruminococcaceae(0.2792), g: *Ruminococcus*(0.0605) |
| ascus_299 | 0.88979 | d: Bacteria(1.0000), p: TM7(0.9963), g: TM7_genera_incertae_sedis(0.5795) |
| ascus_102 | 0.87095 | d: Bacteria(1.0000), p: Firmicutes(0.9628), c: Clostridia(0.8317), o: Clostridiales(0.4636), f: Ruminococcaceae(0.2367), g: *Saccharofermentans*(0.0283) |
| ascus_1801 | 0.87038 | d: Bacteria(0.8663), p: Bacteroidetes(0.2483), c: Bacteroidia(0.0365), o: Bacteroidales(0.0179), f: Porphyromonadaceae(0.0059), g: *Butyricimonas*(0.0047) |
| ascus_295 | 0.86724 | d: Bacteria(1.0000), p: SR1(0.9990), g: SR1_genera_incertae_sedis(0.9793) |
| ascus_1139 | 0.8598 | d: Bacteria(1.0000), p: TM7(0.9951), g: TM7_genera_incertae_sedis(0.4747) |
| ascus_127 | 0.84082 | d: Bacteria(1.0000), p: TM7(0.9992), g: TM7_genera_incertae_sedis(0.8035) |
| ascus_341 | 0.8348 | d: Bacteria(1.0000), p: TM7(0.9992), g: TM7_genera_incertae_sedis(0.8035) |
| ascus_252 | 0.82891 | d: Bacteria(1.0000), p: Firmicutes(0.9986), c: Clostridia(0.9022), o: Clostridiales(0.7491), f: Lachnospiraceae(0.3642), g: Lachnospiracea_incertae_sedis(0.0859) |

TABLE 2

Top 15 Target Strains using Absolute cell count with no Activity Filter

| Target Strain | MIC | Nearest Taxonomy |
|---|---|---|
| ascus_7 | 0.97384 | d: Bacteria(1.0000), p: Firmicutes(0.9922), c: Clostridia(0.8756), o: Clostridiales(0.5860), f: Ruminococcaceae(0.3217), g: *Ruminococcus*(0.0605) |
| ascus_82 | 0.97173 | d: Bacteria(1.0000), p: Firmicutes(0.8349), c: Clostridia(0.5251), o: Clostridiales(0.2714), f: Ruminococcaceae(0.1062), g: *Saccharofermentans*(0.0073) |

TABLE 2-continued

Top 15 Target Strains using Absolute cell count with no Activity Filter

| Target Strain | MIC | Nearest Taxonomy |
|---|---|---|
| ascus_209 | 0.95251 | d: Bacteria(1.0000), p: TM7(0.9991), g: TM7_genera_incertae_sedis(0.8645) |
| ascus_126 | 0.91701 | d: Bacteria(1.0000), p: Firmicutes(0.8349), c: Clostridia(0.5251), o: Clostridiales(0.2714), f: Ruminococcaceae(0.1242), g: *Saccharofermentans*(0.0073) |
| ascus_1366 | 0.89713 | d: Bacteria(1.0000), p: TM7(0.9445), g: TM7_genera_incertae_sedis(0.0986) |
| ascus_1780 | 0.89466 | d: Bacteria(0.9401), p: Bacteroidetes(0.4304), c: Bacteroidia(0.0551), o: Bacteroidales(0.0198), f: Prevotellaceae(0.0067), g: *Prevotella*(0.0052) |
| ascus_64 | 0.89453 | d: Bacteria(1.0000), p: Firmicutes(0.9922), c: Clostridia(0.8823), o: Clostridiales(0.6267), f: Ruminococcaceae(0.2792), g: *Ruminococcus*(0.0605) |
| ascus_299 | 0.88979 | d: Bacteria(1.0000), p: TM7(0.9963), g: TM7_genera_incertae_sedis(0.5795) |
| ascus_1801 | 0.87038 | d: Bacteria(0.8663), p: Bacteroidetes(0.2483), c: Bacteroidia(0.0365), o: Bacteroidales(0.0179), f: Porphyromonadaceae(0.0059), g: *Butyricimonas*(0.0047) |
| ascus_295 | 0.86724 | d: Bacteria(1.0000), p: SR1(0.9990), g: SR1_genera_incertae_sedis(0.9793) |
| ascus_1139 | 0.8598 | d: Bacteria(1.0000), p: TM7(0.9951), g: TM7_genera_incertae_sedis(0.4747) |
| ascus_127 | 0.84082 | d: Bacteria(1.0000), p: TM7(0.9992), g: TM7_genera_incertae_sedis(0.8035) |
| ascus_341 | 0.8348 | d: Bacteria(1.0000), p: TM7(0.9992), g: TM7_genera_incertae_sedis(0.8035) |
| ascus_111 | 0.83358 | d: Bacteria(1.0000), p: Firmicutes(0.7947), c: Clostridia(0.4637), o: Clostridiales(0.2335), f: Ruminococcaceae(0.1062), g: *Papillibacter*(0.0098) |
| ascus_288 | 0.82833 | d: Bacteria(0.7925), p: Bacteroidetes(0.2030), c: Bacteroidia(0.0327), o: Bacteroidales(0.0160), f: Porphyromonadaceae(0.0050), g: *Butyricimonas*(0.0042) |

Integration of cell count data did not always affect the final MIC score assigned to each strain. This may be attributed to the fact that although the microbial population did shift within the rumen daily and over the course of the 38-day experiment, it was always within $10^7$-$10^8$ cells per milliliter. Much larger shifts in population numbers would undoubtedly have a broader impact on final MIC scores.

Inactive Species vs. Active Species

In order to assess the impact of filtering strains based on activity data, target species were identified from a dataset that leveraged relative abundance with (Table 3) and without (Table 1) activity data as well as a dataset that leveraged absolute cell counts with (Table 4) and without (Table 2) activity data.

For the relative abundance case, ascus_126, ascus_1366, ascus_1780, ascus_299, ascus_1139, ascus_127, ascus_341, and ascus_252 were deemed target strains prior to applying activity data. These eight strains (53% of the initial top 15 targets) fell below rank 15 after integrating activity data. A similar trend was observed for the absolute cell count case. Ascus_126, ascus_1366, ascus_1780, ascus_299, ascus_1139, ascus_127, and ascus_341 (46% of the initial top 15 targets) fell below rank 15 after activity dataset integration.

The activity datasets had a much more severe effect on target rank and selection than the cell count datasets. When integrating these datasets together, if a sample is found to be inactive it is essentially changed to a "0" and not considered to be part of the analysis. Because of this, the distribution of points within a sample can become heavily altered or skewed after integration, which in turn greatly impacts the final MIC score and thus the rank order of target microorganisms.

TABLE 3

Top 15 Target Strains using Relative Abundance with Activity Filter

| Target Strain | MIC | Nearest Taxonomy |
|---|---|---|
| ascus_7 | 0.97384 | d: Bacteria(1.0000), p: Firmicutes(0.9922), c: Clostridia(0.8756), o: Clostridiales(0.5860), f: Ruminococcaceae(0.3217), g: *Ruminococcus*(0.0605) |
| ascus_82 | 0.93391 | d: Bacteria(1.0000), p: Firmicutes(0.8349), c: Clostridia(0.5251), o: Clostridiales(0.2714), f: Ruminococcaceae(0.1062), g: *Saccharofermentans*(0.0073) |
| ascus_102 | 0.87095 | d: Bacteria(1.0000), p: Firmicutes(0.9628), c: Clostridia(0.8317), o: Clostridiales(0.4636), f: Ruminococcaceae(0.2367), g: *Saccharofermentans*(0.0283) |
| ascus_209 | 0.84421 | d: Bacteria(1.0000), p: TM7(0.9991), g: TM7_genera_incertae_sedis(0.8645) |
| ascus_1801 | 0.82398 | d: Bacteria(0.8663), p: Bacteroidetes(0.2483), c: Bacteroidia(0.0365), o: Bacteroidales(0.0179), f: Porphyromonadaceae(0.0059), g: *Butyricimonas*(0.0047) |
| ascus_372 | 0.81735 | d: Bacteria(1.0000), p: Spirochaetes(0.9445), c: Spirochaetes(0.8623), o: Spirochaetales(0.5044), f: Spirochaetaceae(0.3217), g: *Spirochaeta*(0.0190) |
| ascus_26 | 0.81081 | d: Bacteria(1.0000), p: Firmicutes(0.9080), c: Clostridia(0.7704), o: Clostridiales(0.4230), f: Ruminococcaceae(0.1942), g: *Clostridium*_IV(0.0144) |
| ascus_180 | 0.80702 | d: Bacteria(1.0000), p: Spirochaetes(0.9445), c: Spirochaetes(0.8623), o: Spirochaetales(0.5044), f: Spirochaetaceae(0.3217), g: *Spirochaeta*(0.0237) |
| ascus_32 | 0.7846 | d: Bacteria(1.0000), p: Firmicutes(0.7036), c: Clostridia(0.4024), o: Clostridiales(0.1956), f: Ruminococcaceae(0.0883), g: *Hydrogenoanaerobacterium*(0.0144) |
| ascus_288 | 0.78229 | d: Bacteria(0.7925), p: Bacteroidetes(0.2030), c: Bacteroidia(0.0327), o: Bacteroidales(0.0160), f: Porphyromonadaceae(0.0050), g: *Butyricimonas*(0.0042) |
| ascus_64 | 0.77514 | d: Bacteria(1.0000), p: Firmicutes(0.9922), c: Clostridia(0.8823), o: Clostridiales(0.6267), f: Ruminococcaceae(0.2792), g: *Ruminococcus*(0.0605) |
| ascus_295 | 0.76639 | d: Bacteria(1.0000), p: SR1(0.9990), g: SR1_genera_incertae_sedis(0.9793) |
| ascus_546 | 0.76114 | d: Bacteria(1.0000), p: Firmicutes(0.6126), c: Clostridia(0.2851), o: Clostridiales(0.1324), f: Clostridiaceae_1(0.0208), g: *Clostridium*_sensu_stricto(0.0066) |

TABLE 3-continued

Top 15 Target Strains using Relative Abundance with Activity Filter

| Target Strain | MIC | Nearest Taxonomy |
|---|---|---|
| ascus_233 | 0.75779 | d: Bacteria(1.0000), p: Firmicutes(0.9922), c: Clostridia(0.8756), o: Clostridiales(0.5860), f: Ruminococcaceae(0.3642), g: *Ruminococcus*(0.0478) |
| ascus_651 | 0.74837 | d: Bacteria(1.0000), p: Firmicutes(0.7947), c: Clostridia(0.4637), o: Clostridiales(0.2335), f: Ruminococcaceae(0.0883), g: *Clostridium*_IV(0.0069) |

TABLE 4

Top 15 Target Strains using Absolute cell count with Activity Filter

| Target Strain | MIC | Nearest Taxonomy |
|---|---|---|
| ascus_7 | 0.97384 | d: Bacteria(1.0000), p: Firmicutes(0.9922), c: Clostridia(0.8756), o: Clostridiales(0.5860), f: Ruminococcaceae(0.3217), g: *Ruminococcus*(0.0605) |
| ascus_82 | 0.93391 | d: Bacteria(1.0000), p: Firmicutes(0.8349), c: Clostridia(0.5251), o: Clostridiales(0.2714), f: Ruminococcaceae(0.1062), g: *Saccharofermentans*(0.0073) |
| ascus_209 | 0.84421 | d: Bacteria(1.0000), p: TM7(0.9991), g: TM7_genera_incertae_sedis(0.8645) |
| ascus_1801 | 0.82398 | d: Bacteria(0.8663), p: Bacteroidetes(0.2483), c: Bacteroidia(0.0365), o: Bacteroidales(0.0179), f: Porphyromonadaceae(0.0059), g: *Butyricimonas*(0.0047) |
| ascus_372 | 0.81735 | d: Bacteria(1.0000), p: Spirochaetes(0.9445), c: Spirochaetes(0.8623), o: Spirochaetales(0.5044), f: Spirochaetaceae(0.3217), g: *Spirochaeta*(0.0190) |
| ascus_26 | 0.81081 | d: Bacteria(1.0000), p: Firmicutes(0.9080), c: Clostridia(0.7704), o: Clostridiales(0.4230), f: Ruminococcaceae(0.1942), g: *Clostridium*_IV(0.0144) |
| ascus_102 | 0.81048 | d: Bacteria(1.0000), p: Firmicutes(0.9628), c: Clostridia(0.8317), o: Clostridiales(0.4636), f: Ruminococcaceae(0.2367), g: *Saccharofermentans*(0.0283) |
| ascus_111 | 0.79035 | d: Bacteria(1.0000), p: Firmicutes(0.7947), c: Clostridia(0.4637), o: Clostridiales(0.2335), f: Ruminococcaceae(0.1062), g: *Papillibacter*(0.0098) |
| ascus_288 | 0.78229 | d: Bacteria(0.7925), p: Bacteroidetes(0.2030), c: Bacteroidia(0.0327), o: Bacteroidales(0.0160), f: Porphyromonadaceae(0.0050), g: *Butyricimonas*(0.0042) |
| ascus_64 | 0.77514 | d: Bacteria(1.0000), p: Firmicutes(0.9922), c: Clostridia(0.8823), o: Clostridiales(0.6267), f: Ruminococcaceae(0.2792), g: *Ruminococcus*(0.0605) |
| ascus_295 | 0.76639 | d: Bacteria(1.0000), p: SR1(0.9990), g: SR1_genera_incertae_sedis(0.9793) |
| ascus_546 | 0.76114 | d: Bacteria(1.0000), p: Firmicutes(0.6126), c: Clostridia(0.2851), o: Clostridiales(0.1324), f: Clostridiaceae_1(0.0208), g: *Clostridium*_sensu_stricto(0.0066) |
| ascus_32 | 0.75068 | d: Bacteria(1.0000), p: Firmicutes(0.7036), c: Clostridia(0.4024), o: Clostridiales(0.1956), f: Ruminococcaceae(0.0883), g: *Hydrogenoanaerobacterium*(0.0144) |
| ascus_651 | 0.74837 | d: Bacteria(1.0000), p: Firmicutes(0.7947), c: Clostridia(0.4637), o: Clostridiales(0.2335), f: Ruminococcaceae(0.0883), g: *Clostridium*_IV(0.0069) |
| ascus_233 | 0.74409 | d: Bacteria(1.0000), p: Firmicutes(0.9922), c: Clostridia(0.8756), o: Clostridiales(0.5860), f: Ruminococcaceae(0.3642), g: *Ruminococcus*(0.0478) |

Relative Abundances and Inactive vs. Absolute Cell Counts and Active

Ultimately, the method defined here leverages both cell count data and activity data to identify microorganisms highly linked to relevant metadata characteristics. Within the top 15 targets selected using both methods (Table 4, Table 1), only 7 strains were found on both lists. Eight strains (53%) were unique to the absolute cell count and activity list. The top 3 targets on both lists matched in both strain as well as in rank. However, two of the three did not have the same MIC score on both lists, suggesting that they were influenced by activity dataset integration but not enough to upset their rank order.

Linear Correlations vs. Nonparametric Approaches

Pearson's coefficients and MIC scores were calculated between pounds of milk fat produced and the absolute cell count of active microorganisms within each sample (Table 5). Strains were ranked either by MIC (Table 5a) or Pearson coefficient (Table 5b) to select target strains most relevant to milk fat production. Both MIC score and Pearson coefficient are reported in each case. Six strains were found on both lists, meaning nine (60%) unique strains were identified using the MIC approach. The rank order of strains between lists did not match—the top 3 target strains identified by each method were also unique.

Figure 4:
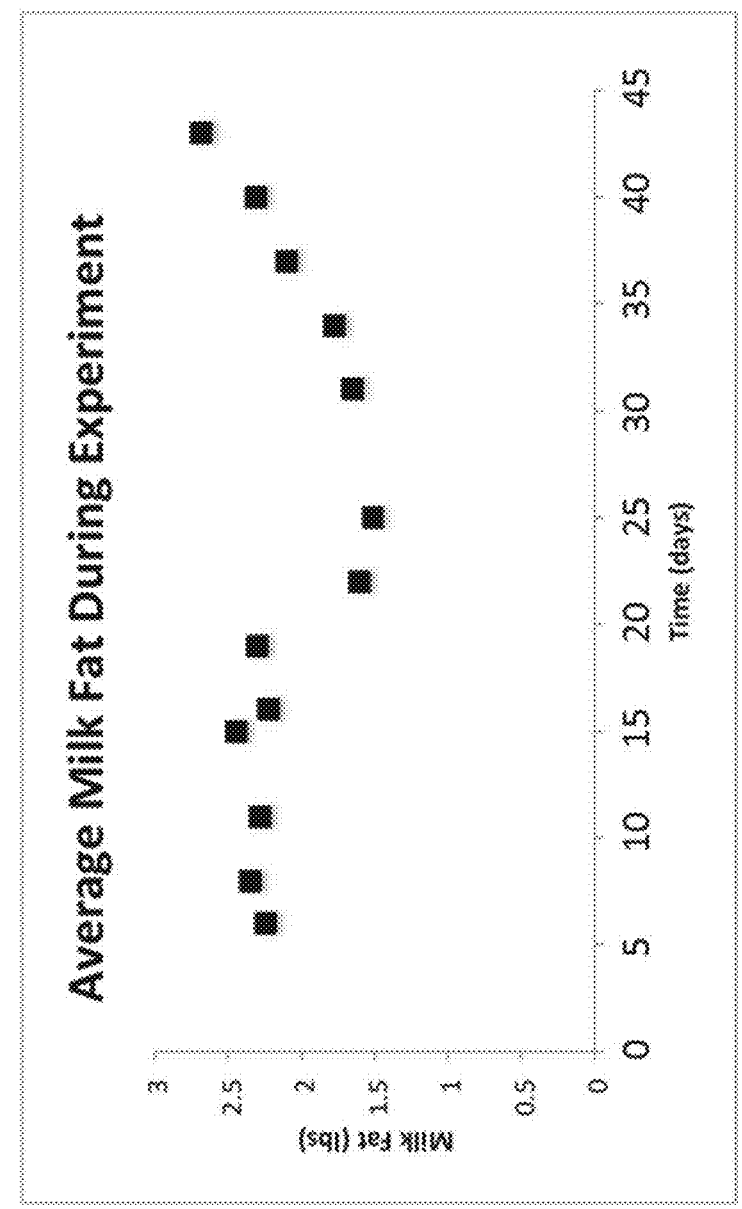
FIG. 4 shows the non-linearity of pounds of milk fat produced over the course of an experiment to determine rumen microbial community constituents that impact the production of milk fat in dairy cows.
Figure 5:
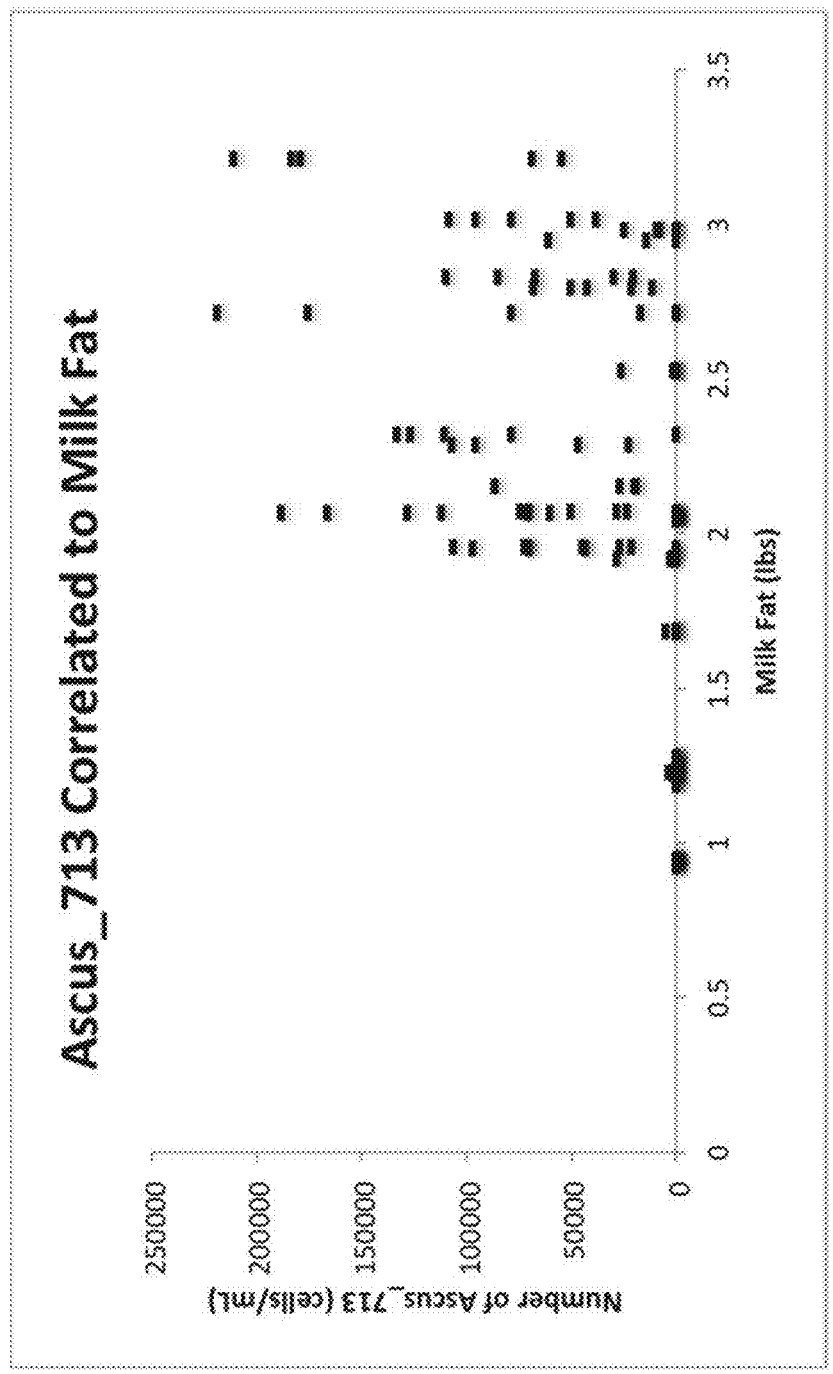
FIG. 5 shows the correlation of the absolute cell count with activity filter of target strain Ascus_713 to pounds (lbs) of milk fat produced.
Figure 6:
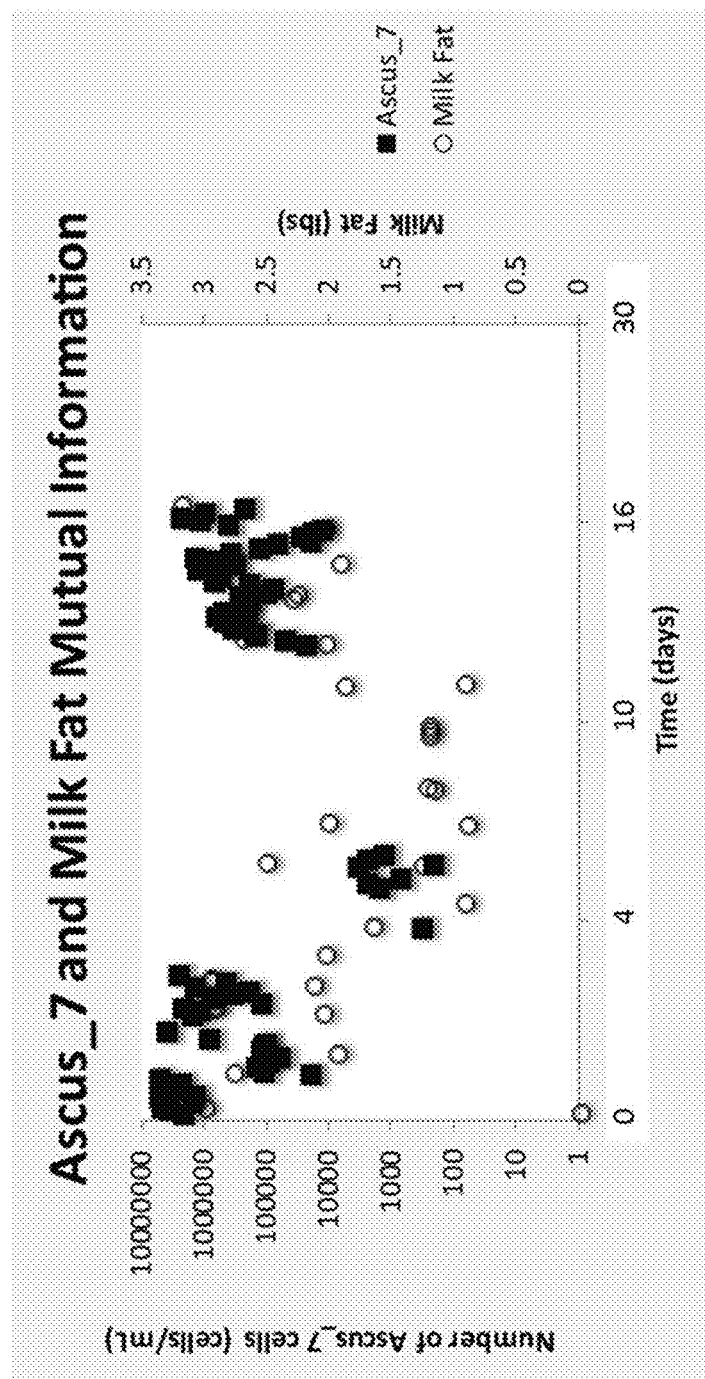
FIG. 6 shows the absolute cell count with activity filter of target strain Ascus_7 and the pounds (lbs) of milk fat produced over the course of an experiment.

Like Pearson coefficients, the MIC score is reported over a range of 0 to 1, with 1 suggesting a very tight relationship between the two variables. Here, the top 15 targets exhibited MIC scores ranging from 0.97 to 0.74. The Pearson coefficients for the correlation test case, however, ranged from 0.53 to 0.45—substantially lower than the mutual information test case. This discrepancy may be due to the differences inherent to each analysis method. While correlations are a linear estimate that measures the dispersion of points around a line, mutual information leverages probability distributions and measures the similarity between two distributions. Over the course of the experiment, the pounds of milk fat produced changed nonlinearly (FIG. 4). This particular function may be better represented and approximated by mutual information than correlations. To investigate this, the top target strains identified using correlation and mutual information, Ascus_713 (FIG. 5) and Ascus_7 (FIG. 6) respectively, were plotted to determine how well each method predicted relationships between the strains and milk fat. If two variables exhibit strong correlation, they are represented by a line with little to no dispersion of points when plotted against each other. In FIG. 5, Ascus_713 correlates weakly with milk fat, as indicated by the broad spread of points. Mutual information, again, measures how similar two distributions of points are. When Ascus_7 is plotted with milk fat (FIG. 6), it is apparent that the two point distributions are very similar.

The Present Method in Entirety vs. Conventional Approaches

Figure 7:
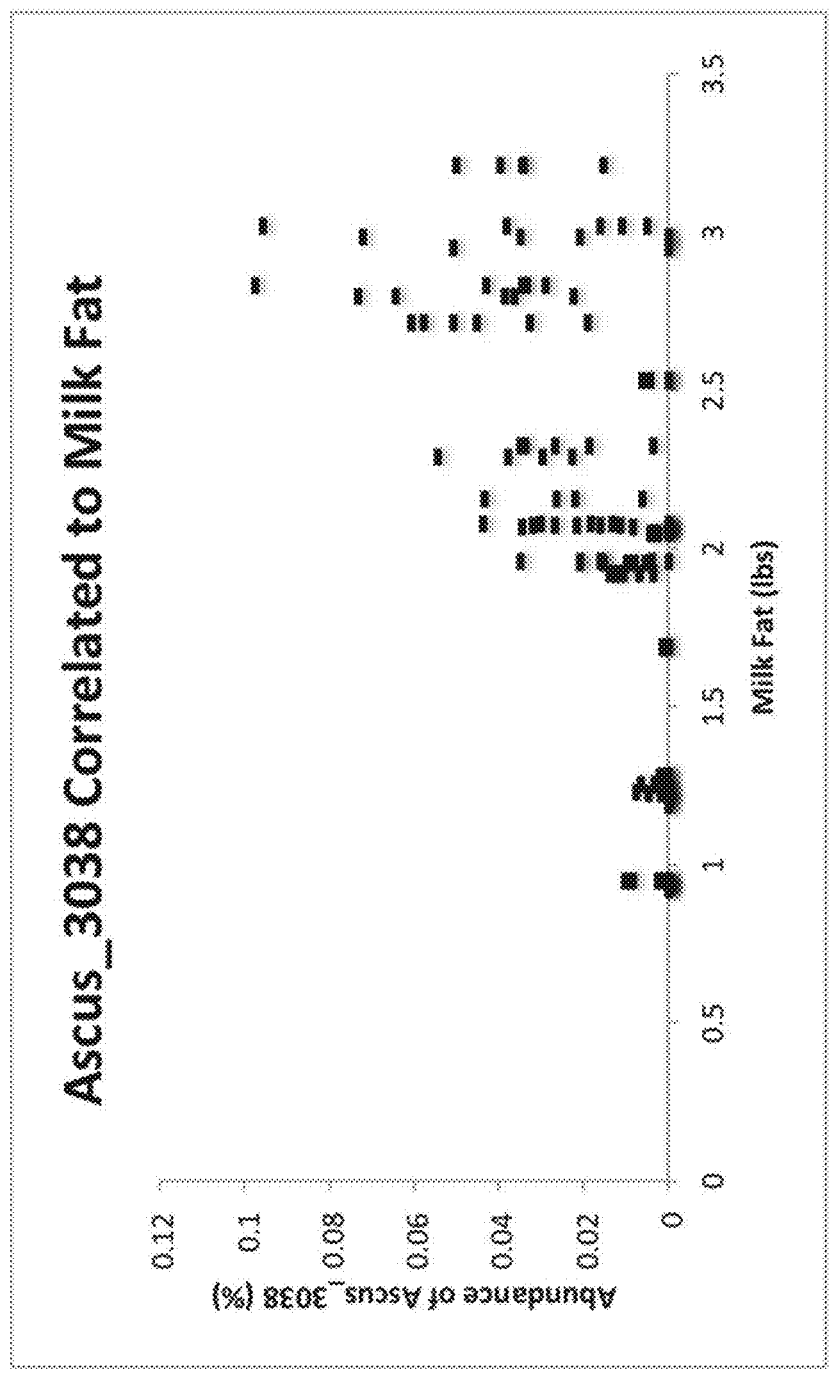
FIG. 7 shows the correlation of the relative abundance with no activity filter of target strain Ascus_3038 to pounds (lbs) of milk fat produced.

The conventional approach of analyzing microbial communities relies on the use of relative abundance data with no incorporation of activity information, and ultimately ends with a simple correlation of microbial species to metadata (see, e.g., U.S. Pat. No. 9,206,680, which is herein incorporated by reference in its entirety for all purposes). Here, we have shown how the incorporation of each dataset incrementally influences the final list of targets. When applied in its entirety, the method described herein selected a completely different set of targets when compared to the conventional method (Tables 5a and 5c). Ascus_3038, the top target strain selected using the conventional approach, was plotted against milk fat to visualize the strength of the correlation (FIG. 7). Like the previous example, Ascus_3038 also exhibited a weak correlation to milk fat.

Table 5: Top 15 Target Strains Using Mutual Information or Correlations

TABLE 5a

MIC using Absolute cell count with Activity Filter

| Target Strain | MIC | Pearson Coefficient | Nearest Taxonomy |
|---|---|---|---|
| ascus_7 | 0.97384 | 0.25282502 | d: Bacteria(1.0000), p: Firmicutes(0.9922), c: Clostridia(0.8756), o: Clostridiales(0.5860), f: Ruminococcaceae(0.3217), g: *Ruminococcus*(0.0605) |
| ascus_82 | 0.93391 | 0.42776647 | d: Bacteria(1.0000), p: Firmicutes(0.8349), c: Clostridia(0.5251), o: Clostridiales(0.2714), f: Ruminococcaceae(0.1062), g: *Saccharofermentans*(0.0073) |
| ascus_209 | 0.84421 | 0.3036308 | d: Bacteria(1.0000), p: TM7(0.9991), g: TM7_genera_incertae_sedis(0.8645) |
| ascus_1801 | 0.82398 | 0.5182261 | d: Bacteria(0.8663), p: Bacteroidetes(0.2483), c: Bacteroidia(0.0365), o: Bacteroidales(0.0179), f: Porphyromonadaceae(0.0059), g: *Butyricimonas*(0.0047) |
| ascus_372 | 0.81735 | 0.34172258 | d: Bacteria(1.0000), p: Spirochaetes(0.9445), c: Spirochaetes(0.8623), o: Spirochaetales(0.5044), f: Spirochaetaceae(0.3217), g: *Spirochaeta*(0.0190) |
| ascus_26 | 0.81081 | 0.5300298 | d: Bacteria(1.0000), p: Firmicutes(0.9080), c: Clostridia(0.7704), o: Clostridiales(0.4230), f: Ruminococcaceae(0.1942), g: *Clostridium*_IV(0.0144) |
| ascus_102 | 0.81048 | 0.35456932 | d: Bacteria(1.0000), p: Firmicutes(0.9628), c: Clostridia(0.8317), o: Clostridiales(0.4636), f: Ruminococcaceae(0.2367), g: *Saccharofermentans*(0.0283) |
| ascus_111 | 0.79035 | 0.45881805 | d: Bacteria(1.0000), p: Firmicutes(0.7947), c: Clostridia(0.4637), o: Clostridiales(0.2335), f: Ruminococcaceae(0.1062), g: *Papillibacter*(0.0098) |
| ascus_288 | 0.78229 | 0.46522045 | d: Bacteria(0.7925), p: Bacteroidetes(0.2030), c: Bacteroidia(0.0327), o: Bacteroidales(0.0160), f: Porphyromonadaceae(0.0050), g: *Butyricimonas*(0.0042) |
| ascus_64 | 0.77514 | 0.45417055 | d: Bacteria(1.0000), p: Firmicutes(0.9922), c: Clostridia(0.8823), o: Clostridiales(0.6267), f: Ruminococcaceae(0.2792), g: *Ruminococcus*(0.0605) |
| ascus_295 | 0.76639 | 0.24972263 | d: Bacteria(1.0000), p: SR1(0.9990), g: SR1_genera_incertae_sedis(0.9793) |
| ascus_546 | 0.76114 | 0.23819838 | d: Bacteria(1.0000), p: Firmicutes(0.6126), c: Clostridia(0.2851), o: Clostridiales(0.1324), f: Clostridiaceae_1(0.0208), g: *Clostridium*_sensu_stricto(0.0066) |
| ascus_32 | 0.75068 | 0.5179697 | d: Bacteria(1.0000), p: Firmicutes(0.7036), c: Clostridia(0.4024), o: Clostridiales(0.1956), f: Ruminococcaceae(0.0883), g: *Hydrogenoanaerobacterium*(0.0144) |
| ascus_651 | 0.74837 | 0.27656645 | d: Bacteria(1.0000), p: Firmicutes(0.7947), c: Clostridia(0.4637), o: Clostridiales(0.2335), f: Ruminococcaceae(0.0883), g: *Clostridium*_IV(0.0069) |
| ascus_233 | 0.74409 | 0.36095098 | d: Bacteria(1.0000), p: Firmicutes(0.9922), c: Clostridia(0.8756), o: Clostridiales(0.5860), f: Ruminococcaceae(0.3642), g: *Ruminococcus*(0.0478) |

TABLE 5b

Correlation using Absolute cell count with Activity Filter

| Target Strain | MIC | Pearson Coefficient | Nearest Taxonomy |
|---|---|---|---|
| ascus_713 | 0.71066 | 0.5305876 | d: Bacteria(1.0000), p: Firmicutes(0.8349), c: Clostridia(0.5251), o: Clostridiales(0.2714), f: Ruminococcaceae(0.1062), g: *Saccharofermentans*(0.0073) |
| ascus_26 | 0.81081 | 0.5300298 | d: Bacteria(1.0000), p: Firmicutes(0.9080), c: Clostridia(0.7704), o: Clostridiales(0.4230), f: Ruminococcaceae(0.1942), g: *Clostridium*_IV(0.0144) |
| ascus_1801 | 0.82398 | 0.5182261 | d: Bacteria(0.8663), p: Bacteroidetes(0.2483), c: Bacteroidia(0.0365), o: Bacteroidales(0.0179), f: Porphyromonadaceae(0.0059), g: *Butyricimonas*(0.0047) |
| ascus_32 | 0.75068 | 0.5179697 | d: Bacteria(1.0000), p: Firmicutes(0.7036), c: Clostridia(0.4024), o: Clostridiales(0.1956), f: Ruminococcaceae(0.0883), g: *Hydrogenoanaerobacterium*(0.0144) |
| ascus_119 | 0.6974 | 0.4968678 | d: Bacteria(1.0000), p: Firmicutes(0.9922), c: Clostridia(0.8756), o: Clostridiales(0.5860), f: Ruminococcaceae(0.3217), g: *Ruminococcus*(0.0478) |
| ascus_13899 | 0.64556 | 0.48739454 | d: Bacteria(1.0000), p: Actinobacteria(0.1810), c: Actinobacteria(0.0365), o: Actinomycetales(0.0179), f: Propionibacteriaceae(0.0075), g: *Microlunatus*(0.0058) |
| ascus_906 | 0.49256 | 0.48418677 | d: Bacteria(1.0000), p: Firmicutes(0.8349), c: Clostridia(0.5251), o: Clostridiales(0.2714), f: Ruminococcaceae(0.1242), g: *Papillibacter*(0.0098) |
| ascus_221 | 0.44006 | 0.47305903 | d: Bacteria(1.0000), p: Bacteroidetes(0.9991), c: Bacteroidia(0.9088), o: Bacteroidales(0.7898), f: Prevotellaceae(0.3217), g: *Prevotella*(0.0986) |
| ascus_1039 | 0.65629 | 0.46932846 | d: Bacteria(1.0000), p: Firmicutes(0.7036), c: Clostridia(0.2851), o: Clostridiales(0.1324), f: Ruminococcaceae(0.0329), g: *Clostridium*_IV(0.0069) |

TABLE 5b-continued

Correlation using Absolute cell count with Activity Filter

| Target Strain | MIC | Pearson Coefficient | Nearest Taxonomy |
|---|---|---|---|
| ascus_288 | 0.78229 | 0.46522045 | d: Bacteria(0.7925), p: Bacteroidetes(0.2030), c: Bacteroidia(0.0327), o: Bacteroidales(0.0160), f: Porphyromonadaceae(0.0050), g: *Butyricimonas*(0.0042) |
| ascus_589 | 0.40868 | 0.4651165 | d: Bacteria(1.0000), p: Firmicutes(0.9981), c: Clostridia(0.9088), o: Clostridiales(0.7898), f: Lachnospiraceae(0.5986), g: *Clostridium*_XIVa(0.3698) |
| ascus_41 | 0.67227 | 0.46499047 | d: Bacteria(1.0000), p: Firmicutes(0.6126), c: Clostridia(0.3426), o: Clostridiales(0.1618), f: Ruminococcaceae(0.0703), g: *Hydrogenoanaerobacterium*(0.0098) |
| ascus_111 | 0.79035 | 0.45881805 | d: Bacteria(1.0000), p: Firmicutes(0.7947), c: Clostridia(0.4637), o: Clostridiales(0.2335), f: Ruminococcaceae(0.1062), g: *Papillibacter*(0.0098) |
| ascus_205 | 0.72441 | 0.45684373 | d: Bacteria(1.0000), p: Firmicutes(0.6126), c: Clostridia(0.3426), o: Clostridiales(0.1618), f: Peptococcaceae_2(0.0449), g: *Pelotomaculum*(0.0069) |
| ascus_64 | 0.77514 | 0.45417055 | d: Bacteria(1.0000), p: Firmicutes(0.9922), c: Clostridia(0.8823), o: Clostridiales(0.6267), f: Ruminococcaceae(0.2792), g: *Ruminococcus*(0.0605) |

TABLE 5c

Correlation using Relative Abundance with no Activity Filter

| Target Strain | MIC | Pearson Coefficient | Nearest Taxonomy |
|---|---|---|---|
| ascus_3038 | 0.56239 | 0.6007549 | d: Bacteria(1.0000), p: Firmicutes(0.9945), c: Clostridia(0.8623), o: Clostridiales(0.5044), f: Lachnospiraceae(0.2367), g: *Clostridium*_XIVa(0.0350) |
| ascus_1555 | 0.66965 | 0.59716415 | d: Bacteria(1.0000), p: Firmicutes(0.7947), c: Clostridia(0.3426), o: Clostridiales(0.1618), f: Ruminococcaceae(0.0449), g: *Clostridium*_IV(0.0073) |
| ascus_1039 | 0.68563 | 0.59292555 | d: Bacteria(1.0000), p: Firmicutes(0.7036), c: Clostridia(0.2851), o: Clostridiales(0.1324), f: Ruminococcaceae(0.0329), g: *Clostridium*_IV(0.0069) |
| ascus_1424 | 0.55509 | 0.57589555 | d: Bacteria(1.0000), p: Firmicutes(0.8897), c: Clostridia(0.7091), o: Clostridiales(0.3851), f: Ruminococcaceae(0.1422), g: *Papillibacter*(0.0144) |
| ascus_378 | 0.77519 | 0.5671971 | d: Bacteria(1.0000), p: Firmicutes(0.8349), c: Clostridia(0.5251), o: Clostridiales(0.2714), f: Ruminococcaceae(0.1062), g: *Saccharofermentans*(0.0073) |
| ascus_407 | 0.69783 | 0.56279755 | d: Bacteria(1.0000), p: Firmicutes(0.7036), c: Clostridia(0.3426), o: Clostridiales(0.1618), f: Clostridiaceae_1(0.0329), g: *Clostridium*_sensu_stricto(0.0069) |
| ascus_1584 | 0.5193 | 0.5619939 | d: Bacteria(1.0000), p: Firmicutes(0.9945), c: Clostridia(0.8756), o: Clostridiales(0.5860), f: Lachnospiraceae(0.3217), g: *Coprococcus*(0.0605) |
| ascus_760 | 0.61363 | 0.55807924 | d: Bacteria(1.0000), p: Firmicutes(0.6126), c: Clostridia(0.2851), o: Clostridiales(0.1324), f: Clostridiaceae_1(0.0208), g: *Clostridium*_sensu_stricto(0.0066) |
| ascus_1184 | 0.70593 | 0.5578006 | d: Bacteria(1.0000), p: "Bacteroidetes"(0.9992), c: "Bacteroidia"(0.8690), o: "Bacteroidales"(0.5452), f: Bacteroidaceae(0.1062), g: *Bacteroides*(0.0237) |
| ascus_7394 | 0.6269 | 0.5557023 | d: Bacteria(1.0000), p: Firmicutes(0.9939), c: Clostridia(0.7704), o: Clostridiales(0.4230), f: Lachnospiraceae(0.1422), g: *Clostridium*_XIVa(0.0350) |
| ascus_1360 | 0.57343 | 0.5535785 | d: Bacteria(1.0000), p: Firmicutes(0.9992), c: Clostridia(0.9351), o: Clostridiales(0.8605), f: Lachnospiraceae(0.7052), g: *Clostridium*_XIVa(0.2649) |
| ascus_3175 | 0.53565 | 0.54864305 | d: Bacteria(1.0000), p: "Bacteroidetes"(0.9991), c: "Bacteroidia"(0.8955), o: "Bacteroidales"(0.7083), f: "Prevotellaceae"(0.1942), g: *Prevotella*(0.0605) |
| ascus_2581 | 0.68361 | 0.5454486 | d: Bacteria(1.0000), p: "Spirochaetes"(0.9445), c: Spirochaetes(0.8623), o: Spirochaetales(0.5044), f: Spirochaetaceae(0.3217), g: *Spirochaeta*(0.0237) |
| ascus_531 | 0.71315 | 0.5400517 | d: Bacteria(1.0000), p: Firmicutes(0.6126), c: Clostridia(0.2851), o: Clostridiales(0.1324), f: Clostridiaceae_1(0.0208), g: *Clostridium*_sensu_stricto(0.0066) |
| ascus_1858 | 0.65165 | 0.5393882 | d: Bacteria(1.0000), p: "Spirochaetes"(0.9263), c: Spirochaetes(0.8317), o: Spirochaetales(0.4636), f: Spirochaetaceae(0.2792), g: *Spirochaeta*(0.0237) |

Example 3

Increase Total Milk Fat, Milk Protein, and Energy-Corrected Milk (ECM) in Cows

Example 3 shows a specific implementation with the aim to increase the total amount of milk fat and milk protein produced by a lactating ruminant, and the calculated ECM. As used herein, ECM represents the amount of energy in milk based upon milk volume, milk fat, and milk protein. ECM adjusts the milk components to 3.5% fat and 3.2% protein, thus equalizing animal performance and allowing for comparison of production at the individual animal and herd levels over time. An equation used to calculate ECM, as related to the present disclosure, is:

$$ECM = (0.327 \times \text{milk pounds}) + (12.95 \times \text{fat pounds}) + (7.2 \times \text{protein pounds})$$

Application of the methodologies presented herein, utilizing the disclosed methods to identify active interrelated microbes/microbe strains and generating microbial ensembles therefrom, demonstrate an increase in the total amount of milk fat and milk protein produced by a lactating ruminant. These increases were realized without the need for further addition of hormones.

In this example, a microbial ensemble comprising two isolated microbes, Ascusb_X and Ascusf_Y, identified and generated according to the above disclosure, was administered to Holstein cows in mid-stage lactation over a period of five weeks. The cows were randomly assigned into 2 groups of 8, wherein one of the groups was a control group that received a buffer lacking a microbial ensemble. The second group, the experimental group, was administered a microbial ensemble comprising Ascusb_X and Ascusf_Y once per day for five weeks. Each of the cows were housed in individual pens and were given free access to feed and water. The diet was a high milk yield diet. Cows were fed ad libitum and the feed was weighed at the end of the day, and prior day refusals were weighed and discarded. Weighing was performed with a PS-2000 scale from Salter Brecknell (Fairmont, Minn.).

Cows were cannulated such that a cannula extended into the rumen of the cows. Cows were further provided at least 10 days of recovery post cannulation prior to administering control dosages or experimental dosages.

Administration to the control group consisted of 20 ml of a neutral buffered saline, while administration to the experimental group consisted of approximately $10^9$ cells suspended in 20 mL of neutral buffered saline. The control group received 20 ml of the saline once per day, while the experimental group received 20 ml of the saline further comprising $10^9$ microbial cells of the described microbial ensemble.

The rumen of every cow was sampled on days 0, 7, 14, 21, and 35, wherein day 0 was the day prior to microbial administration. Note that the experimental and control administrations were performed after the rumen was sampled on that day. Daily sampling of the rumen, beginning on day 0, with a pH meter from Hanna Instruments (Woonsocket, R.I.) was inserted into the collected rumen fluid for recordings. Rumen sampling included both particulate and fluid sampling from the center, dorsal, ventral, anterior, and posterior regions of the rumen through the cannula, and all five samples were pooled into 15 ml conical vials containing 1.5 ml of stop solution (95% ethanol, 5% phenol). A fecal sample was also collected on each sampling day, wherein feces were collected from the rectum with the use of a palpation sleeve. Cows were weighed at the time of each sampling.

Fecal samples were placed in a 2 ounce vial, stored frozen, and analyzed to determine values for apparent neutral detergent fibers (NDF) digestibility, apparent starch digestibility, and apparent protein digestibility. Rumen sampling consisted of sampling both fluid and particulate portions of the rumen, each of which was stored in a 15 ml conical tube. Cells were fixed with a 10% stop solution (5% phenol/95% ethanol mixture) and kept at 4° C. and shipped to Ascus Biosciences (San Diego, Calif.) on ice.

The milk yield was measured twice per day, once in the morning and once at night. Milk composition (% fats and % proteins, etc.) was measured twice per day, once in the morning and once at night. Milk samples were further analyzed with near-infrared spectroscopy for protein fats, solids, analysis for milk urea nitrogen (MUN), and somatic cell counts (SCC) at the Tulare Dairy Herd Improvement Association (DHIA) (Tulare, Calif.). Feed intake of individual cows and rumen pH were determined once per day.

A sample of the total mixed ration (TMR) was collected the final day of the adaptation period, and then successively collected once per week. Sampling was performed with the quartering method, wherein the samples were stored in vacuum sealed bags which were shipped to Cumberland Valley Analytical Services (Hagerstown, Md.) and analyzed with the NIR1 package. The final day of administration of buffer and/or microbial bioensemble was on day 35, however all other measurements and samplings continued as described until day 46.

FIG. 8A demonstrates that cows that received the microbial ensemble based on the disclosed methods exhibited a 20.9% increase in the average production of milk fat versus cows that were administered the buffered solution alone. FIG. 8B demonstrates that cows that were administered the microbial ensemble exhibited a 20.7% increase in the average production of milk protein versus cows that were administered the buffered solution alone. FIG. 8C demonstrates that cows that were administered the microbial ensemble exhibited a 19.4% increase in the average production of energy corrected milk. The increases seen in FIG. 8A-C became less pronounced after the administration of the ensemble ceased, as depicted by the vertical line intersecting the data points.

Example 4

Detection of *Clostridium perfringens* as Causative Agent for Lesion Formation in Broiler Chickens 160 male Cobb 500s were challenged with various levels of *Clostridium perfringens* (Table 6a). They were raised for 21 days, sacrificed, and lesion scored to quantify the progression of necrotic enteritis and the impact of *C. perfringens*.

TABLE 6a

| Treatment | NE Challenge (Y/N) | Treatment Description | No. of Birds/ Pen | No. of Pens | Number of Birds/ Treatment |
|---|---|---|---|---|---|
| 1 | N | Non-Challenged | 20 | 2 | 40 |
| 2 | Y | Challenged with half typical dose (1.25 ml/bird; 2.0-9.0 × $10^8$ cfu/ml) | 20 | 2 | 40 |
| 3 | Y | Challenged with typical dose (2.5 ml/bird; 2.0-9.0 × $10^8$ cfu/ml) | 20 | 2 | 40 |
| 4 | Y | Challenged with twice the typical dose (5.0 ml/bird; 2.0-9.0 × $10^8$ cfu/ml) | 20 | 2 | 40 |
| | | Total | | 8 | 160 |

Experimental Design

Birds were housed within an environmentally controlled facility in wooden floor pens (~4'×4' minus 2.25 sq. ft for feeder space) providing floor space & bird density of [~0.69 ft2/bird], temperature, lighting, feeder and water. Birds were placed in clean pens containing an appropriate depth of wood shavings to provide a comfortable environment for the chicks. Additional shavings were added to pens if they become too damp for comfortable conditions for the test birds during the study. Lighting was via incandescent lights and a commercial lighting program was used as follows.

TABLE 6b

| Approximate Bird Age (days) | Approximate Hours of Continuous Light per 24 hr period | ~Light Intensity (foot candles) |
|---|---|---|
| 0-4 | 24 | 1.0-1.3 |
| 5-10 | 10 | 1.0-1.3 |
| 11-18 | 12 | 0.2-0.3 |
| 19-end | 16 | 0.2-0.3 |

Environmental conditions for the birds (i.e. bird density, temperature, lighting, feeder and water space) were similar for all treatment groups. In order to prevent bird migration and bacterial spread from pen to pen, each pen had a solid (plastic) divider for approximately 24 inches in height between pens.

Vaccinations and Therapeutic Medication:

Birds were vaccinated for Mareks at the hatchery. Upon receipt (study day 0), birds were vaccinated for Newcastle and Infectious Bronchitis by spray application. Documentation of vaccine manufacturer, lot number and expiration date were provided with the final report.

Water:

Water was provided ad libitum throughout the study via one Plasson drinker per pen. Drinkers were checked twice daily and cleaned as needed to assure a clean and constant water supply to the birds.

Feed:

Feed was provided ad libitum throughout the study via one hanging, ~17-inch diameter tube feeder per pen. A chick feeder tray was placed in each pen for approximately the first 4 days. Birds were placed on their respective treatment diets upon receipt (day 0) according to the Experimental Design. Feed added and removed from pens from day 0 to study end were weighed and recorded.

Daily Observations:

The test facility, pens and birds were observed at least twice daily for general flock condition, lighting, water, feed, ventilation and unanticipated events. If abnormal conditions or abnormal behavior was noted at any of the twice-daily observations they were documented and documentation included with the study records. The minimum-maximum temperatures of the test facility were recorded once daily.

Pen Cards:

There were 2 cards attached to each pen. One card identified the pen number and the second denoted the treatment number.

Animal Handling:

The animals were kept under ideal conditions for livability. The animals were handled in such a manner as to reduce injuries and unnecessary stress. Humane measures were strictly enforced.

Veterinary Care, Intervention and Euthanasia:

Birds that developed clinically significant concurrent disease unrelated to the test procedures were, at the discretion of the Study Investigator, or a designee, removed from the study and euthanized in accordance with site SOPs. In addition, moribund or injured birds were also euthanized upon authority of a Site Veterinarian or a qualified technician. The reasons for any withdrawal were documented. If an animal died, or was removed and euthanized for humane reasons, it was recorded on the mortality sheet for the pen and a necropsy performed and filed to document the reason for removal.

If euthanasia was deemed necessary by the Study Investigator, animals were euthanized by cervical dislocation.

Mortality and Culls:

Starting on study day 0, any bird that was found dead or was removed and sacrificed was weighed and necropsied. Cull birds that were unable to reach feed or water were sacrificed, weighed and documented. The weight and probable cause of death and necropsy findings were recorded on the pen mortality record.

Body Weights and Feed Intake:

Birds were weighed, by pen and individually, on approximately days 14 and 21. The feed remaining in each pen was weighed and recorded on study days 14 and 21. The feed intake during days 14-21 was calculated.

Weight Gains and Feed Conversion:

Average bird weight, on a pen and individual basis, on each weigh day were summarized. The average feed conversion was calculated on study day 21 (i.e. days 0-21) using the total feed consumption for the pen divided by the total weight of surviving birds. Adjusted feed conversion was calculated using the total feed consumption in a pen divided by the total weight of surviving birds and weight of birds that died or were removed from that pen.

*Clostridium Perfringens* Challenge

Method of Administration:

*Clostridium perfringens* (CL-15, Type A, a and (32 toxins) cultures in this study were administered via the feed. Feed from each pen's feeder was used to mix with the culture. Prior to placing the cultures in the pens the treatment feed was removed from the birds for approximately 4-8 hours. For each pen of birds, a fixed amount based on study design of the broth culture at a concentration of approximately $2.0$-$9.0 \times 10^8$ cfu/ml was mixed with a fixed amount of feed (~25 g/bird) in the feeder tray and all challenged pens were treated the same. Most of the culture-feed was consumed within 1-2 hours. So that birds in all treatments are treated similar, the groups that are not challenged also had the feed removed during the same time period as the challenged groups.

*Clostridium* Challenge:

The *Clostridium perfringens* culture (CL-15) was grown ~5 hrs at ~37° C. in Fluid Thioglycollate medium containing starch. CL-15 is a field strain of *Clostridium perfringens* from a broiler outbreak in Colorado. A fresh broth culture was prepared and used each day. For each pen of birds, a fixed amount of the overnight broth culture was mixed with a fixed amount of treatment feed in the feeder tray (see administration). The amount of feed, volume and quantitation of culture inoculum, and number of days dosed were documented in the final report and all pens will be treated the same. Birds received the *C. perfringens* culture for one day (Study day 17).

Data Collected:
Intestinal content for analysis with the Ascus platform methods according to the disclosure.
Bird weights, by pen and individually and feed efficiency, by pen, on approximately days 14 and 21.
Feed amounts added and removed from each pen from day 0 to study end.
Mortality: sex, weight and probable cause of death day 0 to study end.
Removed birds: reason for culling, sex and weight day 0 to study end.
Daily observation of facility and birds, daily facility temperature.
Lesion scores 5 birds/pen on approximate day 21

Lesion Scoring:

Four days following the last *C. perfringens* culture administration, five birds were randomly selected from each pen by first bird caught, sacrificed and intestinal lesions scored for necrotic enteritis. Lesions scored as follows:
0=normal: no NE lesions, small intestine has normal elasticity (rolls back to normal position after being opened)
1=mild: small intestinal wall is thin and flaccid (remains flat when opened and doesn't roll back into normal position after being opened); excess mucus covering mucus membrane
2=moderate: noticeable reddening and swelling of the intestinal wall; minor ulceration and necrosis of the intestine membrane; excess mucus 3=severe: extensive area(s) of necrosis and ulceration of the small intestinal membrane; significant hemorrhage; layer of fibrin and necrotic debris on the mucus membrane (Turkish towel appearance)

4=dead or moribund: bird that would likely die within 24 hours and has NE lesion score of 2 or more Results The results were analyzed using the methods disclosed above (e.g., as discussed with reference to FIGS. 1A, 1B, and 2, as well as throughout the specification) as well as the conventional correlation approach (as discussed above). Strain-level microbial abundance and activity were determined for the small intestine content of each bird, and these profiles were analyzed with respect to two different bird characteristics: individual lesion score, and average lesion score of the pen.

37 birds were used in the individual lesion score analysis—although 40 birds were scored, only 37 had sufficient intestinal material for analysis. The same sequencing reads and same sequencing analysis pipeline was used for both the Ascus approach of the disclosure and the conventional approach. However, the Ascus approach also integrated activity information, as well as cell count information for each sample, as detailed earlier.

The Ascus mutual information approach was used to score the relationships between the abundance of the active strains and the individual lesion scores of the 37 broilers. Pearson correlations were calculated between the strains and individual lesion scores of the 37 broilers for the conventional approach. The causative strain, C. perfringens, was confirmed via global alignment search against the list of organisms identified from the pool of samples. The rank of this specific strain was then identified on the output of each analysis method. The Ascus approach identified the C. perfringens administered in the experiment as the number one strain linked to individual lesion score. The conventional approach identified this strain as the 26th highest strain linked to individual lesion score.

102 birds were used in the average lesion score analysis. As in the previous case, the same sequencing reads and same sequencing analysis pipeline was used for both the Ascus approach and the conventional approach. Again, the Ascus approach also integrated activity information, as well as cell count information for each sample.

The Ascus mutual information approach was used to score the relationships between the abundance of the active strains and the average lesion score of each pen. Pearson correlations were calculated between the strains and average lesion score of each pen for the conventional approach. The causative strain, C. perfringens, was confirmed via global alignment search against the list of organisms identified from the pool of samples. The rank of this specific strain was then identified on the output of each analysis method. The Ascus approach identified the C. perfringens administered in the experiment as the 4th highest strain linked to average lesion score of the pen. The conventional approach identified C. perfringens as the 15th highest strain linked to average lesion score of the pen. Average lesion score of the pen is a less accurate measurement than individual lesion score due to the variable levels of C. perfringens infection being masked by the bulk/average measurement. The drop in rank when comparing the individual lesion score analysis to the average pen lesion score analysis was expected. The collected metadata is provided below

TABLE 7

| Chicken Number | Treatment Group | Average Lesion Score | Individual Lesion Score |
|---|---|---|---|
| 2112 | 2 | 1.4 | |
| 2113 | 2 | 1.4 | 1 |
| 2115 | 2 | 1.4 | |
| 2116 | 2 | 1.4 | |
| 2117 | 2 | 1.4 | 2 |
| 2118 | 2 | 1.4 | 1 |
| 2119 | 2 | 1.4 | |
| 2120 | 2 | 1.4 | |
| 2124 | 2 | 1.4 | |
| 2125 | 2 | 1.4 | |
| 2126 | 2 | 1.4 | |
| 2127 | 2 | 1.4 | 1 |
| 2129 | 2 | 1.4 | |
| 2130 | 2 | 1.4 | |
| 2131 | 2 | 1.4 | |
| 6917 | 4 | 2.2 | |
| 6919 | 4 | 2.2 | 2 |
| 6920 | 4 | 2.2 | 2 |
| 6922 | 4 | 2.2 | |
| 6923 | 4 | 2.2 | |
| 6924 | 4 | 2.2 | |
| 6925 | 4 | 2.2 | |
| 6927 | 4 | 2.2 | |
| 6928 | 4 | 2.2 | 1 |
| 6929 | 4 | 2.2 | |
| 6930 | 4 | 2.2 | |
| 6931 | 4 | 2.2 | |
| 6932 | 4 | 2.2 | 3 |
| 6934 | 4 | 2.2 | 3 |
| 6935 | 4 | 2.2 | |
| 2134 | 3 | 1.4 | 1 |
| 2135 | 3 | 1.4 | |
| 2136 | 3 | 1.4 | 1 |
| 2137 | 3 | 1.4 | |
| 2139 | 3 | 1.4 | 1 |
| 2140 | 3 | 1.4 | |
| 2142 | 3 | 1.4 | 3 |
| 2144 | 3 | 1.4 | |
| 2145 | 3 | 1.4 | 1 |
| 2149 | 3 | 1.4 | |
| 6937 | 1 | 0.6 | |
| 6938 | 1 | 0.6 | |
| 6939 | 1 | 0.6 | 0 |
| 6940 | 1 | 0.6 | 0 |
| 6941 | 1 | 0.6 | 1 |
| 6942 | 1 | 0.6 | |
| 6943 | 1 | 0.6 | 1 |
| 6944 | 1 | 0.6 | |
| 6950 | 1 | 0.6 | |
| 6951 | 1 | 0.6 | |
| 6952 | 1 | 0.6 | |
| 6953 | 1 | 0.6 | |
| 6954 | 1 | 0.6 | 1 |
| 6955 | 1 | 0.6 | |
| 2152 | 2 | 2.4 | |
| 2153 | 2 | 2.4 | |
| 2154 | 2 | 2.4 | 1 |
| 2156 | 2 | 2.4 | 1 |
| 2157 | 2 | 2.4 | |
| 2158 | 2 | 2.4 | |
| 2160 | 2 | 2.4 | |
| 2162 | 2 | 2.4 | 2 |
| 2165 | 2 | 2.4 | |
| 2167 | 2 | 2.4 | 4 |
| 2168 | 2 | 2.4 | |
| 2170 | 2 | 2.4 | |
| 2171 | 2 | 2.4 | 4 |
| 6956 | 4 | 2.2 | 1 |
| 6959 | 4 | 2.2 | 2 |
| 6960 | 4 | 2.2 | 3 |
| 6962 | 4 | 2.2 | |
| 6963 | 4 | 2.2 | |
| 6955 | 4 | 2.2 | |
| 6966 | 4 | 2.2 | 2 |
| 6970 | 4 | 2.2 | |
| 6971 | 4 | 2.2 | |

TABLE 7-continued

| Chicken Number | Treatment Group | Average Lesion Score | Individual Lesion Score |
|---|---|---|---|
| 6972 | 4 | 2.2 | |
| 6973 | 4 | 2.2 | |
| 6974 | 4 | 2.2 | |
| 6975 | 4 | 2.2 | 3 |
| 2172 | 1 | 0 | |
| 2174 | 1 | 0 | |
| 2175 | 1 | 0 | |
| 2176 | 1 | 0 | 0 |
| 2177 | 1 | 0 | 0 |
| 2178 | 1 | 0 | |
| 2180 | 1 | 0 | |
| 2181 | 1 | 0 | 0 |
| 2183 | 1 | 0 | |
| 2185 | 1 | 0 | |
| 2186 | 1 | 0 | 0 |
| 6976 | 3 | 2.2 | |
| 6977 | 3 | 2.2 | 1 |
| 6978 | 3 | 2.2 | 1 |
| 6983 | 3 | 2.2 | |
| 6984 | 3 | 2.2 | |
| 6986 | 3 | 2.2 | |
| 6987 | 3 | 2.2 | |
| 6989 | 3 | 2.2 | 4 |
| 6990 | 3 | 2.2 | |
| 6992 | 3 | 2.2 | |
| 6994 | 3 | 2.2 | 4 |

Example 5

Ability to Detect Relationships in Complex Microbial Communities Using a Mutual Information-Based Approach Compared to a Correlation-Based Approach A series of rumen samples were collected from three mid-lactation Holstein cows via a cannula during a milk fat depression episode. Rumen samples were collected at 4 AM on day 0, day 7, day 10, day 16, and day 28. Sequencing libraries were prepared from DNA purified from the rumen content and sequenced.

Raw sequencing reads were used to identify all microbial strains present in the pool of samples—4,729 unique strains were identified in the pool of samples. The relative abundance of each microbial strain was then calculated and used for subsequent analysis.

TABLE 8a

| | | Milk fat produced (lbs) | Mock strain values |
|---|---|---|---|
| Cow 1 | Day 0 | 2.99325 | 1.99325 |
| | Day 7 | 2.244 | 1.244 |
| | Day 10 | 2.29296 | 1.29296 |
| | Day 16 | 1.01232 | 0.01232 |
| | Day 28 | 2.6904 | 1.6904 |
| Cow 2 | Day 0 | 2.77356 | 1.77356 |
| | Day 7 | 2.261 | 1.261 |
| | Day 10 | 2.2638 | 1.2638 |
| | Day 16 | 1.416 | 0.416 |
| | Day 28 | 2.2977 | 1.2977 |
| Cow 3 | Day 0 | 2.92784 | 1.92784 |
| | Day 7 | 1.75294 | 0.75294 |
| | Day 10 | 1.79118 | 0.79118 |
| | Day 16 | 2.1299 | 1.1299 |
| | Day 28 | 2.8073 | 1.8073 |

The measured pounds of milk fat produced by each animal at each time point is given in Table 8a. A mock strain was created for use in this analysis by taking the milk fat values and subtracting 1 to ensure that the mock strain and milk fat values trend together identically over time, i.e., a known linear trend/relationship exists between the mock strain and milk fat values. This mock strain was then added to the matrix of all strains previously identified in the community. MIC values and Pearson coefficients were simultaneously calculated between pounds of milk fat produced and all strains within the matrix for various conditions (described below) to establish the sensitivity and robustness of these measures as predictors of relationships.

To test the ability of the disclosed methods to detect relationships relative to the traditional methods, data points for the mock strain were removed one by one (relative abundance set to 0). The MIC and Pearson coefficient was recalculated after the removal of each data point, and the mock strain's rank was recorded (Table 8b). As can be seen, the MIC was a far more robust measure than the Pearson coefficient. Both methods were able to identify the mock strain as the number one strain related to pounds of milk fat produced when no points were removed. However, when one point was removed, the correlation method dropped the mock strain to rank 55, and then to rank 2142 when an additional point was removed. The MIC continued to predict the mock strain as the highest ranked strain until 6 points were removed.

TABLE 8b

| Number of data points removed | Time point removed | Mutual Information | | Correlation | |
|---|---|---|---|---|---|
| | | MIC | Rank | Pearson | Rank |
| 0 | None | 0.99679 | 1 | 1 | 1 |
| 1 | Cow 1, day 0 | 0.99679 | 1 | 0.61970925 | 55 |
| 2 | Cow 1 and 2, day 0 | 0.99679 | 1 | 0.14684153 | 2142 |
| 3 | Cow 1, 2, 3, day 0 | 0.99679 | 1 | 0.14694153 | 2142 |
| 4 | Cow 1, 2, 3, day 0; Cow 1 day 16 | 0.99679 | 1 | 0.12914465 | 2209 |
| 5 | Cow 1, 2, 3, day 0; Cow 1 and 2, day 16 | 0.99679 | 1 | 0.12169253 | 2240 |
| 6 | Cow 1, 2, 3, day 0; Cow 1, 2, 3 day 16 | 0.73678 | 335 | 0.18252417 | 2019 |
| 9 | Cow 1, 2, 3, day 0; Cow 1, 2, 3 day 16; Cow 1, 2, 3 day 28 | 0.6473 | 867 | −0.16308112 | 3438 |

One rationale behind removing points to test sensitivity is that when viewing a microbiome of a group of targets (e.g., animals), there are specific strains that are common to all of them, which can be referred to as the core microbiome. This group can represent a minority of the microbial population of a specific target (e.g., specific animal), and there can be a whole separate population of strains that are only found in a subset/small portion of targets/animals. In some embodiments, the more unique strains (i.e., those not found in all of the animals), can be the ones of particular relevance. Some embodiments of the disclosed methods were developed to address such "gaps" in the datasets and thus target particularly relevant microorganism and strains.

Example 6

Selection of an Ensemble of Active Microorganism Strains to Improve Feed Efficiency in Broiler Chickens 96 male Cobb 500s were raised for 21 days. Weight and feed intake were determined for individual birds, and cecum scrapings were collected after sacrifice. The cecum samples were processed using the methods of the present disclosure to identify an ensemble of microorganisms that will enhance feed efficiency when administered to broiler chickens in a production setting.

Experimental Design

120 Cobb 500 chicks were divided and placed into pens based on dietary treatment. The birds were placed in floor pens by treatment from 0-14D. The test facility was divided into 1 block of 2 pens and 48 blocks of 2 individual cages each. Treatments were assigned to the pens/cages using a complete randomized block design; pens/cages retained their treatments throughout the study. The treatments were identified by numeric codes. Birds were assigned to the cages/pens randomly. Specific treatment groups were as follows in Table 9.

TABLE 9

| Treatment | Treatment Description | Strain | No. of Birds/ Floor Pen | No. of Floor Pens/Trt | No. of Birds/Cage | No. of Cages/Trt | No. Birds/ Treatment |
|---|---|---|---|---|---|---|---|
| 1 | 0.042% Salinomycin | Cobb 500 | 60 | 1 | 1 | 48 | 48 (D14) 60 (D0) |
| 2 | No Salinomycin | Cobb 500 | 60 | 1 | 1 | 48 | 48 (D14) 60 (D0) |

Housing:

Assignment of treatments to cages/pens was conducted using a computer program. The computer-generated assignment were as follows:

Birds were housed in an environmentally controlled facility in a large concrete floor pen (4'×8') constructed of solid plastic (4' tall) with clean litter. At day 14, 96 birds were moved into cages within the same environmentally controlled facility. Each cage was 24"×18"×24".

Lighting was via incandescent lights and a commercial lighting program was used. Hours of continuous light for every 24-hour period were as follows in Table 10.

TABLE 10

| Approximate Bird Age (days) | Approximate Hours of Continuous Light per 24 hr period | ~Light Intensity (foot candles) |
|---|---|---|
| 0-6 | 23 | 1.0-1.3 |
| 7-21 | 16 | 0.2-0.3 |

Environmental conditions for the birds (i.e. 0.53 $ft^2$), temperature, lighting, feeder and water space) were similar for all treatment groups.

In order to prevent bird migration, each pen was checked to assure no openings greater than 1 inch existed for approximately 14 inches in height between pens.

Vaccinations:

Birds were vaccinated for Mareks at the hatchery. Upon receipt (study day 0), birds were vaccinated for Newcastle and Infectious Bronchitis by spray application. Documentation of vaccine manufacturer, lot number and expiration date were provided with the final report.

Water:

Water was provided ad libitum throughout the study. The floor pen water was via automatic bell drinkers. The battery cage water was via one nipple waterer. Drinkers were checked twice daily and cleaned as needed to assure a clean water supply to birds at all times.

Feed:

Feed was provided ad libitum throughout the study. The floor pen feed was via hanging, ~17-inch diameter tube feeders. The battery cage feed was via one feeder trough, 9"×4". A chick feeder tray was placed in each floor pen for approximately the first 4 days.

Daily Observations:

The test facility, pens and birds were observed at least twice daily for general flock condition, lighting, water, feed, ventilation and unanticipated events. The minimum-maximum temperature of the test facility was recorded once daily.

Mortality and Culls:

Starting on study day 0, any bird that was found dead or was removed and sacrificed was necropsied. Cull birds that are unable to reach feed or water were sacrificed and necropsied. The probable cause of death and necropsy findings were recorded on the pen mortality record.

Body Weights and Feed Intake:

~96 birds were weighed individually each day. Feed remaining in each cage was weighed and recorded daily from 14-21 days. The feed intake for each cage was determined for each day.

Weight Gains and Feed Conversion:

Body weight gain on a cage basis and an average body weight gain on a treatment basis were determined from 14-21 days. Feed conversion was calculated for each day and overall for the period 14-21D using the total feed consumption for the cage divided by bird weight. Average treatment feed conversion was determined for the period 14-21 days by averaging the individual feed conversions from each cage within the treatment.

Veterinary Care, Intervention and Euthanasia:

Animals that developed significant concurrent disease, are injured and whose condition may affect the outcome of the study were removed from the study and euthanized at the time that determination is made. Six days post challenge all birds in cages were removed and lesion scored.

Data Collected:

Bird weights and feed conversion, individually each day from days 14-21.

Feed amounts added and removed from floor pen and cage from day 0 to study end.

Mortality: probable cause of death day 0 to study end.

Removed birds: reason for culling day 0 to study end.

Daily observation of facility and birds, daily facility temperature.

Cecum content from each bird on day 21.

Results

The results were analyzed using the methods disclosed above (e.g., as discussed with reference to FIGS. 1A, 1B, and 2, as well as throughout the specification). Strain-level microbial abundance and activity were determined for the cecal content of each bird. A total of 22,461 unique strains were detected across all 96 broiler cecum samples. The absolute cell counts of each strain was filtered by the activity threshold to create a list of active microorganism strains and their respective absolute cell counts. On average, only 48.3% of the strains were considered active in each broiler at the time of sacrifice. After filtering, the profiles of active microorganism in each bird were integrated with various bird metadata, including feed efficiency, final body weight, and presence/absence of salinomycin in the diet, in order to select an ensemble that improves performance of all of these traits.

The mutual information approach of the present disclosure was used to score the relationships between the absolute cell counts of the active strains and performance measurements, as well as relationships between two different active strains, for all 96 birds. After applying a threshold, 4039 metadata-strain relationships were deemed significant, and 8842 strain-strain relationships were deemed significant. These links, weighted by MIC score, were then used as edges (with the metadata and strains as nodes) to create a network for subsequent community detection analysis. A Louvain method community detection algorithm was applied to the network to categorize the nodes into subgroups.

The Louvain method optimizes network modularity by first removing a node from its current subgroup, and placing into neighboring subgroups. If modularity of the node's neighbors has improved, the node is reassigned to the new subgroup. If multiple groups have improved modularity, the subgroup with the most positive change is selected. This step is repeated for every node in the network until no new assignments are made. The next step involves the creation of a new, coarse-grained network, i.e. the discovered subgroups become the new nodes. The edges between nodes are defined by the sum of all of the lower-level nodes within each subgroup. From here, the first and second steps are repeated until no more modularity-optimizing changes can be made. Both local (i.e. groups made in the iterative steps) and global (i.e. final grouping) maximas can be investigated to resolve sub-groups that occur within the total microbial community, as well as identify potential hierarchies that may exist.

Modularity:

$$Q = \frac{1}{2m} \sum_{i,j} \left[ A_{ij} - \frac{k_i k_j}{2m} \right] \delta(c_i, c_j)$$

Where A is the matrix of metadata-strain and strain-strain relationships; $k_i = \Sigma_i A_{ij}$ is the total link weight attached to node i; and $m = \frac{1}{2} \Sigma_{ij} A_{ij}$. The Kronecker delta $\delta(c_i, c_j)$ is 1 when nodes i and j are assigned to the same community, and 0 otherwise.

Computing change in modularity when moving nodes:

$$\Delta Q = \left[ \frac{\Sigma_{in} + k_{i,in}}{2m} - \left( \frac{\Sigma_{tot} + k_i}{2m} \right)^2 \right] - \left[ \frac{\Sigma_{in}}{2m} - \left( \frac{\Sigma_{tot}}{2m} \right)^2 - \left( \frac{k_i}{2m} \right)^2 \right]$$

$\Delta Q$ is the gain in modularity in subgroup C. $\Sigma_{in}$ is the sum of the weights of the link in C, $\Sigma_{tot}$ is the sum of the weights of the links incident to nodes in C, $k_i$ is the sum of weights of links incident to node i, $k_{i,in}$ is the sum of weights of links from I to nodes in C, and m is the sum of the weights of all links in the network.

Five different subgroups were detected in the chicken microbial community using the Louvain community detection method. Although a vast amount of microbial diversity exists in nature, there is far less functional diversity. Similarities and overlaps in metabolic capability create redundancies. Microorganism strains responding to the same environmental stimuli or nutrients are likely to trend similarly—this is captured by the methods of the present disclosure, and these microorganisms will ultimately be grouped together. The resulting categorization and hierarchy reveal predictions of the functionality of strains based on the groups they fall into after community-detection analysis.

After the categorization of strains is completed, microorganism strains are cultured from the samples. Due to the technical difficulties associated with isolating and growing axenic cultures from heterogeneous microbial communities, only a small fraction of strains passing both the activity and relationship thresholds of the methods of the present disclosure will ever be propagated axenically in a laboratory setting. After cultivation is completed, the ensemble of microorganism strains is selected based on whether or not an axenic culture exists, and which subgroups the strains were categorized into. Ensembles are created to contain as much functional diversity possible—that is, strains are selected such that a diverse range of subgroups are represented in the ensemble. These ensembles are then tested in efficacy and field studies to determine the effectiveness of the ensemble of strains as a product, and if the ensemble of strains demonstrates a contribution to production, the ensemble of strains could be produced and distributed as a product.

Example 7

Using Small Sample Sizes to Identify Active Microorganism Strains

As detailed below, as few as two samples can be effective to identify active microorganism strains. In particular, the below experiment show that the methods of the disclosure properly identify C. perfringens as an active microorganism strain and causative agent of intestinal lesions and necrotic enteritis for all comparisons, including in a 2 sample comparison.

Experimental Design

Birds housed within an environmentally controlled facility in concrete floor pens (~4'×4' minus 2.25 sq ft of feeder space) providing floor space & bird density of [~0.55 ft$^2$/bird (day 0); ~0.69 ft$^2$/bird (day 21 after lesion scores)], temperature, humidity, lighting, feeder and water space will be similar for all test groups. Birds placed in clean pens containing an appropriate depth of clean wood shavings to provide a comfortable environment for the chicks. Additional shavings added to pens in order to maintain bird comfort. Lighting via incandescent lights and a commercial lighting program used as follows.

TABLE 11

| Approximate Bird Age (days) | Approximate Hours of Continuous Light per 24 hr period | ~Light Intensity (foot candles) |
| --- | --- | --- |
| 0-4 | 24 | 1.0-1.3 |
| 5-10 | 10 | 1.0-1.3 |
| 11-18 | 12 | 0.2-0.3 |
| 19-end | 16 | 0.2-0.3 |

Environmental conditions for the birds (i.e., bird density, temperature, lighting, feeder and water space) were similar for all treatment groups. In order to prevent bird migration and bacterial spread from pen to pen, each pen had a solid (plastic) divider of approximately 24 inches in height between pens.

Vaccinations and Therapeutic Medication:

Birds were vaccinated for Mareks at the hatchery. Upon receipt (study day 0), birds were vaccinated for Newcastle and Infectious Bronchitis by spray application. Documentation of vaccine manufacturer, lot number and expiration date were provided with the final report.

Water:

Water was provided ad libitum throughout the study via one Plasson drinker per pen. Drinkers were checked twice daily and cleaned as needed to assure a clean and constant water supply to the birds.

Feed:

Feed was provided ad libitum throughout the study via one hanging, ~17-inch diameter tube feeder per pen. A chick feeder tray was placed in each pen for approximately the first 4 days. Birds were placed on their respective treatment diets upon receipt (day 0) according to the Experimental Design. Feed added and removed from pens from day 0 to study end were weighed and recorded.

Daily Observations:

The test facility, pens and birds were observed at least twice daily for general flock condition, lighting, water, feed, ventilation and unanticipated events. If abnormal conditions or abnormal behavior is noted at any of the twice-daily observations they were documented, and the documentation was included with the study records. The minimum-maximum temperature of the test facility were recorded once daily.

Pen Cards:

There were 2 cards attached to each pen. One card identified the pen number and the second denoted the treatment number.

Animal Handling:

The animals were kept under ideal conditions for livability. The animals were handled in such a manner as to reduce injuries and unnecessary stress. Humane measures were strictly enforced.

Veterinary Care, Intervention and Euthanasia:

Birds that develop clinically significant concurrent disease unrelated to the test procedures may, at the discretion of the Study Investigator, or a designee, be removed from the study and euthanized in accordance with site SOPs. In addition, moribund or injured birds may also be euthanized upon authority of a Site Veterinarian or a qualified technician. The reasons for withdrawal were documented. If an animal dies, or is removed and euthanized for humane reasons, it was recorded on the mortality sheet for the pen and a necropsy was performed and filed to document the reason for removal.

If euthanasia was deemed necessary by the Study Investigator, animals were euthanized by cervical dislocation.

Mortality and Culls:

Starting on study day 0, any bird that was found dead or was removed and sacrificed was weighed and necropsied. Cull birds that were unable to reach feed or water were sacrificed, weighed and documented. The weight and probable cause of death and necropsy findings were recorded on the pen mortality record.

*Clostridium Perfringens* Challenge

Method of Administration:

*Clostridium perfringens* (CL-15, Type A, a and (32 toxins) cultures in this study were administered via the feed. Feed from each pen's feeder was used to mix with the culture. Prior to placing the cultures in the pens the treatment feed was removed from the birds for approximately 4-8 hours. For each pen of birds, a fixed amount based on study design of the broth culture at a concentration of approximately 2.0-9.0×$10^8$ cfu/ml was mixed with a fixed amount of feed (~25 g/bird) in the feeder tray and all challenged pens were treated the same. Most of the culture-feed was consumed within 1-2 hours. So that birds in all treatments were treated similarly, the groups that are not challenged also had the feed removed during the same time period as the challenged groups.

*Clostridium* Challenge:

The *Clostridium perfringens* culture (CL-15) was grown ~5 hrs at ~37° C. in Fluid Thioglycollate medium containing starch. CL-15 is a field strain of *Clostridium perfringens* from a broiler outbreak in Colorado. A fresh broth culture was prepared and used each day. For each pen of birds, a fixed amount of the overnight broth culture was mixed with a fixed amount of treatment feed in the feeder tray. The amount of feed, volume and quantitation of culture inoculum, and number of days dosed were documented in the final report and all pens will be treated the same. Birds will receive the *C. perfringens* culture for one day (Study day 17).

Data Collected

Intestinal content for analysis with the methods of the present application

Bird weights, by pen and individually, and feed efficiency, by pen, on approximately days 14 and 21.

Feed amounts added and removed from each pen from day 0 to study end.

Mortality: sex, weight and probable cause of death day 0 to study end.

Removed birds: reason for culling, sex and weight day 0 to study end.

Daily observation of facility and birds, daily facility temperature.

Lesion score 5 birds/pen on approximate day 21

Samples collected from 48 lesion scored birds

Lesion Scoring:

Four days following the last *C. perfringens* culture administration, five birds were randomly selected from each pen by first bird caught, sacrificed and intestinal lesions scored for necrotic enteritis. Lesions scored as follows:

0=normal: no NE lesions, small intestine has normal elasticity (rolls back to normal position after being opened)

1=mild: small intestinal wall is thin and flaccid (remains flat when opened and doesn't roll back into normal position after being opened); excess mucus covering mucus membrane 2=moderate: noticeable reddening and swelling of the intestinal wall; minor ulceration and necrosis of the intestine membrane; excess mucus 3=severe: extensive area(s) of necrosis and ulceration of the small intestinal membrane; significant hemorrhage; layer of fibrin and necrotic debris on the mucus membrane (Turkish towel appearance)

4=dead or moribund: bird that would likely die within 24 hours and has NE lesion score of 2 or more Results The results were analyzed using the methods of the present application. Strain-level microbial absolute cell count and activity were determined for the small intestine content of all 48 birds. The methods of the present application integrated activity information, as well as absolute cell count information for each sample.

The mutual information approach of the present application was used to score the relationships between the absolute cell count of the active strains and the individual lesion scores of 10 randomly selected broilers. One sample was randomly removed from the dataset, and the analysis was repeated. This was repeated until only two broiler samples were compared.

The causative strain, *C. perfringens*, was confirmed via global alignment search against the list of organisms identified from the pool of samples. Its rank (with a rank position of 1 being the strain most implicated in causing lesion scores) against all strains analyzed are presented in Table 12:

TABLE 12

| Number of Samples | Rank |
|---|---|
| 10 | 1 |
| 9 | 1 |
| 8 | 1 |
| 7 | 1 (2 tied for 1) |
| 6 | 1 (3 tied for 1) |
| 5 | 1 (3 tied for 1) |
| 4 | 1 (3 tied for 1) |
| 3 | 1 (25 tied for 1) |
| 2 | 1 (31 tied for 1) |

Table 12 illustrates that *C. perfringens* was properly identified as an active microorganism strain and causative agent of lesion scores for all comparisons, including the 2 sample comparison, using the disclosed methods. As the sample number was reduced, the number of false positives (i.e., other strains also being identified as causative agents) increased beginning at the 7-sample comparison where two strains, including *C. perfringens*, tied for a rank of 1. This trend continued down to the 2 sample comparison, where 31 strains, including *C. perfringens*, tied for the number 1 rank.

Generally, while using additional samples can reduce the noise/number of false positives, further analysis and processing of the resulting strains can be used to identify *C. perfringens* as the causative strain, including from a total of 31 identified strains. Depending on the embodiment, configuration, and application, methods of the disclosure can be practiced with small numbers of samples, and the number of samples utilized can vary depending on the sample source, sample type, metadata, complexity of the target microbiome, and so forth.

Additional Example Embodiments

Embodiment A1 is a method, comprising: obtaining at least two samples sharing at least one common characteristic and having at least one different characteristic; for each sample, detecting the presence of one or more microorganism types in each sample; determining a number of each detected microorganism type of the one or more microorganism types in each sample; measuring a number of unique first markers in each sample, and quantity thereof, each unique first marker being a marker of a microorganism strain; integrating the number of each microorganism type and the number of the first markers to yield the absolute cell count of each microorganism strain present in each sample; measuring at least one unique second marker for each microorganism strain based on a specified threshold to determine an activity level for that microorganism strain in each sample; filtering the absolute cell count by the determined activity to provide a list of active microorganisms strains and their respective absolute cell counts for each of the at least two samples; comparing the filtered absolute cell counts of active microorganisms strains for each of the at least two samples with at least one measured metadata or additional active microorganism strain for each of the at least two samples and categorizing the active microorganism strains into at least two groups based on predicted function and/or chemistry; selecting at least one microorganism strain from the at least two groups; and combining the selected at least one microorganism strain from the at least two groups to form a ensemble of microorganisms configured to alter a property corresponding to the at least one metadata.

Embodiment A2 is a method according to embodiment A1, wherein measuring the number of unique first markers includes measuring the number of unique genomic DNA markers in each sample. Embodiment A3 is a method according to embodiment A1, wherein measuring the number of unique first markers includes measuring the number of unique RNA markers in each sample. Embodiment A4 is a method according to embodiment A1, wherein measuring the number of unique first markers includes measuring the number of unique protein markers in each sample. Embodiment A5 is a method according to embodiment A1, wherein measuring the number of unique first markers includes measuring the number of unique metabolite markers in each sample. Embodiment A6 is a method according to embodiment A5, wherein measuring the number of unique metabolite markers includes measuring the number of unique lipid markers in each sample. Embodiment A7 is a method according to embodiment A5, wherein measuring the number of unique metabolite markers includes measuring the number of unique carbohydrate markers in each sample. Embodiment A8 is a method according to embodiment A1, wherein measuring the number of unique first markers, and quantity thereof, includes subjecting genomic DNA from each sample to a high throughput sequencing reaction. Embodiment A9 is a method according to embodiment A1, wherein measuring the number of unique first markers, and quantity thereof, includes subjecting genomic DNA from each sample to metagenome sequencing. Embodiment A10 is a method according to embodiment A1, wherein the unique first markers include at least one of an mRNA marker, an siRNA marker, and/or a ribosomal RNA marker. Embodiment A11 is a method according to embodiment A1, wherein the unique first markers include at least one of a sigma factor, a transcription factor, nucleoside associated protein, and/or metabolic enzyme.

Embodiment A12 is a method according to any one of embodiments A1-A11, wherein measuring the at least one unique second marker includes measuring a level of expression of the at least one unique second marker in each sample. Embodiment A13 is a method according to embodiment A12, wherein measuring the level of expression of the at least one unique second marker includes subjecting mRNA in the sample to gene expression analysis. Embodiment A14 is a method according to embodiment A13, wherein the gene expression analysis includes a sequencing reaction. Embodiment A15 is a method according to embodiment A13, wherein the gene expression analysis includes a quantitative polymerase chain reaction (qPCR), metatranscriptome sequencing, and/or transcriptome sequencing. Embodiment A16 is a method according to embodiment A12, wherein measuring the level of expression of the at least one unique second marker includes subjecting each sample or a portion thereof to mass spectrometry analysis. Embodiment A17 is a method according to embodiment A12, wherein measuring the level of expression of the at least one unique second marker includes subjecting each sample or a portion thereof to metaribosome profiling, or ribosome profiling.

Embodiment A18 is a method according to any one of embodiments A1-A17, wherein the one or more microorganism types includes bacteria, archaea, fungi, protozoa, plant, other eukaryote, viruses, viroids, or a combination thereof. Embodiment A19 is a method according to any one of embodiments A1-A18, wherein the one or more microorganism strains is one or more bacterial strains, archaeal strains, fungal strains, protozoa strains, plant strains, other eukaryote strains, viral strains, viroid strains, or a combination thereof. Embodiment A20 is a method according to embodiment A19, wherein the one or more microorganism strains is one or more fungal species or sub-species; and/or wherein the one or more microorganism strains is one or more bacterial species or sub-species.

Embodiment A21 is a method according to any one of embodiments A1-A20, wherein determining the number of each of the one or more microorganism types in each sample includes subjecting each sample or a portion thereof to sequencing, centrifugation, optical microscopy, fluorescent microscopy, staining, mass spectrometry, microfluidics, quantitative polymerase chain reaction (qPCR), gel electrophoresis, and/or flow cytometry.

Embodiment A22 is a method according to embodiment A1, wherein the unique first markers include a phylogenetic marker comprising a 5S ribosomal subunit gene, a 16S ribosomal subunit gene, a 23S ribosomal subunit gene, a 5.8S ribosomal subunit gene, a 18S ribosomal subunit gene, a 28S ribosomal subunit gene, a cytochrome c oxidase subunit gene, a β-tubulin gene, an elongation factor gene, an RNA polymerase subunit gene, an internal transcribed spacer (ITS), or a combination thereof.

Embodiment A22a is a method according to embodiment A1, wherein the unique first marker does not include a phylogenetic marker. Embodiment A22b is a method according to embodiment A1, wherein the unique first marker does not include a phylogenetic marker comprising a 5S ribosomal subunit gene. Embodiment A22c is a method according to embodiment A1, wherein the unique first marker does not include a phylogenetic marker comprising a 16S ribosomal subunit gene. Embodiment A22d is a method according to embodiment A1, wherein the unique first marker does not include a phylogenetic marker comprising a 23S ribosomal subunit gene. Embodiment A22e is a method according to embodiment A1, wherein the unique first marker does not include a phylogenetic marker comprising a 5.8S ribosomal subunit gene. Embodiment A22f is a method according to embodiment A1, wherein the unique first marker does not include a phylogenetic marker comprising a 18S ribosomal subunit gene. Embodiment A22g is a method according to embodiment A1, wherein the unique first marker does not include a phylogenetic marker comprising a 28S ribosomal subunit gene. Embodiment A22h is a method according to embodiment A1, wherein the unique first marker does not include a phylogenetic marker comprising a cytochrome c oxidase subunit gene. Embodiment A22i is a method according to embodiment A1, wherein the unique first marker does not include a phylogenetic marker comprising a β-tubulin gene. Embodiment A22j is a method according to embodiment A1, wherein the unique first marker does not include a phylogenetic marker comprising an elongation factor gene. Embodiment A22k is a method according to embodiment A1, wherein the unique first marker does not include a phylogenetic marker comprising an RNA polymerase subunit gene. Embodiment A22l is a method according to embodiment A1, wherein the unique first marker does not include a phylogenetic marker comprising an internal transcribed spacer (ITS).

Embodiment A23 is a method according to embodiment A22, wherein measuring the number of unique markers, and quantity thereof, includes subjecting genomic DNA from each sample to a high throughput sequencing reaction. Embodiment A24 is a method according to embodiment A22, wherein measuring the number of unique markers, and quantity thereof, comprises subjecting genomic DNA to genomic sequencing. Embodiment A25 is a method according to embodiment A22, wherein measuring the number of unique markers, and quantity thereof, comprises subjecting genomic DNA to amplicon sequencing.

Embodiment A26 is a method according to any one of embodiments A1-A25, wherein the at least one different characteristic includes a collection time at which each of the at least two samples was collected, such that the collection time for a first sample is different from the collection time of a second sample.

Embodiment A27 is a method according to any one of embodiments A1-A25, wherein the at least one different characteristic includes a collection location at which each of the at least two samples was collected, such that the collection location for a first sample is different from the collection location of a second sample.

Embodiment A28 is a method according to any one of embodiments A1-A27, wherein the at least one common characteristic includes a sample source type, such that the sample source type for a first sample is the same as the sample source type of a second sample. Embodiment A29 is a method according to embodiment A28, wherein the sample source type is one of animal type, organ type, soil type, water type, sediment type, oil type, plant type, agricultural product type, bulk soil type, soil rhizosphere type, or plant part type.

Embodiment A30 is a method according to any one of embodiments A1-A27, wherein the at least one common characteristic includes that each of the at least two samples is a gastrointestinal sample.

Embodiment A31 is a method according to any one of embodiments A1-A27, wherein the at least one common characteristic includes an animal sample source type, each sample having a further common characteristic such that each sample is a tissue sample, a blood sample, a tooth sample, a perspiration sample, a fingernail sample, a skin sample, a hair sample, a feces sample, a urine sample, a semen sample, a mucus sample, a saliva sample, a muscle sample, a brain sample, or an organ sample.

Embodiment A32 is a method according to any one of embodiments A1-A31, further comprising: obtaining at least one further sample from a target, based on the at least one measured metadata, wherein the at least one further sample from the target shares at least one common characteristic with the at least two samples; and for the at least one further sample from the target, detecting the presence of one or more microorganism types, determining a number of each detected microorganism type of the one or more microorganism types, measuring a number of unique first markers and quantity thereof, integrating the number of each microorganism type and the number of the first markers to yield the absolute cell count of each microorganism strain present, measuring at least one unique second marker for each microorganism strain to determine an activity level for that microorganism strain, filtering the absolute cell count by the determined activity to provide a list of active microorganisms strains and their respective absolute cell counts for the at least one further sample from the target; wherein the selection of the at least one microorganism strain from each of the at least two groups is based on the list of active microorganisms strains and their respective absolute cell counts for the at least one further sample from the target such that the formed ensemble is configured to alter a property of the target that corresponds to the at least one metadata.

Embodiment A33 is a method according to any one of embodiments A1-A32, wherein comparing the filtered absolute cell counts of active microorganisms strains for each of the at least two samples with at least one measured metadata or additional active microorganism strain for each of the at least two samples includes determining the co-occurrence of the one or more active microorganism strains in each sample with the at least one measured metadata or additional active microorganism strain. Embodiment A34 is a method according to embodiment A33, wherein the at least one measured metadata includes one or more parameters, wherein the one or more parameters is at least one of sample pH, sample temperature, abundance of a fat, abundance of a protein, abundance of a carbohydrate, abundance of a mineral, abundance of a vitamin, abundance of a natural product, abundance of a specified compound, bodyweight of the sample source, feed intake of the sample source, weight gain of the sample source, feed efficiency of the sample source, presence or absence of one or more pathogens, physical characteristic(s) or measurement(s) of the sample source, production characteristics of the sample source, or a combination thereof. Embodiment A35 is a method according to embodiment A34, wherein the one or more parameters is at least one of abundance of whey protein, abundance of casein protein, and/or abundance of fats in milk.

Embodiment A36 is a method according to any one of embodiments A33-A35, wherein determining the co-occurrence of the one or more active microorganism strains and the at least one measured metadata in each sample includes creating matrices populated with linkages denoting metadata and microorganism strain associations, the absolute cell count of the one or more active microorganism strains and the measure of the one more unique second markers to represent one or more networks of a heterogeneous microbial community or communities. Embodiment A37 is a method according to embodiment A36, wherein the at least one measured metadata comprises a presence, activity and/or quantity of a second microorganism strain.

Embodiment A38 is a method according to any one of embodiments A33-A37, wherein determining the co-occurrence of the one or more active microorganism strains and the at least one measured metadata and categorizing the active microorganism strains includes network analysis and/or cluster analysis to measure connectivity of each microorganism strain within a network, wherein the network represents a collection of the at least two samples that share a common characteristic, measured metadata, and/or related environmental parameter. Embodiment A39 is a method according to embodiment A38, wherein the at least one measured metadata comprises a presence, activity and/or quantity of a second microorganism strain. Embodiment A40 is a method according to embodiment A38 or A39, wherein the network analysis and/or cluster analysis includes linkage analysis, modularity analysis, robustness measures, betweenness measures, connectivity measures, transitivity measures, centrality measures, or a combination thereof. Embodiment A41 is a method according to any one of embodiments A38-A40, wherein the cluster analysis includes building a connectivity model, subspace model, distribution model, density model, or a centroid model.

Embodiment A42 is a method according to embodiment A38 or embodiment A39, wherein the network analysis includes predictive modeling of network through link mining and prediction, collective classification, link-based clustering, relational similarity, or a combination thereof. Embodiment A43 is a method according to embodiment A38 or embodiment 3A9, wherein the network analysis comprises differential equation based modeling of populations. Embodiment A44 is a method according to embodiment A43, wherein the network analysis comprises Lotka-Volterra modeling. Embodiment A45 is a method according to embodiment A38 or embodiment A39, wherein the cluster analysis is a heuristic method. Embodiment A46 is a method according to embodiment A45, wherein the heuristic method is the Louvain method.

Embodiment A47 is a method according to embodiment A38 or embodiment A39, where the network analysis includes nonparametric methods to establish connectivity between variables. Embodiment A48 is a method according to embodiment A38 or embodiment A39, wherein the network analysis includes mutual information and/or maximal information coefficient calculations between variables to establish connectivity.

Embodiment A49 is a method for forming an ensemble of active microorganism strains configured to alter a property or characteristic in an environment based on two or more sample sets that share at least one common or related environmental parameter between the two or more sample sets and that have at least one different environmental parameter between the two or more sample sets, each sample set comprising at least one sample including a heterogeneous microbial community, wherein the one or more microorganism strains is a subtaxon of one or more organism types, comprising: detecting the presence of a plurality of microorganism types in each sample; determining the absolute number of cells of each of the detected microorganism types in each sample; measuring the number of unique first markers in each sample, and quantity thereof, wherein a unique first marker is a marker of a microorganism strain; at the protein or RNA level, measuring the level of expression of one or more unique second markers, wherein a unique second marker is a marker of activity of a microorganism strain; determining activity of the detected microorganism strains for each sample based on the level of expression of the one or more unique second markers exceeding a specified threshold; calculating the absolute cell count of each detected active microorganism strain in each sample based upon the quantity of the one or more first markers and the absolute number of cells of the microorganism types from which the one or more microorganism strains is a subtaxon, wherein the one or more active microorganism strains expresses the second unique marker above the specified threshold; determining the co-occurrence of the active microorganism strains in the samples with at least one environmental parameter or additional active microorganism strain based on maximal information coefficient network analysis to measure connectivity of each microorganism strain within a network, wherein the network is the collection of the at least two or more sample sets with at least one common or related environmental parameter; selecting a plurality of active microorganism strains from the one or more active microorganism strains based on the network analysis; and forming an ensemble of active microorganism strains from the selected plurality of active microorganism strains, the ensemble of active microorganism strains configured to selectively alter a property or characteristic of an environment when the ensemble of active microorganism strains is introduced into that environment.

Embodiment A50 is a method according to embodiment A49, wherein the at least one environmental parameter comprises a presence, activity and/or quantity of a second microorganism strain. Embodiment A51 is a method according to embodiment A49 or embodiment A50, wherein at least one measured indicia of at least one common or related environmental factor for a first sample set is different from a measured indicia of the at least one common or related environmental factor for a second sample set.

Embodiment A52 is a method according to embodiment A49 or embodiment A50, wherein each sample set comprises a plurality of samples, and a measured indicia of at least one common or related environmental factor for each sample within a sample set is substantially similar, and an average measured indicia for one sample set is different from the average measured indicia from another sample set. Embodiment A53 is a method according to embodiment A49 or embodiment A50, wherein each sample set comprises a plurality of samples, and a first sample set is collected from a first population and a second sample set is collected from a second population. Embodiment A54 is a method according to embodiment A49 or A50, wherein each sample set comprises a plurality of samples, and a first sample set is collected from a first population at a first time and a second sample set is collected from the first population at a second time different from the first time. Embodiment A55 is a method according to any one of embodiments A49-A54, wherein at least one common or related environmental factor includes nutrient information.

Embodiment A56 is a method according to any one of embodiments A49-A54, wherein at least one common or related environmental factor includes dietary information. Embodiment A57 is a method of any one of embodiments A49-A54, wherein at least one common or related environmental factor includes animal characteristics. Embodiment A58 is a method according to any one of embodiments A49-A54, wherein at least one common or related environmental factor includes infection information or health status.

Embodiment A59 is a method according to embodiment A51, wherein at least one measured indicia is sample pH, sample temperature, abundance of a fat, abundance of a protein, abundance of a carbohydrate, abundance of a mineral, abundance of a vitamin, abundance of a natural product, abundance of a specified compound, bodyweight of the sample source, feed intake of the sample source, weight gain of the sample source, feed efficiency of the sample source, presence or absence of one or more pathogens, physical characteristic(s) or measurement(s) of the sample source, production characteristics of the sample source, or a combination thereof.

Embodiment A60 is a method according to embodiment A49 or embodiment A50, wherein the at least one parameter is at least one of abundance of whey protein, abundance of casein protein, and/or abundance of fats in milk. Embodiment A61 is a method according to any one of embodiments A49-A60, wherein measuring the number of unique first markers in each sample comprises measuring the number of unique genomic DNA markers. Embodiment A62 is a method according to any one of embodiments A49-A60, wherein measuring the number of unique first markers in the sample comprises measuring the number of unique RNA markers. Embodiment A63 is a method according to any one of embodiments A49-A60, wherein measuring the number of unique first markers in the sample comprises measuring the number of unique protein markers.

Embodiment A64 is a method according to any one of embodiments A49-A63, wherein the plurality of microorganism types includes one or more bacteria, archaea, fungi, protozoa, plant, other eukaryote, virus, viroid, or a combination thereof. Embodiment A65 is a method according to any one of embodiments A49-A64, wherein determining the absolute cell number of each of the microorganism types in each sample includes subjecting the sample or a portion thereof to sequencing, centrifugation, optical microscopy, fluorescent microscopy, staining, mass spectrometry, microfluidics, quantitative polymerase chain reaction (qPCR), gel electrophoresis and/or flow cytometry. Embodiment A66 is a method according to any one of embodiments A49-A65, wherein one or more active microorganism strains is a subtaxon of one or more microbe types selected from one or more bacteria, archaea, fungi, protozoa, plant, other eukaryote, virus, viroid, or a combination thereof.

Embodiment A67 is a method according to any one of embodiments A49-A65, wherein one or more active microorganism strains is one or more bacterial strains, archaeal strains, fungal strains, protozoa strains, plant strains, other eukaryote strains, viral strains, viroid strains, or a combination thereof. Embodiment A68 is a method according to any one of embodiments A49-A67, wherein one or more active microorganism strains is one or more fungal species, fungal subspecies, bacterial species and/or bacterial subspecies. Embodiment A69 is a method according to any one of embodiments A49-A68, wherein at least one unique first marker comprises a phylogenetic marker comprising a 5S ribosomal subunit gene, a 16S ribosomal subunit gene, a 23S ribosomal subunit gene, a 5.8S ribosomal subunit gene, a 18S ribosomal subunit gene, a 28S ribosomal subunit gene, a cytochrome c oxidase subunit gene, a beta-tubulin gene, an elongation factor gene, an RNA polymerase subunit gene, an internal transcribed spacer (ITS), or a combination thereof.

Embodiment A70 is a method according to embodiment A49 or embodiment A50, wherein measuring the number of unique first markers, and quantity thereof, comprises subjecting genomic DNA from each sample to a high throughput sequencing reaction. Embodiment A71 is a method according to embodiment A49 or A50, wherein measuring the number of unique first markers, and quantity thereof, comprises subjecting genomic DNA from each sample to metagenome sequencing. Embodiment A72 is a method according to embodiment A49 or A50, wherein a unique first marker comprises an mRNA marker, an siRNA marker, or a ribosomal RNA marker. Embodiment A73 is a method according to embodiment A49 or embodiment A50, wherein a unique first marker comprises a sigma factor, a transcription factor, nucleoside associated protein, metabolic enzyme, or a combination thereof.

Embodiment A74 is a method according to any one of embodiments A49-A73, wherein measuring the level of expression of one or more unique second markers comprises subjecting mRNA in the sample to gene expression analysis. Embodiment A75 is a method according to embodiment A74, wherein the gene expression analysis comprises a sequencing reaction. Embodiment A76 is a method according to embodiment A74, wherein the gene expression analysis comprises a quantitative polymerase chain reaction (qPCR), metatranscriptome sequencing, and/or transcriptome sequencing.

Embodiment A77 is a method according to any one of embodiments A49-A68 and embodiments A74-A76, wherein measuring the level of expression of one or more unique second markers includes subjecting each sample or a portion thereof to mass spectrometry analysis. Embodiment A78 is a method according to any one of embodiments A49-A68 and embodiments A74-A76, wherein measuring the level of expression of one or more unique second markers comprises subjecting the sample or a portion thereof to metaribosome profiling, and/or ribosome profiling.

Embodiment A79 is a method according to any one of embodiments A49-A78, wherein the source type for the samples is one of animal, soil, air, saltwater, freshwater, wastewater sludge, sediment, oil, plant, an agricultural product, bulk soil, soil rhizosphere, plant part, vegetable, an extreme environment, or a combination thereof.

Embodiment A80 is a method according to any one of embodiments A49-A78, wherein each sample is a gastrointestinal sample. Embodiment A81 is a method according to any one of embodiments A49-A78, wherein each sample is one of a tissue sample, blood sample, tooth sample, perspiration sample, fingernail sample, skin sample, hair sample, feces sample, urine sample, semen sample, mucus sample, saliva sample, muscle sample, brain sample, or organ sample.

Embodiment A82 is a processor-implemented method, comprising: receiving sample data from at least two samples sharing at least one common characteristic and having a least one different characteristic; for each sample, determining the presence of one or more microorganism types in each sample; determining a number of each detected microorganism type of the one or more microorganism types in each sample; determining a number of unique first markers in each sample, and quantity thereof, each unique first marker being a marker of a microorganism strain; integrating, via a processor, the number of each microorganism type and the number of the first markers to yield the absolute cell count of each microorganism strain present in each sample; determining an activity level for each microorganism strain in each sample based on a measure of at least one unique second marker for each microorganism strain exceeding a specified threshold, a microorganism strain being identified as active if the measure of at least one unique second marker for that strain exceeds the corresponding threshold; filtering the absolute cell count of each microorganism strain by the determined activity to provide a list of active microorganisms strains and their respective absolute cell counts for each of the at least two samples; conducting a network analysis, via at least one processor, of the filtered absolute cell counts of active microorganisms strains for each of the at least two samples with at least one measured metadata or additional active microorganism strain for each of the at least two samples, the network analysis including determining maximal information coefficient scores between each active microorganism strain and every other active microorganism strain and determining maximal information coefficient scores between each active microorganism strain and the respective at least one measured metadata or additional active microorganism strain; categorizing the active microorganism strains based on predicted function and/or chemistry; identifying a plurality of active microorganism strains based on the categorization; and outputting the identified plurality of active microorganism strains.

Embodiment A83 is the processor-implemented method of embodiment A82, further comprising: assembling an active microorganism ensemble configured to, when applied to a target, alter a property corresponding to the at least one measured metadata. Embodiment A84 is the processor-implemented method of embodiment A82, wherein the output plurality of active microorganism strains is used to assemble an active microorganism ensemble configured to, when applied to a target, alter a property corresponding to the at least one measured metadata. Embodiment A85 is the processor-implemented method of embodiment A82, further comprising: identifying at least one pathogen based on the output plurality of identified active microorganism strains. Embodiment A86 is a processor-implemented method of any one of embodiments A82-A85, wherein the output plurality of active microorganism strains is further used to assemble an active microorganism ensemble configured to, when applied to a target, target the at least one identified pathogen and treat and/or prevent a symptom associated with the at least one identified pathogen.

Embodiment A87 is a method of forming an active microorganism bioensemble of active microorganism strains configured to alter a property in a target biological environment, comprising: obtaining at least two samples sharing at least one common characteristic and having at least one different characteristic; for each sample, detecting the presence of one or more microorganism types in each sample; determining a number of each detected microorganism type of the one or more microorganism types in each sample; measuring a number of unique first markers in each sample, and quantity thereof, each unique first marker being a marker of a microorganism strain; integrating the number of each microorganism type and the number of the first markers to yield the absolute cell count of each microorganism strain present in each sample; measuring at least one unique second marker for each microorganism strain based on a specified threshold to determine an activity level for that microorganism strain in each sample; filtering the absolute cell count by the determined activity to provide a list of active microorganisms strains and their respective absolute cell counts for each of the at least two samples; comparing the filtered absolute cell counts of active microorganisms strains for each of the at least two samples with at least one measured metadata for each of the at least two samples, the comparison including determining the co-occurrence of the active microorganism strains in each sample with the at least one measured metadata, determining the co-occurrence of the active microorganism strains and the at least one measured metadata in each sample including creating matrices populated with linkages denoting metadata and microorganism strain relationships, the absolute cell count of the active microorganism strains, and the measure of the unique second markers, to represent one or more heterogeneous microbial community networks; grouping the active microorganism strains into at least two groups according to predicted function and/or chemistry based on at least one of nonparametric network analysis and cluster analysis identifying connectivity of each active microorganism strain and measured metadata within an active heterogeneous microbial community network; selecting at least one microorganism strain from each of the at least two groups; and combining the selected microorganism strains and with a carrier medium to form a bioensemble of active microorganisms configured to alter a property corresponding to the at least one metadata of target biological environment when the bioensemble is introduced into that target biological environment.

Embodiment A88 is the method according to embodiment A87, further comprising: obtaining at least one further sample, based on the at least one measured metadata, wherein the at least one further sample shares at least one characteristic with the at least two samples; and for the at least one further sample, detecting the presence of one or more microorganism types, determining a number of each detected microorganism type of the one or more microorganism types, measuring a number of unique first markers and quantity thereof, integrating the number of each microorganism type and the number of the first markers to yield the absolute cell count of each microorganism strain present, measuring at least one unique second marker for each microorganism strain to determine an activity level for that microorganism strain, filtering the absolute cell count by the determined activity to provide a list of active microorganisms strains and their respective absolute cell counts for the at least one further sample; wherein comparing the filtered absolute cell counts of active microorganisms strains comprises comparing the filtered absolute cell counts of active microorganism strains for each of the at least two samples and the at least one further sample with the at least one measured metadata, such that the selection of the active microorganism strains is at least partially based on the list of active microorganisms strains and their respective absolute cell counts for the at least one further sample.

Embodiment A89 is a method for forming a synthetic ensemble of active microorganism strains configured to alter a property in a biological environment, based on two or more sample sets each having a plurality of environmental parameters, at least one parameter of the plurality of environmental parameters being a common environmental parameter that is similar between the two or more sample sets and at least one environmental parameter being a different environmental parameter that is different between each of the two or more sample sets, each sample set including at least one sample comprising a heterogeneous microbial community obtained from a biological sample source, at least one of the active microorganism strains being a subtaxon of one or more organism types, the method comprising: detecting the presence of a plurality of microorganism types in each sample; determining the absolute number of cells of each of the detected microorganism types in each sample; measuring the number of unique first markers in each sample, and quantity thereof, a unique first marker being a marker of a microorganism strain; measuring the level of expression of one or more unique RNA markers, wherein a unique RNA marker is a marker of activity of a microorganism strain; determining activity of each of the detected microorganism strains for each sample based on the level of expression of the one or more unique RNA markers exceeding a specified threshold; calculating the absolute cell count of each detected active microorganism strain in each sample based upon the quantity of the one or more first markers and the absolute number of cells of the microorganism types from which the one or more microorganism strains is a subtaxon, the one or more active microorganism strains expressing one or more unique RNA markers above the specified threshold; analyzing the active microorganism strains of the two or more sample sets, the analyzing including conducting nonparametric network analysis of each of the active microorganism strains for each of the two or more sample sets, the at least one common environmental parameter, and the at least one different environmental parameter, the nonparametric network analysis including (1) determining the maximal information coefficient score between each active microorganism strain and every other active microorganism strain and (2) determining the maximal information coefficient score between each active microorganism strain and the at least one different environmental parameter; selecting a plurality of active microorganism strains from the one or more active microorganism strains based on the nonparametric network analysis; and forming a synthetic ensemble of active microorganism strains comprising the selected plurality of active microorganism strains and a microbial carrier medium, the ensemble of active microorganism strains configured to selectively alter a property of a biological environment when the synthetic ensemble of active microorganism strains is introduced into that biological environment.

Embodiment A90 is a method of forming an active microorganism bioensemble configured to alter a property in a target biological environment, comprising: obtaining at least two samples sharing at least one common environmental parameter and having at least one different environmental parameter; for each sample, detecting the presence of one or more microorganism types in each sample; determining a number of each detected microorganism type of the one or more microorganism types in each sample; measuring a number of unique first markers in each sample, and quantity thereof, each unique first marker being a marker of a microorganism strain of a detected microorganism type; determining the absolute cell count of each microorganism strain present in each sample based on the number of each detected microorganism type and the proportional/relative number of the corresponding or related unique first markers for that microorganism type; measuring at least one unique second marker for each microorganism strain based on a specified threshold to determine an activity level for that microorganism strain in each sample; filtering the absolute cell count of each microorganism strain by the determined activity to provide a list of active microorganisms strains and their respective absolute cell counts for each of the at least two samples; comparing the filtered absolute cell counts of active microorganisms strains for each of the at least two samples with at least one measured metadata for each of the at least two samples, the comparison including determining the co-occurrence of the active microorganism strains in each sample with the at least one measured metadata, determining the co-occurrence of the active microorganism strains and the at least one measured metadata in each sample including creating matrices populated with linkages denoting metadata and microorganism strain relationships, the absolute cell count of the active microorganism strains, and the measure of the unique second markers, to represent one or more heterogeneous microbial community networks; grouping the active microorganism strains into at least two groups according to predicted function and/or chemistry based on at least one of nonparametric network analysis and cluster analysis identifying connectivity of each active microorganism strain and measured metadata within an active heterogeneous microbial community network; selecting at least one microorganism strain from each of the at least two groups; and combining the selected microorganism strains and with a carrier medium to form a synthetic bioensemble of active microorganisms configured to alter a property corresponding to the at least one metadata of target biological environment when the bioensemble is introduced into that target biological environment.

While the disclosure has been communicated with reference to the specific embodiments thereof it should be understood by those skilled in the art that various changes may be made and equivalents may be substituted without departing from the true spirit and scope of the disclosure. In addition, many modifications may be made to adopt a particular situation, material, composition of matter, process, process step or steps, to the objective spirit and scope of the described embodiments and disclosure. All such modifications are intended to be within the scope of the disclosure. Patents, patent applications, patent application publications, journal articles and protocols referenced herein are incorporated by reference in their entireties, for all purposes.

While various embodiments have been described and illustrated herein, those of skill in the art will readily envision a variety of other ways and/or structures for performing the function and/or obtaining the results and/or one or more of the advantages described herein, and each of such variations and/or modifications is deemed to be within the scope of the disclosure. More generally, those skilled in the art will readily appreciate that parameters, dimensions, materials, and configurations described herein are provided as illustrative examples, and that the actual parameters, dimensions, materials, and/or configurations will depend upon the specific application(s) or implementation(s) for which the disclosed teachings is/are used. Those skilled in the art will recognize, or be able to ascertain using no more than routine experimentation, equivalents to the specific embodiments described herein. It is, therefore, to be understood that the foregoing embodiments are presented by way of example only and that, within the scope of the appended claims and equivalents thereto; embodiments can be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The above-described embodiments can be implemented in any of numerous ways. For example, the embodiments can be implemented using hardware, software, or a combination thereof. When implemented in software, the software code can be executed on any suitable processor or collection of processors, whether provided in a single computer or distributed among multiple computers.

Further, it should be appreciated that the disclosed methods can be used in conjunction with a computer, which can be embodied in any of a number of forms, such as a rack-mounted computer, a desktop computer, a laptop computer, or a tablet computer. Additionally, a computer can be embedded in a device not generally regarded as a computer but with suitable processing capabilities, including a tablet, Personal Digital Assistant (PDA), a smart phone or any other suitable portable or fixed electronic device.

Also, a computer can have one or more input and output devices, including one or more displays. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer can receive input information through speech recognition or in other audible format.

Such computers can be interconnected by one or more networks in any suitable form, including a local area network or a wide area network, such as an enterprise network, and intelligent network (IN) or the Internet. Such networks can be based on any suitable technology and can operate according to any suitable protocol and can include wireless networks, wired networks or fiber optic networks.

Various methods and processes outlined herein (and/or portions thereof) can be coded as software that is executable on one or more processors that employ any one of a variety of operating systems or platforms. Additionally, such software can be written using any of a number of suitable programming languages and/or programming or scripting tools, and also can be compiled as executable machine language code or intermediate code that is executed on a framework or virtual machine.

In this respect, various disclosed concepts can be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the disclosure discussed above. The computer readable medium or media can be transportable, such that the program or programs stored thereon can be loaded onto one or more different computers or other processors to implement various aspects of the present disclosure as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present disclosure need not reside on a single computer or processor, but can be distributed in a modular fashion amongst a number of different computers or processors to implement various aspects of the present disclosure.

Computer-executable instructions can be in many forms, such as program modules, executed by one or more computers or other devices. Generally, program modules include routines, programs, objects, components, data structures, etc. that perform particular tasks or implement particular abstract data types. Typically the functionality of the program modules can be combined or distributed as desired in various embodiments.

Also, data structures can be stored in computer-readable media in any suitable form. For simplicity of illustration, data structures can be shown to have fields that are related through location in the data structure. Such relationships can likewise be achieved by assigning storage for the fields with locations in a computer-readable medium that convey relationship between the fields. However, any suitable mechanism can be used to establish a relationship between information in fields of a data structure, including through the use of pointers, tags or other mechanisms that establish relationship between data elements.

Also, various disclosed concepts can be embodied as one or more methods, of which examples have been provided. The acts performed as part of the method can be ordered in any suitable way. Accordingly, embodiments can be constructed in which acts are performed in an order different than illustrated, which can include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

Flow diagrams are used herein. The use of flow diagrams is not meant to be limiting with respect to the order of operations performed. The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedia components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements can optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements can optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A method, comprising: forming a bioensemble of active microorganism strains which is able to alter a property in a target biological environment, the forming including:
   obtaining at least two sample sets, each sample set including at least one sample and sharing at least one common environmental parameter;
   detecting a plurality of microorganism types in each sample;
   determining an absolute number of cells of each detected microorganism type of the plurality of microorganism types in each sample;
   measuring unique first markers in each sample, and relative quantity thereof for each microorganism type, each unique first marker being a marker of a microorganism strain of a detected microorganism type;
   determining an absolute cell count of each microorganism strain present in each sample as a function of the absolute number of cells of each detected microorganism type in that sample and the relative quantity of microorganism strains of each detected microorganism type in that sample;
   measuring one or more unique second markers to determine active microorganism strains in each sample;
   generating a set of active microorganism strains and their respective absolute cell counts for each sample;
   analyzing the set of active microorganism strains and respective absolute cell counts for each sample of the at least two sample sets with at least one measured metadata for each of the at least two sample sets to identify relationships between each active microorganism strain and measured metadata;
   selecting a plurality of active microorganism strains from the set of active microorganism strains based on the analysis; and
   combining the selected plurality of active microorganism strains with a carrier medium to form a bioensemble of active microorganisms which is able to after a property of a target biological environment, the property of the target biological environment including a feature indicated by the at least one measured metadata, when the bioensemble is introduced into that target biological environment.

2. The method of claim 1, wherein analyzing the active microorganism strains and respective absolute cell counts for each sample of the at least two sample sets with at least one measured metadata is based on maximal information coefficient network analysis to measure network connectivity of each active microorganism strain and the at least one measured metadata.

3. The method of claim 1, wherein measuring unique first markers, and relative quantity thereof, includes subjecting genomic DNA from each sample to a high throughput sequencing reaction.

4. The method of claim 1, wherein measuring unique first markers, and relative quantity thereof, includes subjecting genomic DNA from each sample to metagenome sequencing.

5. The method of claim 1, wherein the unique first markers include at least one of an mRNA marker, an siRNA marker and/or a ribosomal RNA marker.

6. The method of claim 1, wherein the unique first markers include a sigma factor.

7. The method of claim 1, wherein the unique first markers include a transcription factor.

8. The method of claim 1, wherein the unique first markers include a nucleoside associated protein.

9. The method of claim 1, wherein measuring unique first markers includes at least one of measuring unique genomic DNA markers in each sample, measuring unique RNA markers in each sample, and/or measuring unique protein markers in each sample.

10. The method of claim 1, wherein measuring at least one unique second marker for each microorganism strain includes measuring a level of expression of the at least one unique second marker.

11. The method of claim 10, wherein measuring the level of expression of the at least one unique second marker includes at least one of: subjecting sample mRNA to gene expression analysis; subjecting each sample or a portion thereof to mass spectrometry analysis; and/or subjecting each sample or a portion thereof to metaribosome profiling or ribosome profiling.

12. A processor-implemented method, comprising:
   obtaining data for at least two samples sharing at least one common environmental parameter, each sample of the at least two samples including a heterogeneous microbial community including a plurality of microorganism types;
   determining an absolute number of cells of each microorganism type of the plurality of microorganism types for each sample;
   determining relative quantity of unique first markers for each microorganism type, each unique first marker being a marker of a microorganism strain of a microorganism type;
   measuring a value of one or more unique second markers, a unique second marker indicative of metabolic activity of a particular microorganism strain of a microorganism type;
   determining an activity of each microorganism strain based on the measured value of the one or more unique second markers exceeding a specified threshold;
   determining respective ratios of the absolute number of cells of active microorganism strains for each microorganism type in each sample;
   analyzing each of the active microorganism strains of the at least two samples via a processor, the analysis including identifying relationships between (i) each active microorganism strain and every other active microorganism strain, and (ii) each active microorganism strain and at least one measured metadata;
   displaying, on a graphical interface, identified relationships between active microorganism strains and the at least one measured metadata; and
   formulating a bioensemble comprising a carrier and one or more active microorganism strains based on identified relationships.

13. The processor-implemented method of claim 12, wherein the analysis is based on maximal information coefficient network analysis that measures connectivity of each active microorganism strain to every other active microorganism strain and the at least one measured metadata.

14. The processor-implemented method of claim 12, where an identified relationship is not displayed if the strength thereof does not exceed a specified threshold.

15. The processor-implemented method of claim 12, further comprising assigning each active microorganism strains to one of at least two groups based on predicted function and/or chemistry thereof.

16. The processor-implemented method of claim 12, wherein the analysis includes generating matrices populated with linkages denoting metadata and microorganism strain associations.

17. The processor-implemented method of claim 12, wherein the analysis includes determining co-occurrence of at least one active microorganism strain and another active microorganism strain and/or the at least one measured metadata.

18. The processor-implemented method of claim 17, wherein determining the co-occurrence is based on graph theory.

19. A method, comprising: forming a bioensemble of active microorganism strains which is able to alter feed efficiency of a target animal, the forming including:
   obtaining a plurality of gastrointestinal tract samples;
   obtaining at least one measured metadata from a sample animal population, the measured metadata indicating a feature of at least one of the plurality of gastrointestinal tract samples;
   analyzing the plurality of gastrointestinal tract samples to identify a plurality of microorganism types present and an absolute number of cells for each identified microorganism type for each sample of the plurality of gastrointestinal tract samples;
   measuring unique first markers and relative quantity thereof for each gastrointestinal tract sample of the plurality of gastrointestinal tract samples; a unique first marker being a marker of a microorganism strain of a particular identified microorganism type;
   determining the absolute cell count of each microorganism strain present in each sample as a function of the absolute number of each detected microorganism type in that sample and the relative quantity of unique first markers in that sample;
   measuring at least one unique second marker to determine an activity value for microorganism strains in each gastrointestinal tract sample of the plurality of gastrointestinal tract samples;
   generating a set of active microorganisms strains and their respective absolute cell counts for each gastrointestinal tract sample of the plurality of gastrointestinal tract samples;
   analyzing the active microorganisms strains, respective absolute cell counts, and the at least one measured metadata to identify relationships between active microorganism strains and the at least one measured metadata;

selecting a plurality of active microorganism strains from the set of active microorganism strains based on the analysis; and combining the selected plurality of active microorganism strains with a carrier medium to form a bioensemble of active microorganisms which is able to alter feed efficiency when the bioensemble of active microorganisms is administered to a target animal.

* * * * *